United States Patent
Crich et al.

(10) Patent No.: US 11,912,647 B2
(45) Date of Patent: Feb. 27, 2024

(54) DIVERSITY-ORIENTED SYNTHESIS OF N,N,O-TRISUBSTITUTED HYDROXYLAMINES FROM ALCOHOLS AND AMINES BY N—O BOND FORMATION

(71) Applicant: University of Georgia Research Foundation, Inc., Athens, GA (US)

(72) Inventors: David Crich, Athens, GA (US); Asiri Hettikankanamalage, Athens, GA (US); Jarvis Hill, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 117 days.

(21) Appl. No.: 17/325,291

(22) Filed: May 20, 2021

(65) Prior Publication Data

US 2021/0363098 A1 Nov. 25, 2021

Related U.S. Application Data

(60) Provisional application No. 63/028,653, filed on May 22, 2020.

(51) Int. Cl.
*C07C 239/20* (2006.01)
*C07D 207/46* (2006.01)
*C07B 43/00* (2006.01)

(52) U.S. Cl.
CPC ............ *C07C 239/20* (2013.01); *C07B 43/00* (2013.01); *C07D 207/46* (2013.01)

(58) Field of Classification Search
CPC ....... C07C 239/20; C07B 43/00; C07B 43/04; C07D 207/46
USPC ........................................................ 564/301
See application file for complete search history.

(56) References Cited

U.S. PATENT DOCUMENTS

| | | |
|---|---|---|
| 7,491,846 B2 | 2/2009 | Aoki et al. |
| 7,524,989 B2 | 4/2009 | Williams |
| 8,545,789 B2 | 10/2013 | Yang et al. |
| 9,120,814 B2 | 9/2015 | Park et al. |
| 9,440,953 B2 | 9/2016 | Golebiowski et al. |
| 9,499,511 B2 | 11/2016 | Toscano et al. |
| 10,179,330 B2 | 1/2019 | Srivastava et al. |
| 10,442,812 B2 | 10/2019 | Krainc et al. |
| 10,457,662 B2 | 10/2019 | Neamati et al. |
| 10,472,345 B2 | 11/2019 | Dumas et al. |

OTHER PUBLICATIONS

Banerjee, A. et al. Direct N—O Bond Formation via Oxidation of Amines with Benzoyl Peroxide. Chem. Sci. 2019, 10, 2124.
Biloski, A. J. et al. Improved Oxidation of Amines with Dibenzoyl Peroxide. Synthesis 1983, 7, 537.
Kelly, D. R. et al. The Mechanism of the Tertiary Amine Catalysed Isomerization of Endoperoxides to Hydroxyketones: Synthesis and Chemistry of the Intermediate Postulated in the Peroxide Attack Mechanism. Tetrahedron Lett. 2002, 43, 9331.
Meesters, A. C. M.; et al. The Direct Synthesis of N-t-Alkyl-O-t-butylhydroxylamines from t-Butyl Peroxybenzoate and the Lithium Salts of Primary t-Alkylamines. Synthesis 1978, 9, 679-680.
Miura, Y.; et al. First Isolation of N-Alkoxyaminyl Radicals. Chem. Commun. 2001, 627-628.
Miura, Y.; et al. Isolation and Magnetic Properties of Heterocycle-Carrying N-Alkoxyarylaminyl Radicals. J. Org. Chem. 2003, 68, 10158-10161.
Miura, Y.; et al. Syntheses of Stable N-tert-Alkoxyarylaminyl Mono- and Diradicals by the Reaction of the Lithium Salts pf 2,4,6-Trisubstituted Anilines with tert-Alkyl Mono- and Diperoxybenzoates. J. Org. Chem. 2005, 70, 4177-4179.
Adam et al. Reaction of 1,2-Dioxetanes with Heteroatom Nucleophiles: Adduct Formation by Nucleophilic Attack at the Peroxide Bond. J. Am. Chem. Soc. 1992, 114, 5591-5598.
Adam et al. Reaction of r-Peroxy Lactones with C, N, P, and S Nucleophiles: Adduct Formation and Nucleophile Oxidation by Nucleophilic Attack at and Biphilic Insertion into the Peroxide Bond. J. Org. Chem. 1997, 62, 1623-1629.

*Primary Examiner* — Ana Z Muresan
(74) *Attorney, Agent, or Firm* — Thomas | Horstemeyer, LLP

(57) ABSTRACT

In one aspect, the disclosure relates to a method for the direct synthesis of complex N,N,O-trisubstituted hydroxylamines by N—O bond formation. In another aspect, the method can be successfully employed using a wide variety of commercially available alcohols and secondary amines and enables the construction of large fragment-based libraries of trisubstituted hydroxylamines for drug discovery purposes. Also disclosed are N,N,O-trisubstituted hydroxylamines having low basicity, high stability at ambient temperatures, and an inherent lack of reactivity towards acetylating and sulfonylating enzymes that confer mutagenicity on less-substituted hydroxylamines.

12 Claims, 10 Drawing Sheets

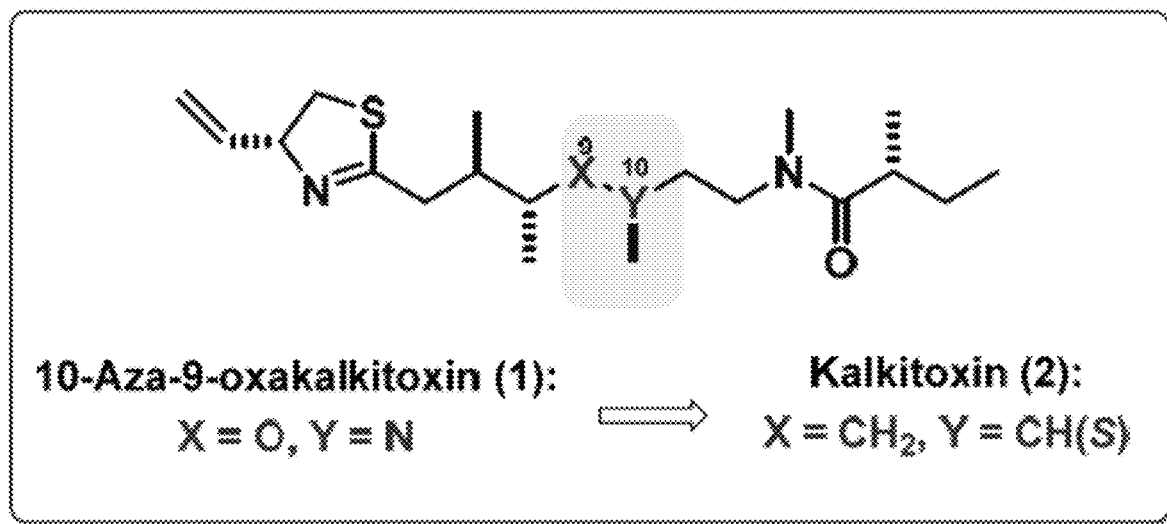
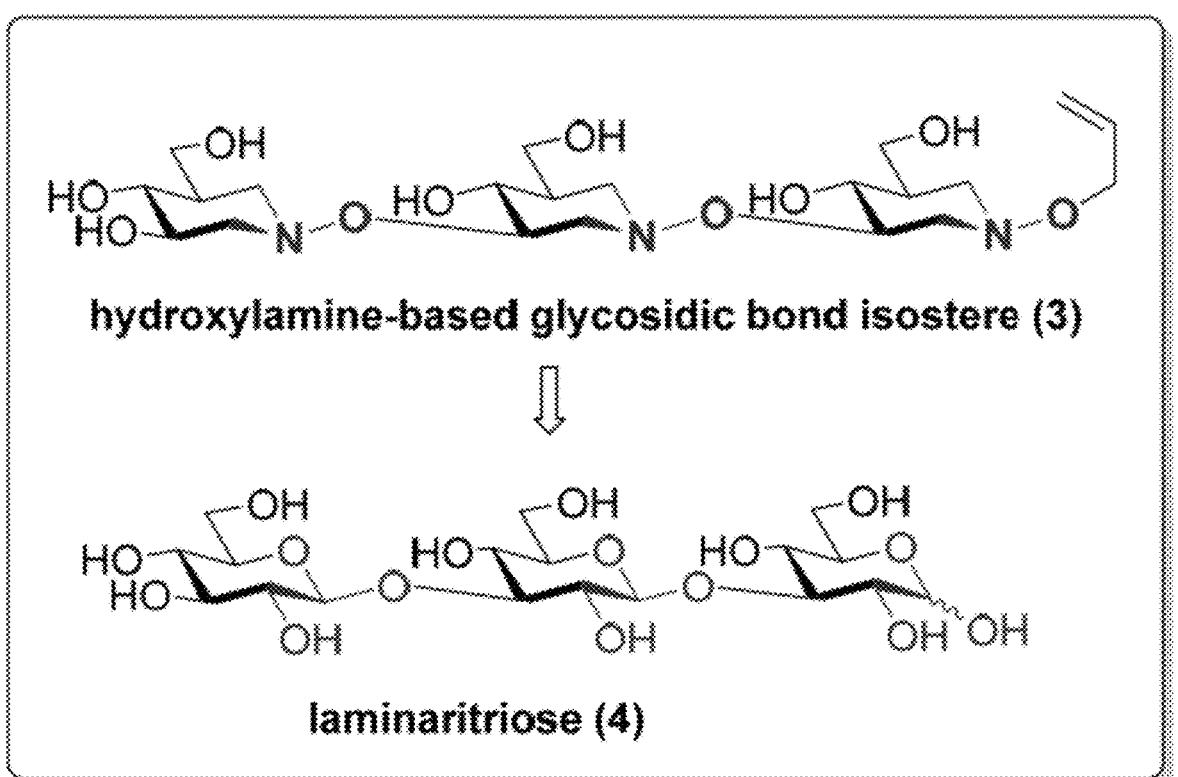
FIG. 1

A. Knight and Foot (2000)
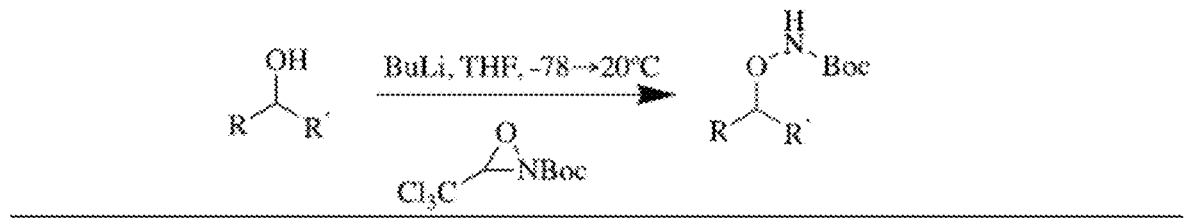
B. Biloski and Ganem (1983)
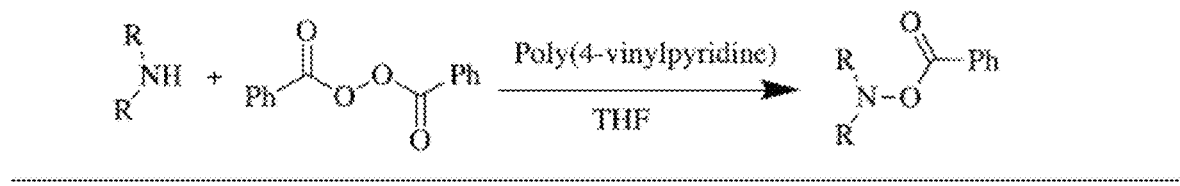
C. Crich and Dhanju (2016)
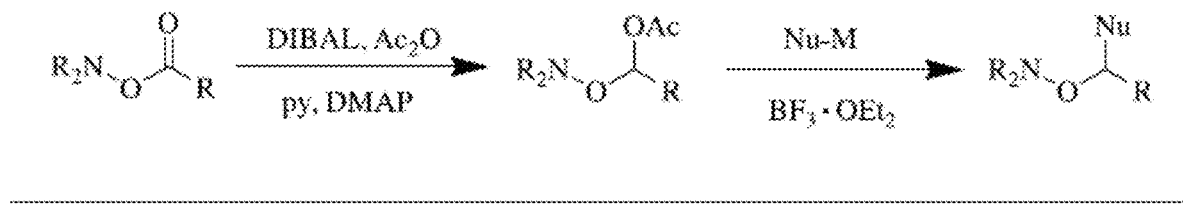
D. Kelly et al. (2002)
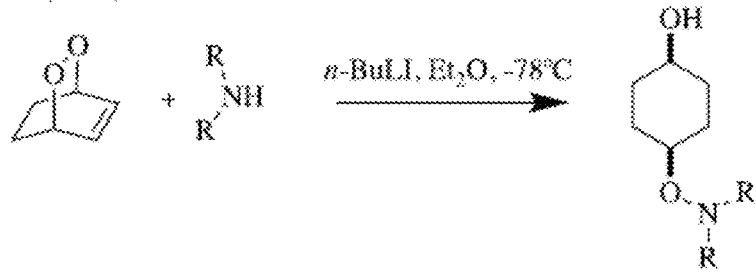
FIGs. 2A-D

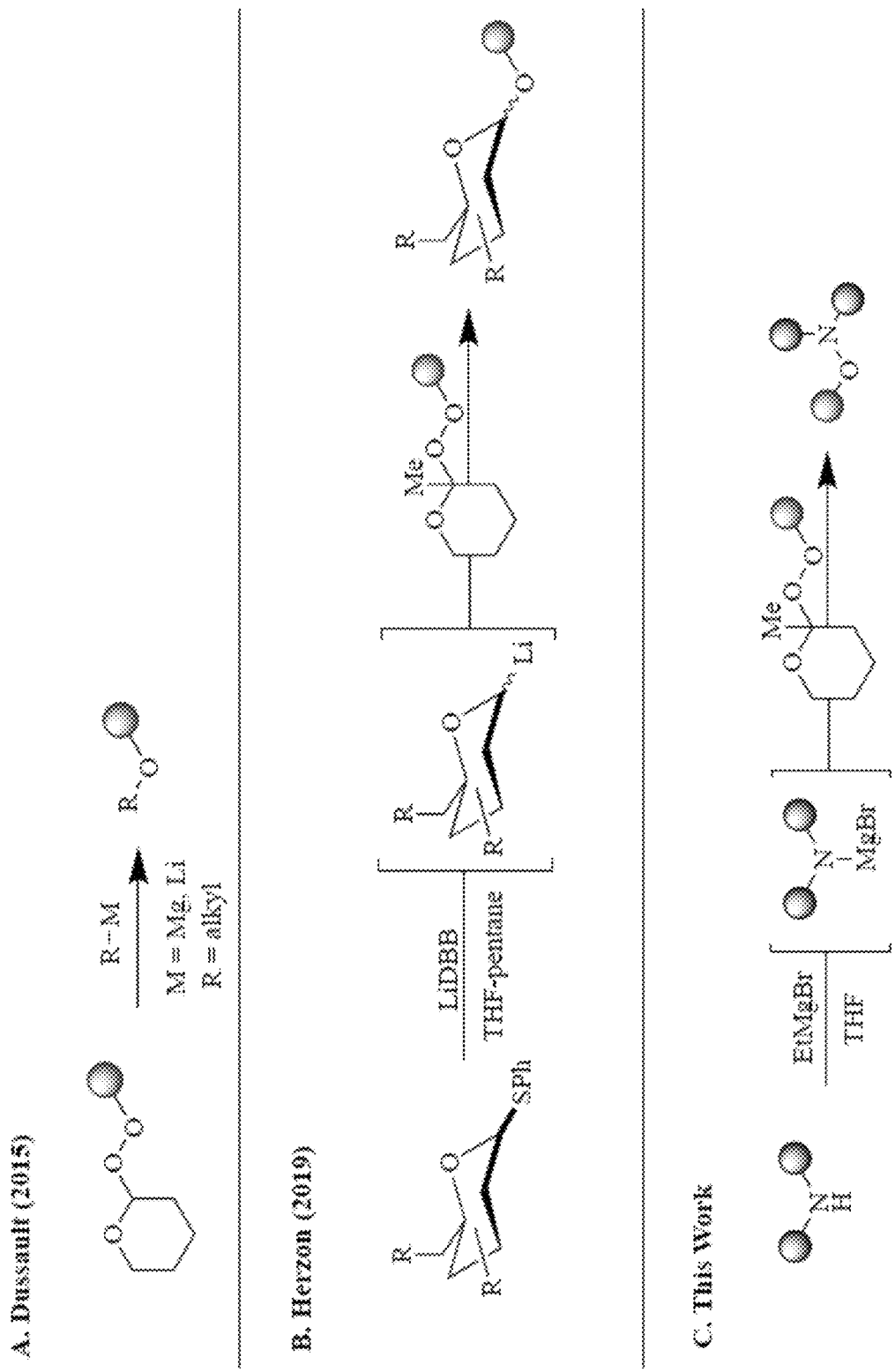
FIGs. 3A-C

A. Lawesson and Yang (1959) - Early report on 1,4-addition of peresters with organometallics:

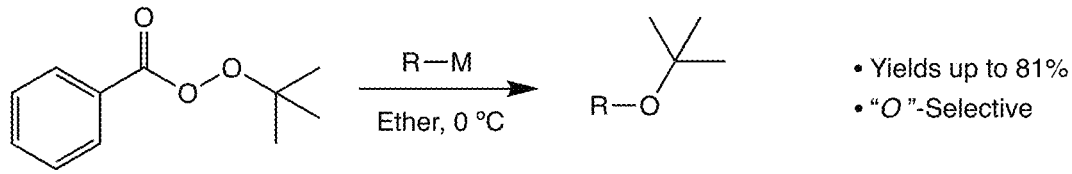

- Yields up to 81%
- "*O*"-Selective

B. Bhanage (2015) - Benzamide formation by 1,2-addition of amines on peresters:

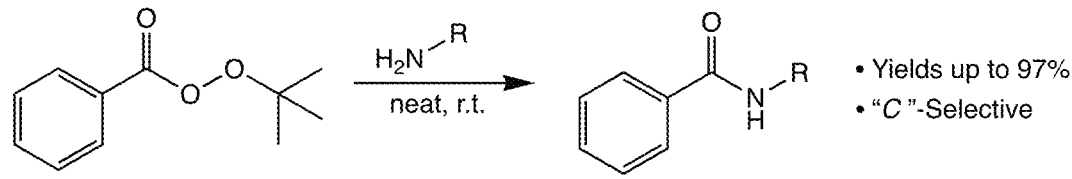

- Yields up to 97%
- "*C*"-Selective

C. Zhang and Gong (2019) - Decarbonylative benzamide formation by 1,2-addition on peresters:

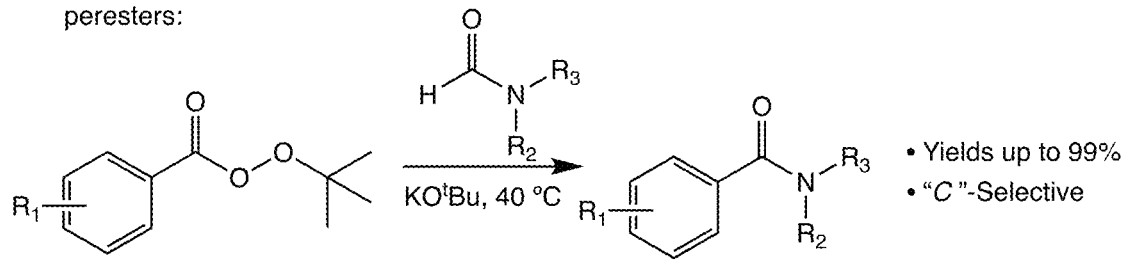

- Yields up to 99%
- "*C*"-Selective

D. Benn and Meesters (1978) - 1,4-Addition of peresters with sterically encumbered primary-*tert*-alkyl lithium amides:

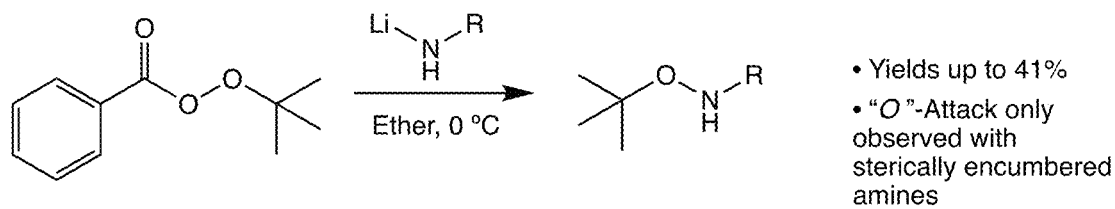

- Yields up to 41%
- "*O*"-Attack only observed with sterically encumbered amines

E. This Work - 1,4-Addition of peresters with broad range of magnesium amides through steric design of perester:

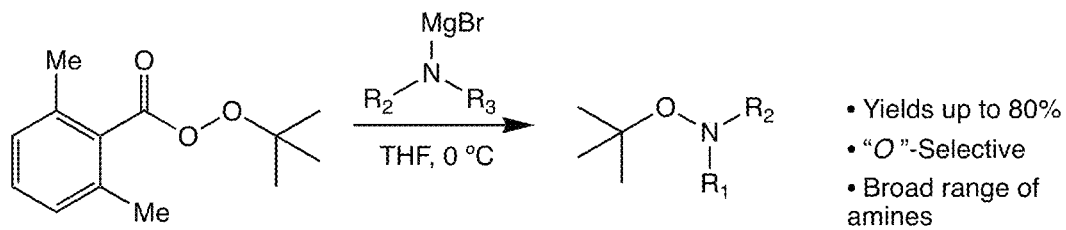

- Yields up to 80%
- "*O*"-Selective
- Broad range of amines

FIGs. 8A-8E

DIVERSITY-ORIENTED SYNTHESIS OF N,N,O-TRISUBSTITUTED HYDROXYLAMINES FROM ALCOHOLS AND AMINES BY N—O BOND FORMATION

CROSS REFERENCE TO RELATED APPLICATIONS

This application claims the benefit of U.S. Provisional Application No. 63/028,653, filed on May 22, 2020, which is incorporated herein by reference in its entirety.

BACKGROUND

New chemical reactions can aid drug discovery by expanding chemical space and increase the likelihood of finding a "lead" compound. However, a large number of newly discovered reactions are primarily focused upon the formation of $sp^2$-$sp^2$ bonds. While these reactions have contributed greatly to drug discovery, they suffer from an inherent bias towards enriching chemical libraries with unsaturated units. Recently, the exploration of natural product-like libraries with increased fractions of $sp^3$-hybridized centers, inclusion of underrepresented functional groups in drug discovery, and the development of fragment-based approaches, have emerged as important strategies for generating complexity and increasing chemical space without significantly increasing molecular weight.

Known syntheses of hydroxylamines by N—O bond formation are limited to the electrophilic amination of alcohols by O-sulfonyl hydroxylamines and other electrophilic nitrogen sources, which are adequate for the installation of the $NH_2$ moiety but do not extrapolate to that of more substituted amino groups. The electrophilic carbamoylation of lithium alkoxides with an N-tert-butoxycarbonyl oxaziridine (FIG. 2A) has been previously described, but several steps would be required to convert the immediate product of this reaction to N,N,O-trisubstituted hydroxylamines. The synthesis of O-acyl N,N-disubstituted hydroxylamines by reaction of secondary amines with diacyl peroxides is widely applied (FIGS. 2B, 2C), but again only indirect access to the N,N,O-trialkylhydroxylamines is provided. Precedent for the direct synthesis N,N,O-trisubstituted hydroxylamines has been observed with the reaction of lithium dialkylamides with an endoperoxide resulting in N—O bond formation in parallel with the anticipated Kornblum-DeLaMare elimination (FIG. 2D). This method, however, was limited exclusively to the synthesis of O-(4-hydroxycyclohexyl) N,N-disubstituted hydroxylamines.

The N,N,O-trisubstituted hydroxylamine moiety is a significantly underrepresented functional group in medicinal chemistry, perhaps due to the widespread perceptions of the mutagenicity of such compounds and the weakness and electrophilicity of heteroatom-heteroatom bonds as novel structural elements for drug discovery. Additionally, broader exploitation of the concept is limited by the paucity of synthetic methods for straightforward synthesis of the core functionality of this group.

Trisubstituted hydroxylamines are attractive as potential achiral replacements for stereogenic centers in natural product-like molecules, while maintaining biological activity. Recently, synthesis of a hydroxylamine analog (hydroxalog) (1) of the potent cytotoxic marine natural product kalkitoxin (2) replacing a backbone 1-methylethylene unit by an N,N,O-trisubstituted hydroxylamine moiety (FIG. 1) was reported to exhibit complete retention of activity toward the human hepatocarcinoma cell line HepG2 and without the introduction of genotoxicity. The concept of trisubstituted hydroxylamines as adaptive replacements of stereogenic $sp^3$-hybridized carbons has also been illustrated by the synthesis of the β-(1→3)-glucan mimetic 3, which retains the affinity of the parent 4 for its lectin receptors (FIG. 1). However, the synthetic methods used for these example compounds are complex and not generally adaptable to a variety of small molecule substrates; thus, this chemical space remains largely unexplored.

It would thus be desirable to develop a facile method for synthesizing a library of trisubstituted hydroxylamines for drug discovery purposes. It would further be desirable if the resulting products could serve as analogs for spa-hybridized carbons while simultaneously exhibiting desirable properties including lack of reactivity towards acetylating and sulfonylating enzymes, low basicity, stability at ambient temperature, and retention of activity with respect to disease targets. These needs and other needs are satisfied by the present disclosure.

SUMMARY

In accordance with the purpose(s) of the present disclosure, as embodied and broadly described herein, the disclosure, in one aspect, relates to a method for the direct synthesis of complex N,N,O-trisubstituted hydroxylamines by N—O bond formation. In another aspect, the method can successfully be employed using a wide variety of commercially available alcohols and secondary amines and enables the construction of large fragment-based libraries of trisubstituted hydroxylamines for drug discovery purposes. Also disclosed are N,N,O-trisubstituted hydroxylamines having low basicity, high stability at ambient temperatures, and an inherent lack of reactivity towards acetylating and sulfonylating enzymes that confer mutagenicity on less-substituted hydroxylamines.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1 shows hydroxylamine analog (hydroxalog) replacement of spa-hybridized carbons as applied to a marine natural product (top) and a β-(1→3)-glucan.

FIGS. 2A-D show previous methods for the synthesis of hydroxylamines.

FIGS. 3A-B show ether formation from MTHP and THP monoperoxy acetals. FIG. 3C shows hydroxylamine formation according to one aspect of the present disclosure.

FIG. 5B shows how a trisubstituted hydroxylamine moiety can be formed in the presence of the azide group, with its broad applications in click chemistry, and how the azide may be reduced to a primary amine in the presence of the hydroxylamine for purposes of further conjugation or derivatization. Further, FIG. 5B illustrates the formation of a trisubstituted hydroxylamine suitable for the preparation of a hydroxalog of the antipsychotic drug aripiprazole.

FIGS. 8A-8D show previously reported nucleophilic displacements of tert-butyl peroxybenzoates, while FIG. 8E shows one exemplary aspect of the current work.

Figure 4:
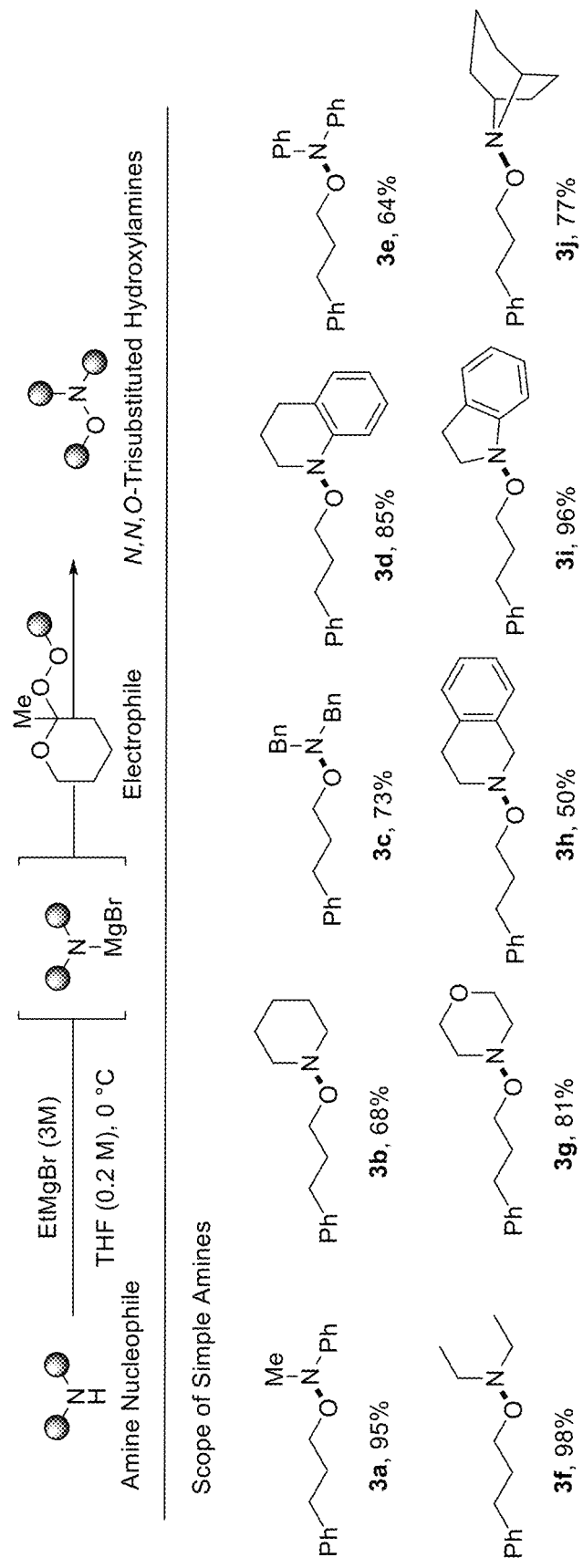
FIG. 4 shows various amine nucleophiles useful in the disclosed reactions as well as yields obtained in the reactions using the nucleophiles.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of".

As used in the specification and the appended claims, the singular forms "a," "an" and "the" include plural referents unless the context clearly dictates otherwise. Thus, for example, reference to "a Grignard reagent," "a secondary amine," or "an amide," includes, but is not limited to, mixtures or combinations of two or more such Grignard reagents, secondary amines, or amides, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "effective amount" refers to an amount that is sufficient to achieve the desired modification of a physical property of the composition or material. For example, an "effective amount" of a Grignard reagent refers to an amount that is sufficient to achieve the desired improvement in the property modulated by the formulation component, e.g. achieving the desired yield of secondary alkyl amide for further reactions. The specific level in terms of wt % in a composition required as an effective amount will depend upon a variety of factors including the amount and type of secondary amine to be transformed, solvent and reaction temperature, amount and type of monoperoxyacetal compound used in the reaction, and similar considerations.

As used herein, the terms "optional" or "optionally" means that the subsequently described event or circumstance can or cannot occur, and that the description includes instances where said event or circumstance occurs and instances where it does not.

A "Grignard agent" or "Grignard reagent" as used herein refers to a compound with the formula R—Mg—X. In a Grignard agent, X is typically a halogen and R is an alkyl or aryl group or another organic group. Examples of Grignard agents include, but are not limited to, Cl—Mg—CHs, $(C_6H_5)$—Mg—Br, and the like. Grignard agents can be useful for creating new carbo-carbon bonds. In one aspect, disclosed herein are reactions using a Grignard agent to generate an alkyl amide that can then be further used to synthesize a N,N,O-trisubstituted hydroxylamine.

An "alkaloid" as used herein refers to a naturally-occurring organic compound incorporating at least one basic nitrogen atom. In some aspects, some synthetic compounds or semisynthetic compounds can also be considered alkaloids. In one aspect, some alkaloids can be useful herein as synthetic precursors to the N,N,O-trisubstituted hydroxylamines disclosed herein. In a further aspect, the alkaloids useful herein incorporate at least one secondary amine moiety.

A "monosaccharide" as used herein refers to a sugar that cannot be hydrolyzed to give a simpler sugar, while a "disaccharide" refers to two monosaccharides connected by a hydrolyzable linkage and a "polysaccharide" refers to three or more monosaccharides connected by hydrolyzable linkages. A "protected" monosaccharide, disaccharide, or polysaccharide refers to a molecule having one or more functional groups reversibly bound to another functional group such that the functional group does not undergo undesired side reactions under conditions of organic synthesis to which the molecule is subjected. Common protection strategies for sugars include formation of acetals or cyclic acetals, addition of benzyl groups to free hydroxyl groups in the sugars, and the like.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted). In one aspect, "substituted" with reference to a linear or branched alkyl group can refer to either replacement of one or more hydrogen atoms with another atom or group (e.g. halogen or nitro), or can refer to substitution of a single bond between carbon atoms with a double or triple bond (e.g.

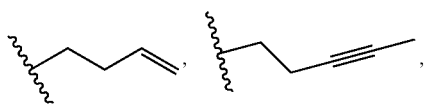

or the like), or any combination thereof.

In defining various terms, "A$^1$," "A$^2$," "A$^3$," and "A$^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "alkanediyl" as used herein, refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH₂C(CH₃)₂CH₂—, and —CH₂CH₂CH₂— are non-limiting examples of alkanediyl groups.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$-OA$^2$ or —OA$^1$-(OA$^2$)$_a$-OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as (A$^1$A$^2$)C═C(A$^3$A$^4$) are intended to include both the E and Z isomers. This can be presumed in structural formulae herein wherein an asymmetric alkene is present, or it can be explicitly indicated by the bond symbol C═C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein. In some aspects, an alkenyl group can be an "alkylalkenyl" group, which can be represented, for example, by the formula —R—X, wherein R represents an alkyl group as defined herein and X is a substituted or unsubstituted alkenyl group.

The term "cycloalkenyl" as used herein is a non-aromatic carbon-based ring composed of at least three carbon atoms and containing at least one carbon-carbon double bound, i.e., C═C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein. In some aspects, an alkynyl group can be an "alkylalkynyl" group, which can be represented, for example, by the formula —R—X, wherein R represents an alkyl group as defined herein and X is a substituted or unsubstituted alkynyl group.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —NH₂, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C═O.

The terms "amine" or "amino" as used herein are represented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein. A specific example of amino is —NH₂.

The term "alkylamino" as used herein is represented by the formula —NH(-alkyl) and —N(-alkyl)₂, where alkyl is a described herein. Representative examples include, but are not limited to, methylamino group, ethylamino group, propylamino group, isopropylamino group, butylamino group, isobutylamino group, (sec-butyl)amino group, (tert-butyl) amino group, pentylamino group, isopentylamino group, (tert-pentyl)amino group, hexylamino group, dimethylamino group, diethylamino group, dipropylamino group, diisopropylamino group, dibutylamino group, diisobutylamino group, di(sec-butyl)amino group, di(tert-butyl) amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$^a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen" or "halide," as used herein can be used interchangeably and refer to F, Cl, Br, or I.

The terms "pseudohalide," "pseudohalogen" or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl" as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl" as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl," "heteroaryl," "bicyclic heterocycle," and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl" as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxy" as used herein is represented by the formula —OH.

The term "ketone" as used herein is represented by the formula A$^1$C(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —N$_3$.

The term "nitro" as used herein is represented by the formula —NO$_2$.

The term "nitrile" or "cyano" as used herein is represented by the formula —CN.

The term "silyl" as used herein is represented by the formula —SiA$^1$A$^2$A$^3$, where A$^1$, A$^2$, and A$^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, —S(O)$_2$A$^1$, —OS(O)$_2$A$^1$, or —OS(O)$_2$OA$^1$, where A$^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —S(O)$_2$A$^1$, where A$^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula A'S(O)$_2$A$^2$, where A$^1$ and A$^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A'S(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"R$^1$," "R$^2$," "R$^3$," . . . "R$^e$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —(CH$_2$)$_{0-4}$R$^\circ$; —(CH$_2$)$_{0-4}$OR$^\circ$; —O(CH$_2$)$_{0-4}$R$^\circ$, —O—(CH$_2$)$_{0-4}$(O)OR$^\circ$; —(CH$_2$)$_{0-4}$CH(OR$^\circ$)$_2$; —(CH$_2$)$_{0-4}$SR$^\circ$; —(CH$_2$)$_{0-4}$Ph, which may be substituted with R$^\circ$; —(CH$_2$)$_{0-4}$O(CH$_2$)$_{0-1}$Ph which may be substituted with R$^\circ$; —CH=CHPh, which may be substituted with R$^\circ$; —(CH$_2$)$_{0-4}$O(CH$_2$)$_{0-1}$-pyridyl which may be substituted with R$^\circ$; —NO$_2$; —CN; —N$_3$; —(CH$_2$)$_{0-4}$N(R$^\circ$)$_2$; —(CH$_2$)$_{0-4}$N(R$^\circ$)C(O)R$^\circ$; —N(R$^\circ$)C(S)R$^\circ$; —(CH$_2$)$_{0-4}$N(R$^\circ$)C(O)NR$^\circ{}_2$; —N(R$^\circ$)C(S)NR$^\circ{}_2$; —(CH$_2$)$_{0-4}$N(R$^\circ$)C(O)OR$^\circ$; —N(R$^\circ$)N(R$^\circ$)C(O)R$^\circ$; —N(R$^\circ$)N(R$^\circ$)C(O)NR$^\circ{}_2$; —N(R$^\circ$)N(R$^\circ$)C(O)OR$^\circ$; —(CH$_2$)$_{0-4}$(O)R$^\circ$; —C(S)R$^{602}$; —(CH$_2$)$_{0-4}$(O)OR$^\circ$; —(CH$_2$)$_{0-4}$(O)SR$^\circ$; —(CH$_2$)$_{0-4}$(O)OSiR$^\circ{}_3$; —(CH$_2$)$_{0-4}$OC(O)R$^\circ$; —OC(O)(CH$_2$)$_{0-4}$SR—, SC(S)SR$^\circ$; —(CH$_2$)$_{0-4}$SC(O)R$^\circ$; —(CH$_2$)$_{0-4}$(O)NR$^\circ{}_2$; —C(S)NR$^\circ{}_2$; —C(S)SR$^\circ$; —(CH$_2$)$_{0-4}$OC(O)NR$^\circ{}_2$; —C(O)N(OR$^\circ$)R$^\circ$; —C(O)C(O)R$^\circ$; —C(O)CH$_2$C(O)R$^\circ$; —C(NOR$^\circ$)R$^\circ$; —(CH$_2$)$_{0-4}$SSR$^\circ$; —(CH$_2$)$_{0-4}$S(O)$_2$R$^\circ$; —(CH$_2$)$_{0-4}$S(O)$_2$OR$^\circ$; —(CH$_2$)$_{0-4}$OS(O)$_2$R$^\circ$; —S(O)$_2$NR$^\circ{}_2$; —(CH$_2$)$_{0-4}$S(O)R$^\circ$; —N(R$^\circ$)S(O)$_2$NR$^\circ{}_2$; —N(R$^\circ$)S(O)$_2$R$^\circ$; —N(OR$^\circ$)R$^\circ$; —C(NH)NR$^\circ{}_2$; —P(O)$_2$R$^\circ$; —P(O)R$^\circ{}_2$; —OP(O)R$^\circ{}_2$; —OP(O)(OR$^\circ$)$_2$; SiR$^\circ{}_3$; —(C$_{1-4}$ straight or branched alkylene)O—N(R$^\circ$)$_2$; or —(C$_{1-4}$ straight or branched)alkylene)C(O)O—N(R$^\circ$)$_2$, wherein each R$^\circ$ may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R$^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R$^\circ$ (or the ring formed by taking two independent occurrences of R$^\circ$ together with their intervening atoms), are independently halogen, —(CH$_2$)$_{0-2}$R$^\bullet$,-(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet{}_2$, —NO$_2$, —SiR$^\bullet{}_3$, —OSiR$^\bullet{}_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R$^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R●, -(haloR●), —OH, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

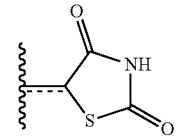

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or L meaning that the compound is levorotatory. A compound prefixed with (+) or D is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-lngold-Prelog system can be used to assign the (R) or (S) configuration to a chiral carbon.

It is also appreciated that certain compounds described herein can be present as an equilibrium of tautomers. For example, ketones with an α-hydrogen can exist in an equilibrium of the keto form and the enol form.

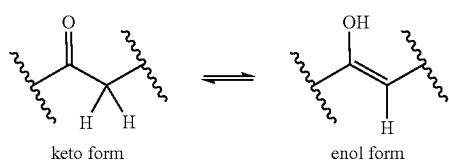

keto form    enol form

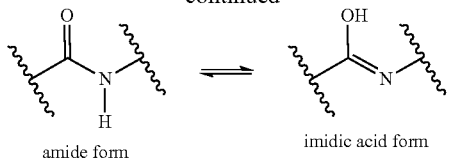

amide form    imidic acid form

Likewise, amides with an N-hydrogen can exist in an equilibrium of the amide form and the imidic acid form. Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

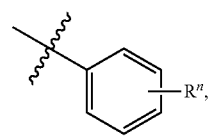

which is understood to be equivalent to a formula:

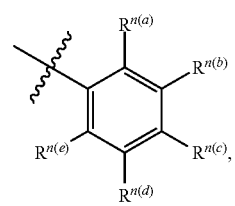

wherein n is typically an integer. That is, $R^n$ is understood to represent five independent substituents, $R^{n(a)}$, $R^{n(b)}$, $R^{n(c)}$, $R^{n(d)}$, and $R^{n(e)}$. By "independent substituents," it is meant that each R substituent can be independently defined. For example, if in one instance $R^{n(a)}$ is halogen, then $R^{n(b)}$ is not necessarily halogen in that instance.

The squiggle line placed on the bonds in the structures provided herein represents a bond to another group. For example, in the structure below

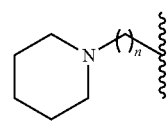

the squiggle line through the bond indicates that another group (e.g., O—O—R) is bonded to the structure above.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wisconsin), Acros Organics (Morris Plains, New Jersey), Fisher Scientific (Pittsburgh, Pennsylvania), or Sigma (St. Louis, Missouri) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); Larock's Comprehensive Organic Transformations (VCH Publishers Inc., 1989); Encyclopedia of Reagents for Organic Synthesis, Volumes 1-14 (John Wiley and Sons, 2009, $2^{nd}$ ed); and Comprehensive Organic Synthesis, Volumes 1-9 (Elsevier, 2014, $2^{nd}$ ed).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

In various aspects, the disclosed compounds can possess at least one center of asymmetry, they can be present in the form of their racemates, in the form of the pure enantiomers and/or diastereomers or in the form of mixtures of these enantiomers and/or diastereomers. The stereoisomers can be present in the mixtures in any arbitrary proportions. In some aspects, provided this is possible, the disclosed compounds can be present in the form of the tautomers.

Thus, methods which are known per se can be used, for example, to separate the disclosed compounds which possess one or more chiral centers and occur as racemates into their optical isomers, i.e., enantiomers or diastereomers. The separation can be effected by means of column separation on chiral phases or by means of recrystallization from an optically active solvent or using an optically active acid or base or by means of derivatizing with an optically active reagent, such as an optically active alcohol, and subsequently cleaving off the residue.

Unless otherwise specified, temperatures referred to herein are based on atmospheric pressure (i.e. one atmosphere).

Methods for Direct Construction of N,N,O-Trisubstituted Hydroxylamines

In one aspect, provided herein is a method for the direct construction of N,N,O-trisubstituted hydroxylamines by combining a convenient electrophilic source of $RO^+$ with secondary amines that lacks the inherent limitations of known methods. In another aspect, the reaction of alkyllithiums with tetrahydropyranyl (THP) monoperoxy acetals resulting in the formation of ethers (FIG. 3A) and applied to the synthesis of 2-deoxyglycosides by oxidation and subsequent reaction with 2-methyl tetrahydropyranyl (MTHP) monoperoxy acetals of anomeric anions (FIG. 3B) can serve as a model for the disclosed reactions. In a further aspect, MTHP monoperoxy acetals can be easily prepared through either $S_N1$ or $S_N2$ pathways from the corresponding TTHP hydroperoxide. In another aspect, reaction of dialkylamides with MTHP monoperoxy acetals as disclosed herein directly affords a wide variety of N,N,O-trisubstituted hydroxylamines (FIG. 3C).

In one aspect, disclosed herein is a method for producing a trisubstituted hydroxylamine, the method including the step of reacting a monoperoxyacetal compound with a secondary amide. In some aspects, the monoperoxyacetal compound can be a cycloalkyl compound or heterocycloalkyl compound substituted with a peroxyacetal group.

In another aspect, also disclosed herein is a method for the preparation of N,N,O-trisubstituted hydroxylamines by direct N—O bond formation, thereby enabling further investigation of the hydroxalog concept as a tool in medicinal chemistry. In one aspect, provided herein is a novel method for the construction of N,N,O-trisubstituted hydroxylamines, whereby magnesium amides react with methyltetrahydro-2H-pyran (MTH P) monoperoxyacetals affording N,N,O-trisubstituted hydroxylamines in good to excellent yields with broad functional group tolerance. In another aspect, this method is applicable to a wide array of primary and secondary alcohol-derived N,N,O-trisubstituted hydroxylamines, but failed under standard conditions when applied to the tert-butyl derived MTHP (Scheme 1).

Scheme 1. Reactions of MTHP peroxides with magnesium amides.

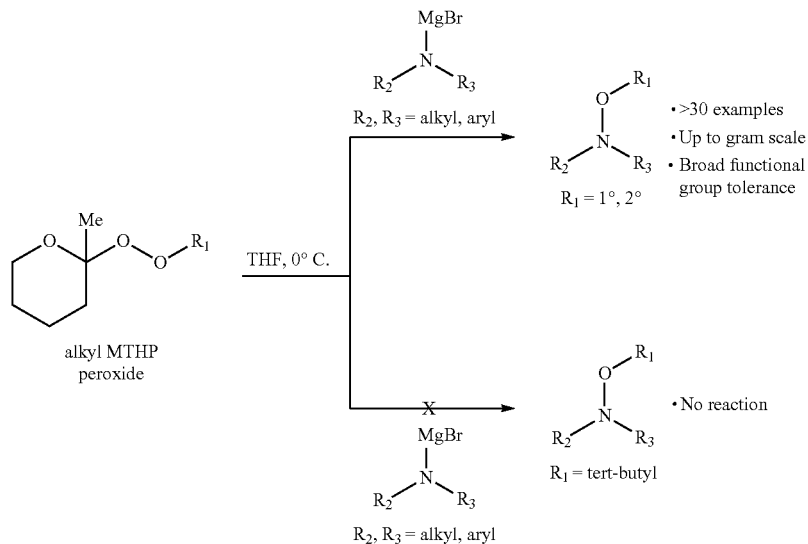

In one aspect, the tert-butyl group is a commonly encountered motif in medicinal and agrochemistry (Scheme 2).

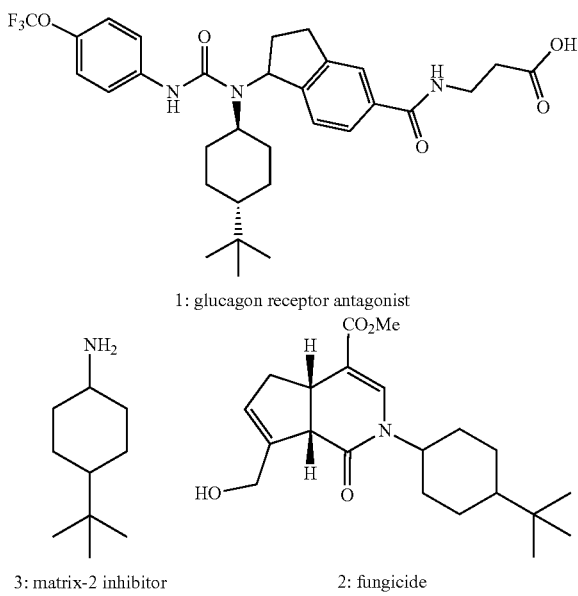

Scheme 2 Examples of the tert-butyl group in medicinal and agrochemistry.

Figure 7:
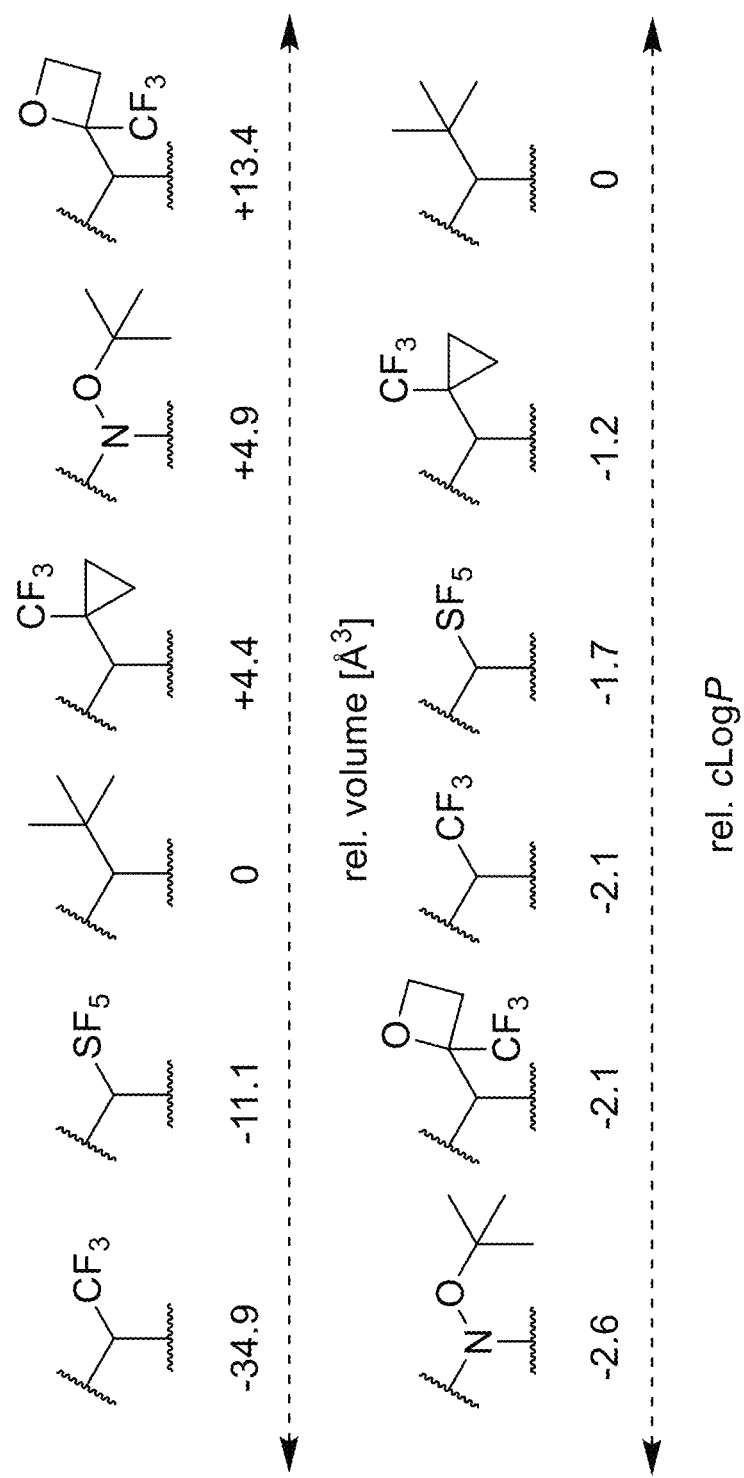
FIG. 7 shows relative volumes and c Log P of tert-butyl isosteres.

In another aspect, as a result of frequently limited metabolic stability, which often correlates with increased lipophilicity (log P, log D), considerable effort has been devoted to exploring novel bioisosteres of tert-butyl groups for drug discovery programs. In a further aspect, several bioisosteric replacements of tert-butyl groups have been investigated over the years including the trifluoromethyl ($CF_3$), pentafluorosulfanyl ($SF_5$), cyclopropyl-trifluoromethyl (cyclopropyl-$CF_3$), and trifluoromethyl oxetaneyl (FIG. 7).

In one aspect, the N,N,O-trialkylhydroxylamine unit as an under-represented functional group in medicinal chemistry suitable for the bioisosteric replacement of ether and branched alkyl units in natural products (FIG. 1). In another aspect, this concept has been previously applied to the synthesis of a hydroxalog (hydroxylamine-analog) of the β-(1→3)-glucan laminaritriose, which showed improved biological activity compared to the parent trisaccharide. In another aspect, the hydroxalog concept has been applied to the synthesis of a potent anticancer derivative: 10-aza-9-oxakalkitoxin ($IC_{50}$: 2.4 ng/mL), the first example of a kalkitoxin analog with activity comparable or better than the parent compound ($IC_{50}$: 3.2 ng/mL) against the human hepatocarcinoma cell line HepG2.

In one aspect, the bioisosteric replacement of tert-butyl groups by N,N,O-trisubstituted hydroxylamines is supported by several factors. In a further aspect, according to a simple web-based calculation from molinspiration previously employed by Carreira while investigating tert-butyl isosteres, the O-tert-butyl-N,N-disubstituted hydroxylamine ($\Delta V=+4.9$ Å$^3$) closely resembles the parent tert-butyl and the commonly employed cyclopropyl-$CF_3$ bioisostere ($\Delta V=+4.4$ Å$^3$). In a still further aspect, replacement of the lipophilic tert-butyl group by a substantially more polar N,N,O-trisubstituted hydroxylamine unit is predicted to result in a 2.6 c Log P unit decrease, a tactic widely employed in medicinal chemistry as a means of increasing metabolic stability and aqueous solubility and reducing off-target responses.

In one aspect, previous syntheses of O-tert-butyl-N,N-disubstituted hydroxylamines are mainly limited to solvolysis of tert-butanol with N-hydroxyphthalimide, which is adequate for the installation of the tert-butoxy portion, but requires multiple steps for further derivatization of the amino-portion. Disclosed herein is a general method for the direct construction of a wide array of O-tert-butyl-N,N-disubstituted hydroxylamines by direct N—O bond formation employing an easily accessible "OR$^+$" reagent. In one aspect, in an early report on ether formation by Lawesson and Yang, the reaction of Grignard and alkyllithium reagents with tert-butyl peroxybenzoate (TBPB) afforded O-tert-butyl ethers in good yields (FIG. 8A). In one aspect, this method seemed particularly attractive, since TBPB is commercially available and is widely employed in oxidation chemistry. Further in this aspect, derivatives can be easily accessed by standard acylation chemistry.

In one aspect, nucleophilic addition to perester electrophiles can occur through two different pathways: i) 1,2-addition at the carbonyl group or ii) 1,4-addition to the peroxy oxygen (Scheme 3). In another aspect, previously reported studies on the nucleophilic addition of amines to TBPB has demonstrated that C-attack (1,2-addition) predominates over the corresponding O-attack (1,4-addition).

Scheme 3. Potential outcomes of nucleophilic addition to perester electrophiles.

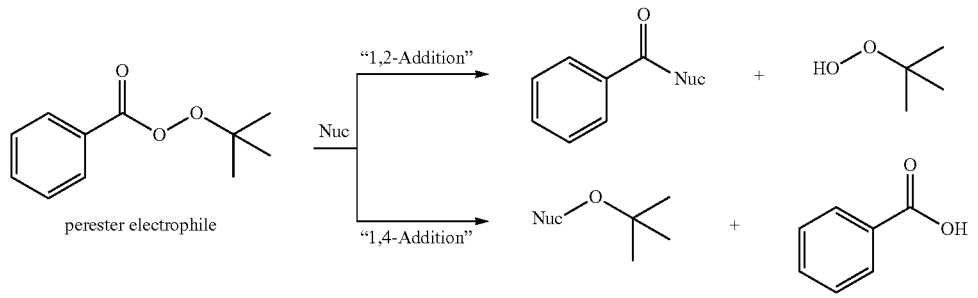

In one aspect, a mild benzoylation procedure wherein amines react chemoselectively with TBPB to afford benzamides in high yields has been reported (FIG. 8B). In another aspect, under basic conditions, formamides decarbonylate and react selectively with TBPB affording the benzamides in good to excellent yields (FIG. 8C). In an alternative aspect, an early report showed that sterically encumbered primary tert-alkyl lithium amides react with TBPB to afford O-tert-butyl-N-monosubstituted hydroxylamines by direct N—O bond formation in modest yields (FIG. 8D). In another aspect, however, yields were modest at best and extremely sensitive to the steric nature of the nucleophile. In one aspect, disclosed herein is a reaction of magnesium dialkylamides with an appropriately substituted TBPB derivative that offers a practical method to access a wide array of O-tert-butyl-N,N-disubstituted hydroxylamines in a direct fashion by N—O bond formation without the inherent scope limitations previously observed (FIG. 8E).

In another aspect, the peroxyacetal group has the formula —O—O—$R^1$, wherein $R^1$ can be a substituted or unsubstituted linear or branched alkyl group, a substituted or unsubstituted cycloalkyl group or heterocycloalkyl group, a polyether group, an alkylpolyether group, or a protected monosaccharide, disaccharide, or polysaccharide, or any combination thereof. In some aspects, when $R^1$ is a substituted alkyl group, it can be

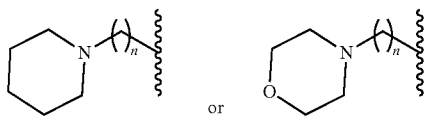

and n can be from 1 to 5, or can be 1, 2, 3, 4, or 5.

In another aspect, the monoperoxyacetal compound can be a tetrahydropyranyl compound substituted with a per-oxyacetal group. In another aspect, the monoperoxyacetal compound can have structure I or II:

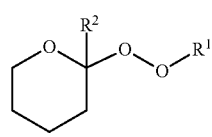

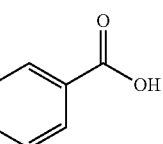

wherein $R^1$ can be a substituted or unsubstituted linear or branched alkyl group, a substituted or unsubstituted cycloalkyl group or heterocycloalkyl group, a polyether group, an alkylpolyether group, or a protected monosaccharide, disaccharide, or polysaccharide and $R^2$ can be hydrogen, an aryl group, a heteroaryl group, or a substituted or unsubstituted alkyl group. In any of these aspects, $R^1$ can be 1-piperidinylethyl or 1-morpholinoethyl or a combination thereof. In some aspects, $R^1$ can be

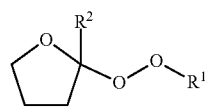

In still another aspect, $R^1$ can be tert-butyl. In another aspect, $R^2$ can be methyl or phenyl. In one aspect, the monoperoxyacetal compound has structure I and $R^2$ is methyl.

In another aspect, the monoperoxyacetal compound can have the structure III:

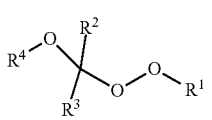

wherein $R^1$ can be a substituted or unsubstituted linear or branched alkyl group, a substituted or unsubstituted cycloalkyl group or heterocycloalkyl group, a polyether group, an alkylpolyether group, or a protected monosaccharide, disaccharide, or polysaccharide; and $R^2$, $R^3$, and $R^4$ can be, independently, hydrogen, a substituted or unsubstituted aryl group, a substituted or unsubstituted heteroaryl group, or a substituted or unsubstituted alkyl group. In some aspects, $R^3$ and $R^4$ together form a substituted or unsubstituted cycloalkyl group or heterocycloalkyl group.

In another aspect, the secondary amide can have the structure IV:

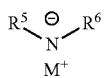

IV wherein $R^5$ and $R^6$ can be, independently, a substituted or unsubstituted alkyl group, a substituted or unsubstituted cycloalkyl group or heterocycloalkyl group, a substituted or unsubstituted aryl group, or a substituted or unsubstituted heteroaryl group, and $M^+$ can be Li, Na, K, MgBr, MgCl, or MgI. In one aspect, $R^5$ and $R^6$ can both be benzyl, phenyl, or ethyl, or $R^5$ can be phenyl and $R^6$ can be 4-chlorophenyl, or $R^5$ can be methyl and $R^6$ can be phenyl, or $R^5$ and $R^6$ together form a substituted or unsubstituted piperidine, piperazine, pyrrolidine, morpholine, indoline, or 1,2,3,4-tetrahydroquinoline ring system. In some aspects, $R^5$ and $R^6$ together form a substituted or unsubstituted cycloalkyl group or heterocycloalkyl group.

In another aspect, disclosed herein is a method for producing a hydroxylamine, the method including the steps of reacting a peroxybenzoate compound with a secondary amide. In another aspect, the peroxybenzoate compound is a compound of formula VI:

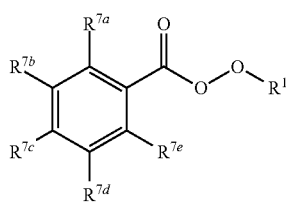

III wherein $R^1$ is a tertiary alkyl group such as, for example, a tert-butyl group, a substituted or unsubstituted tertiary cycloalkyl group or tertiary heterocycloalkyl group, a tertiary polyether group, a tertiary alkylpolyether group, or a protected tertiary monosaccharide, tertiary disaccharide, or tertiary polysaccharide and wherein $R^{7a}$, $R^{7b}$, $R^{7c}$, $R^{7d}$, and $R^{7e}$ are, independently, hydrogen or a substituted or unsubstituted linear or branched alkyl group.

In another aspect, the peroxybenzoate compound has the structure:

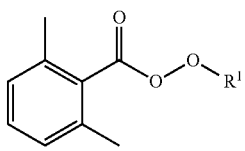

In still another aspect, the peroxybenzoate compound has the structure:

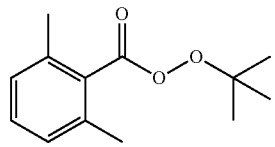 [SMILES: Cc1cccc(C)c1C(=O)OOC(C)(C)C]

In one aspect, in the peroxybenzoate compound, $R^1$ can be tertiary alkyl such as, for example, tert-butyl.

In any of these aspects, the secondary amide can be produced by reacting a secondary amine with a Grignard agent. In one aspect, the secondary amine is an alkaloid or is derived from an alkaloid. In another aspect, the alkaloid can be a natural product including, but not limited to, coniine, cytisine, pipecolic acid, nornicotine, anabasine, pavine, febrifugine, strictosidine, tryptamine, serotonin, psilocybin, N,N-dimethyltryptamine, bufotenine, harmine, harmaline, lysergic acid, ergotamine, yohimbine, reserpine, mitragynine, ibogamine, ibogaine, voacangine, theobromine, saxitoxin, ephedrine, pseudoephedrine, epinephrine, colchicine, capsaicin, dihydrocapsaicin, phenylephrine, a combination thereof, or a semisynthetic derivative thereof.

In one aspect, the Grignard agent is an alkyl Grignard agent. In any of these aspects, in the method disclosed herein, the molar ratio of monoperoxyacetal compound to secondary amide is from about 1:1 to about 1:5, or is about 1:1, 1:1.5, 1:2, 1:2.5, 1:3, 1:3.5, 1:4, 1:4.5, or about 1:5, or a combination of any of the foregoing values, or a range encompassing any of the foregoing values.

In one aspect, the Grignard agent is an alkyl Grignard agent. In any of these aspects, in the method disclosed herein, the molar ratio of peroxybenzoate compound to secondary amide is from about 1:1 to about 1:5, or is about 1:1, 1:1.5, 1:2, 1:2.5, 1:3, 1:3.5, 1:4, 1:4.5, or about 1:5, or a combination of any of the foregoing values, or a range encompassing any of the foregoing values.

In another aspect, in the method disclosed herein, the monoperoxyacetal compound or peroxybenzoate compound and the secondary amide are reacted at a temperature of from about $-10°$ C. to about $25°$ C., or at about $-10, -5, 0, 5, 10, 15, 20$, or about $25°$ C., or a combination of any of the foregoing values, or a range encompassing any of the foregoing values.

In another aspect, the monoperoxyacetal compound or peroxybenzoate compound and the secondary amide are reacted in an organic solvent. In another aspect, the organic solvent can be tetrahydrofuran (THF), 2-methyltetrahydrofuran (2-methyl THF), diethyl ether, methyl tert-butyl ether (MTBE), 1,4-dioxane, 1,2-dimethoxyethane, pentane, hexanes, heptanes, cyclohexanes, N,N'-dimethylpropyleneurea (DMPU), or a combination thereof.

Also disclosed herein are trisubstituted hydroxylamines produced by the methods disclosed herein. In one aspect, the trisubstituted hydroxylamine has the structure V:

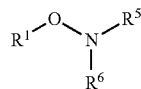

V wherein $R^1$ can be a substituted or unsubstituted linear or branched alkyl group, a substituted or unsubstituted cycloalkyl group or heterocycloalkyl group, a polyether group, an alkylpolyether group, or a protected or unprotected monosaccharide, disaccharide, or polysaccharide; and $R^5$ and $R^6$ can be, independently, a substituted or unsubstituted alkyl group, a substituted or unsubstituted cycloalkyl group or heterocycloalkyl group, a substituted or unsubstituted aryl group, or a substituted or unsubstituted heteroaryl group. In one aspect, $R^5$ and $R^6$ can be selected from, independently, an unsubstituted alkyl group, a substituted or unsubstituted aryl group, a substituted or unsubstituted heteroaryl group, or a combination thereof. In another aspect, $R^5$ and $R^6$ can be part of a cycloalkyl group or heterocycloalkyl group or can together form a substituted or unsubstituted cycloalkyl group or heterocycloalkyl group.

In some aspects, $R^1$ can be a tert-butyl group or another tertiary alkyl group.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

ASPECTS

The present disclosure can be described in accordance with the following numbered Aspects, which should not be confused with the claims.

Aspect 1. A method for producing a trisubstituted hydroxylamine, the method comprising reacting a monoperoxyacetal compound with a secondary amide.

Aspect 2. The method of aspect 1, wherein the monoperoxyacetal compound is a cycloalkyl compound or heterocycloalkyl compound substituted with a peroxyacetal group.

Aspect 3. The method of aspect 1 or 2, wherein the peroxyacetal group has the formula —O—O—$R^1$, wherein $R^1$ is a substituted or unsubstituted linear or branched alkyl group, a substituted or unsubstituted cycloalkyl group or heterocycloalkyl group, a polyether group, an alkylpolyether group, or a protected or unprotected monosaccharide, disaccharide, or polysaccharide.

Aspect 4. The method of aspect 3, wherein the substituted alkyl group comprises:

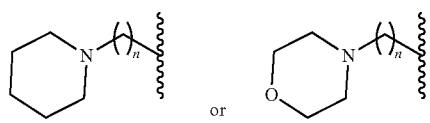

and wherein n is from 1 to 5.

Aspect 5. The method in any one of aspects 1 to 4, wherein the monoperoxyacetal compound is a tetrahydropyranyl compound substituted with a peroxyacetal group.

Aspect 6. The method in any one of aspects 1 to 5, wherein the monoperoxyacetal compound has the structure I or II

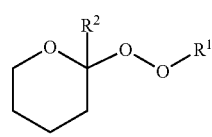

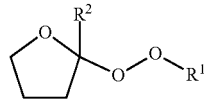

wherein
$R^1$ is a substituted or unsubstituted linear or branched alkyl group, a substituted or unsubstituted cycloalkyl group or heterocycloalkyl group, a polyether group, an alkylpolyether group, or a protected or unprotected monosaccharide, disaccharide, or polysaccharide, and
$R^2$ is hydrogen, an aryl group, a heteroaryl group, or a substituted or unsubstituted alkyl group.

Aspect 7. The method of aspect 6, wherein $R^1$ is 1-piperidinylethyl or 1-morpholinoethyl.

Aspect 8. The method of aspect 6, wherein $R^1$ is

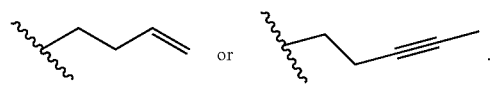

Aspect 9. The method of aspect 6, wherein $R^2$ is methyl or phenyl.

Aspect 10. The method of aspect 6, wherein the structure is I and $R^2$ is methyl.

Aspect 11. The method in any one of aspects 1 to 5, wherein the monoperoxyacetal compound has the structure III

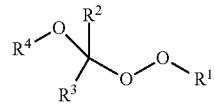

wherein
$R^1$ is a substituted or unsubstituted linear or branched alkyl group, a substituted or unsubstituted cycloalkyl group or heterocycloalkyl group, a polyether group, an alkylpolyether group, or a protected monosaccharide, disaccharide, or polysaccharide; and
$R^2$, $R^3$, and $R^4$ are, independently, hydrogen, a substituted or unsubstituted aryl group, a substituted or unsubstituted heteroaryl group, or a substituted or unsubstituted alkyl group, or wherein $R^3$ and $R^4$ together form a substituted or unsubstituted cycloalkyl group or heterocycloalkyl group.

Aspect 12. The method in any one of aspects 1 to 11, wherein the secondary amide has the structure IV

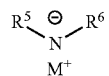

wherein
$R^5$ and $R^6$ are, independently, a substituted or unsubstituted alkyl group, a substituted or unsubstituted cycloalkyl group or heterocycloalkyl group, a substituted or unsubstituted aryl group, or a substituted or unsubstituted heteroaryl group, or wherein $R^5$ and $R^6$ together form a substituted or unsubstituted cycloalkyl group or heterocycloalkyl group, and wherein M⁺ is Li, Na, K, MgBr, MgCl, or MgI.

Aspect 13. The method of aspect 12, wherein $R^5$ and $R^6$ are both benzyl, phenyl, or ethyl, or wherein $R^5$ is phenyl and $R^6$ is 4-chlorophenyl, or wherein $R^5$ is methyl and $R^6$ is phenyl, or wherein $R^5$ and $R^6$ together form a substituted or unsubstituted piperidine, piperazine, pyrrolidine, morpholine, indoline, or 1,2,3,4-tetrahydroquinoline ring system.

Aspect 14. The method in any one of aspects 1 to 13, wherein the secondary amide is produced by reacting a secondary amine with a Grignard agent.

Aspect 15. The method of aspect 14, wherein the secondary amine is an alkaloid or is derived from an alkaloid.

Aspect 16. The method of aspect 14 or 15, wherein the Grignard agent is an alkyl Grignard agent.

Aspect 17. The method in any one of aspects 1 to 16, wherein the molar ratio of monoperoxyacetal compound to the secondary amide is from 1:1 to 1:5.

Aspect 18. The method in any one of aspects 1 to 17, wherein the monoperoxyacetal compound and the secondary amide are reacted at a temperature of from about −10° C. to about 25° C.

Aspect 19. The method in any one of aspects 1 to 18, wherein the monoperoxyacetal compound and the secondary amide are in an organic solvent.

Aspect 20. The method of aspect 19, wherein the organic solvent comprises tetrahydrofuran (THF), 2-methyltetrahydrofuran (2-methyl THF), diethyl ether, methyl tert-butyl ether (MTBE), 1,4-dioxane, 1,2-dimethoxyethane, pentane, hexanes, heptanes, cyclohexanes, N,N'-dimethylpropyleneurea (DMPU), or a combination thereof.

Aspect 21. A trisubstituted hydroxylamine produced by the method in any one of aspects 1 to 20.

Aspect 22. A method for producing a trisubstituted hydroxylamine, the method comprising reacting a peroxybenzoate compound with a secondary amide.

Aspect 23. The method of aspect 22, wherein the peroxybenzoate compound is a compound of formula VI,

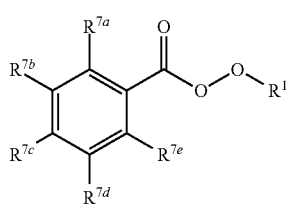

III wherein $R^1$ is a tertiary alkyl group, a substituted or unsubstituted tertiary cycloalkyl group or tertiary heterocycloalkyl group, a tertiary polyether group, a tertiary alkylpolyether group, or a protected tertiary monosaccharide, tertiary disaccharide, or tertiary polysaccharide; and wherein $R^{7a}$, $R^{7b}$, $R^{7c}$, $R^{7d}$, and $R^{7e}$ are, independently, hydrogen or a substituted or unsubstituted linear or branched alkyl group.

Aspect 24. The method of aspect 23, wherein the peroxybenzoate compound has the structure

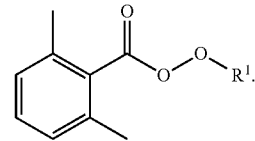

Aspect 25. The method of aspect 23, wherein the peroxybenzoate compound has the structure

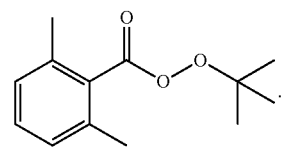 [SMILES: Cc1cccc(C)c1C(=O)OOC(C)(C)C]

Aspect 26. The method of aspect 23, wherein $R^1$ is tert-butyl.

Aspect 27. The method in any one of aspects 23 to 26, wherein the secondary amide has the structure IV

IV wherein $R^5$ and $R^6$ are, independently, a substituted or unsubstituted alkyl group, a substituted or unsubstituted cycloalkyl group or heterocycloalkyl group, a substituted or unsubstituted aryl group, or a substituted or unsubstituted heteroaryl group, or wherein $R^5$ and $R^6$ together form a substituted or unsubstituted cycloalkyl group or heterocycloalkyl group, and M⁺ is Li, Na, K, MgBr, MgCl, or MgI.

Aspect 28. The method of aspect 27, wherein $R^5$ and $R^6$ are both benzyl, phenyl, or ethyl, or wherein $R^5$ is phenyl and $R^6$ is 4-chlorophenyl, or wherein $R^5$ is methyl and $R^6$ is phenyl, or wherein $R^5$ and $R^6$ together form a substituted or unsubstituted piperidine, piperazine, pyrrolidine, morpholine, indoline, or 1,2,3,4-tetrahydroquinoline ring system.

Aspect 29. The method in any one of aspects 23 to 28, wherein the secondary amide is produced by reacting a secondary amine with a Grignard agent.

Aspect 30. The method of aspect 29, wherein the secondary amine is an alkaloid or is derived from an alkaloid.

Aspect 31. The method of aspect 29 or 30, wherein the Grignard agent is an alkyl Grignard agent.

Aspect 32. The method in any one of aspects 23 to 31, wherein the molar ratio of peroxybenzoate compound to the secondary amide is from 1:1 to 1:5.

Aspect 33. The method in any one of aspects 23 to 32, wherein the peroxybenzoate compound and the secondary amide are reacted at a temperature of from about −10° C. to about 25° C.

Aspect 34. The method in any one of aspects 23 to 33, wherein the peroxybenzoate compound and the secondary amide are in an organic solvent.

Aspect 35. The method of aspect 34, wherein the organic solvent comprises tetrahydrofuran (THF), 2-methyltetrahydrofuran (2-methyl THF), diethyl ether, methyl tert-butyl ether (MTBE), 1,4-dioxane, 1,2-dimethoxyethane, pentane, hexanes, heptanes, cyclohexanes, N,N'-dimethylpropyl-eneurea (DMPU), or a combination thereof.

Aspect 36. A trisubstituted hydroxylamine produced by the method in any one of aspects 23 to 35.

Aspect 37. A trisubstituted hydroxylamine having the structure V

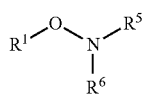

V wherein

R[1] is a substituted or unsubstituted linear or branched alkyl group, a substituted or unsubstituted cycloalkyl group or heterocycloalkyl group, a polyether group, an alkylpolyether group, or a protected or unprotected monosaccharide, disaccharide, or polysaccharide; and R[5] and R[6] are, independently, a substituted or unsubstituted alkyl group, a substituted or unsubstituted cycloalkyl group or heterocycloalkyl group, a substituted or unsubstituted aryl group, or a substituted or unsubstituted heteroaryl group, or wherein R[5] and R[6] together form a substituted or unsubstituted cycloalkyl group or heterocycloalkyl group.

Aspect 38. The trisubstituted hydroxylamine of aspect 37, wherein R[1] is an unsubstituted alkyl group.

Aspect 39. The trisubstituted hydroxylamine of aspect 37, wherein R[1] is a tert-butyl group.

Aspect 40. The trisubstituted hydroxylamine of aspect 37, wherein R[1] is

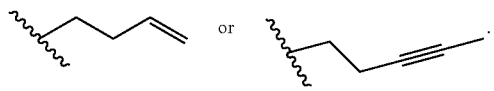

Aspect 41. The trisubstituted hydroxylamine of aspect 37, wherein R[1] is a monosaccharide, a disaccharide, or a polysaccharide.

Aspect 42. The trisubstituted hydroxylamine in any one of aspects 37 to 41, wherein R[5] and R[6] are, independently, an unsubstituted alkyl group, a substituted or unsubstituted cycloalkyl group, a substituted or unsubstituted heterocycloalkyl group, a substituted or unsubstituted aryl group, or a substituted or unsubstituted heteroaryl group.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, equivalents are molar equivalents, temperature is in ° C. or is at ambient temperature, and pressure is at or near atmospheric.

Example 1: General Experimental Conditions

All reactions were conducted in flame/oven dried glassware capped with rubber septa under an atmosphere of argon unless otherwise stated. Commercially available starting materials were used without purification, unless otherwise stated. All organic solutions were concentrated under reduced pressure on a rotary evaporator and water bath.

Flash-column chromatography was performed using silica gel (Fisher Silica Gel Sorbent (230-400 Mesh, Grade 60) or COMBIFLASH® NextGen system, unless otherwise stated. Thin-layer chromatography (TLC) was carried out with 250 μm glass backed silica (XHL) plates with fluorescent indicator (254 nm). TLC plates were visualized by exposure to ultraviolet light (UV) and/or submersion in ceric ammonium molybdate solution (CAM), aqueous potassium permanganate solution ($KMnO_4$), p-anisaldehyde solution in ethanol or 10% sulfuric acid in ethanol followed by heating on a hot plate (120° C., 10-15 s).

Commercial solvents and reagents were used as received without further purification.

Nuclear magnetic resonance (NMR) spectra of all compounds were obtained in $CDCl_3$ (δ 7.26 ppm and 77.16 μm, respectively), DMSO-$d_6$ (δ 2.50 and 39.52 ppm, respectively), or $CD_3OD$ (δ 3.31 and 49.00 ppm, respectively) using a 600 MHz Varian or 500 MHz, EZC500 JEOL instrument. The chemical shifts (δ) are calculated with respect to residual solvent peak and are given in ppm. Multiplicities are abbreviated as follows: s (singlet), m (multiplet), br (broad), d (doublet), t (triplet), q (quartet) and comp (complex). Assignments were made with the help of COSY, HMBC, HSQC and $^{15}$N-HMBC spectra. Specific rotations were recorded in $CHCl_3$, at 589 nm and 21° C. on a digital polarimeter with a path length of 10 cm. High resolution mass spectra were obtained on a ThermoFisher Orbitrap Q-Exactive using electrospray ionization (ESI).

Starting materials 11 and 12 were prepared using previously published procedures.

Example 2: General Procedures for the Synthesis of Starting Materials and Products Preparation of THP and MTHP Hydroperoxides Via Modification of a Published Procedure

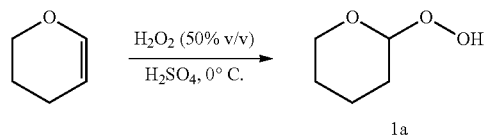 [SMILES: C1=COCCC1 ; OOC1CCCCO1]

1a

To a stirred solution of $H_2O_2$ (50% v/v) (3.8 mL, 58.8 mmol, 2 eq.) at 0° C. was added $H_2SO_4$ (18.4 M, 0.05 mL, 0.92 mmol, 0.01 eq). The solution was stirred for 10 min, after which, 3,4-dihydropyran (2.68 mL, 29.4 mmol, 1 eq.) was added dropwise at 0° C. and the solution was stirred for 1 hr. After such time, the reaction mixture was diluted with $Et_2O$ (15 mL) and quenched by the addition of a saturated solution of $NH_4Cl$ (30 mL). The resulting biphasic mixture was transferred to a separatory funnel and the layers separated. The aqueous layer was extracted with ethyl acetate (5×40 mL) and the organic layers were combined, dried over $Na_2SO_4$, filtered, and concentrated in vacuo. The residue obtained was purified by flash-column chromatography (5:95 EtOAc:hexanes) to obtain the title compound (1a) as a colorless oil (2.04 g, 59%). $R_f$=0.3 (25:75 EtOAc:hexanes; CAM) $^1$H NMR (500 MHz, $CDCl_3$): δ 8.69 (s, 1H), 5.08 (t, J=3.5, 1 Hz, 1H), 4.01-3.93 (m, 1H), 3.64 (m, 1H), 1.81-1.69 (m, 2H), 1.65 (m, 4H). $^{13}$C NMR (126 MHz, $CDCl_3$): δ

102.55, 62.78, 27.42, 25.18, 19.58. HRMS-ESI (m/z): [M+Na]$^+$ calculated for [C$_5$H$_{10}$O$_3$Na]$^+$: 141.0522, found 141.0520.

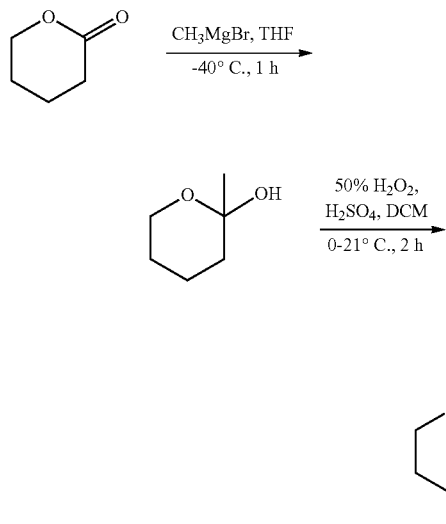

1b

CH$_3$MgCl 3.0 M solution in THF (20 mmol, 6.67 mL, 1.0 eq) was added dropwise over 10 minutes in to a solution of δ-valerolactone (20 mmol, 1.86 mL, 1.0 equiv.) in 40 mL of anhydrous THF at −40° C. under an argon atmosphere. The reaction was stirred for 1 h at −40° C. After consumption of starting material as indicated by TLC and MS, the reaction mixture was bought to −20° C. and quenched with a saturated solution of NH$_4$Cl (40 mL) followed by diluting with DI water (20 mL) at room temperature. The resulting biphasic mixture was separated and the aqueous layer was extracted with ethyl acetate (5×40 mL). The organic layers were combined and dried over Na$_2$SO$_4$, filtered, and concentrated in vacuo. The crude reaction mixture was then used directly in the following step without further purification.

To a stirred solution of 2-methyltetrahydro-2H-pyran-2-ol (2.3 g, 20 mmol, 1 equiv.) obtained in the previous step in 100 mL of DCM was added sulfuric acid (18.4 M, 109 μL, 2.0 mmol, 0.10 equiv.) at 0° C. Aqueous hydrogen peroxide solution (50% w/w, 6.8 mL, 100 mmol, 5.00 equiv.) was then added dropwise over 5 minutes and stirred another 10 min at 0° C. The reaction was bought back to room temperature and stirred for 2 hr. The reaction was quenched with a saturated NH$_4$Cl solution (40 mL) and the resulting biphasic mixture was separated and the aqueous layer was extracted with ethyl acetate (5×40 mL). The combined organic layers were dried over Na$_2$SO$_4$, filtered and concentrated in vacuo. The residue obtained was purified by flash-column chromatography (100:0 DCM-8:92 ether: DCM) to obtain 2-hydroperoxy-2 methyltetrahydro-2H-pyran (1b) as a clear, colorless oil (1.72 g, 65% over 2 steps). R$_f$=0.30 (10% ether/DCM; UV, CAM). $^1$H NMR (600 MHz, CDCl$_3$): δ 7.89 (s, 1H), 3.81 (td, J=11.3, 3.0 Hz, 1H), 3.71 (ddt, J=11.1, 4.4, 2.1 Hz, 1H), 1.80-1.74 (m, 1H), 1.67 (dddd, J=17.2, 10.9, 7.4, 5.6 Hz, 1H), 1.61-1.49 (m, 4H), 1.40 (s, 3H). $^{13}$C NMR (151 MHz, CDCl$_3$): δ 100.04, 59.12, 29.60, 21.74, 20.87, 15.96. HRMS-ESI (m/z): [M+Na]$^+$ calculated for [C$_6$H$_{12}$O$_3$Na]$^+$: 155.0679, found 155.0672.

Example 3: General Procedure a for Synthesis of THP and MTHP Monoperoxyacetals from Simple Alcohols Via Modification of a Published Procedure

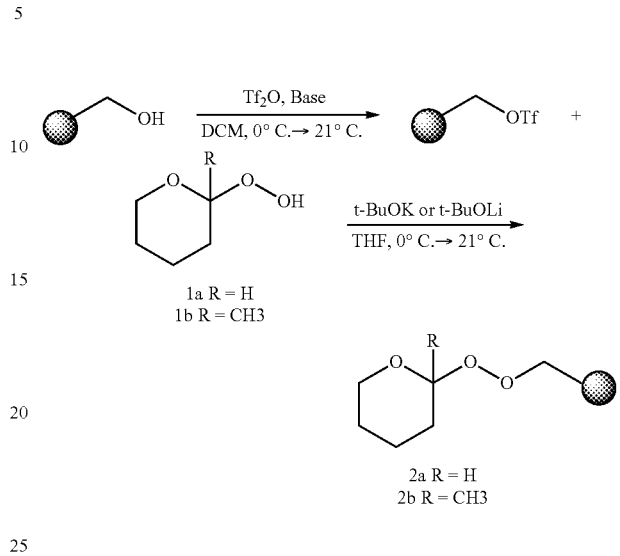

1a R = H
1b R = CH3

2a R = H
2b R = CH3

To an oven dried 100 mL flask was added anhydrous DCM (0.17-0.50 M) alcohol (1.0 eq.) and base (1.5 eq.) under an argon atmosphere at 0° C. The solution was stirred for 10 min, after which, Tf$_2$O (1.2-1.5 eq.) was added dropwise. The solution was stirred for 30 min-1 hr at 0° C. After such time, HCl (10%, 10 mL) was added and the layers were separated. The organic layer was washed with saturated NaHCO$_3$ (1×10 mL) and the aqueous layer was extracted with EtOAc (3×5 mL). The organic layers were then combined and washed with saturated NaCl solution (1×10 mL) and dried over MgSO$_4$, filtered, and concentrated in vacuo. Flash silica column chromatography (eluent: EtOAc/Hexanes) afforded the triflates. A sample of the triflate was then used directly in the following step.

Lithium tert-butoxide or potassium tert-butoxide (1.2-1.5 equiv) was added in a single portion under an argon atmosphere (balloon) to a stirred solution of hydroperoxide (1.5 eq.) in anhydrous THF (0.3-0.5 M). The solution was stirred for 10 min at 0° C., after which, a portion of the triflate (1.0 eq.) obtained in the previous step was added dropwise via syringe. The solution was stirred for 1 hr at 0° C., after which, the mixture was allowed to reach room temperature and stirred for an additional 1-24 hr. The reaction mixture was then quenched with NaHCO$_3$ (20 mL) and diluted with EtOAc (10 mL). The layers were separated and the aqueous layer extracted with EtOAc (3×5 mL). The combined organic layers were then dried over MgSO$_4$/NaSO$_4$, filtered, and concentrated in vacuo. Flash silica column chromatography (EtOAc:hexanes) afforded the title compounds.

Example 4: Synthesis of an MTHP Monoperoxyacetal from Simple Secondary Alcohols Via Modification of Published Procedures

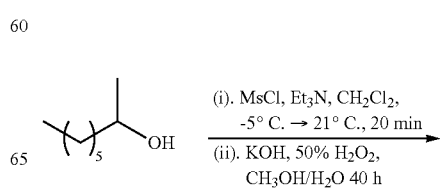

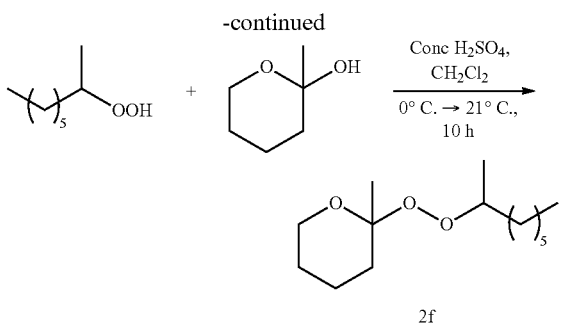

To a solution of 2-octanol (1.00 mL, 6.36 mmol, 3.75 equiv.) and triethylamine (320 μL, 2.3 mmol, 1.3 equiv.) in DCM (8 mL) at −5° C. was added methane sulfonyl chloride (130 μL, 1.7 mmol, 1.0 equiv.) dropwise. The reaction mixture was allowed to warm to room temperature and was stirred for 20 min. The product mixture was diluted with ice water (20 mL) and extracted into 20 mL of diethyl ether. The resulting biphasic mixture was separated and the aqueous phase extracted with diethyl ether (4×20 mL) and the organic layers were combined and washed with ice cold DI water (2×20 mL), 10% aqueous HCl (2×20 mL), and saturated aqueous NaCl solution (2×20 mL). The combined organic layers were dried over $Na_2SO_4$, filtered, and concentrated in vacuo. The residue obtained (355 mg, 1.7 mmol, 1 eq.) was then dissolved in a mixture of $H_2O_2$ (30%, 805 μL, 8.5 mmol, 5.00 equiv.) in methanol (7.0 mL) and water (0.5 mL) at 0° C. To this solution was then added KOH (50% wt/v) (107.2 mg, 1.91 mmol, 1.2 equiv.) and the resulting mixture was bought to room temperature and stirred for 48 hours at 0° C. The reaction mixture was diluted with saturated aqueous $NH_4Cl$ solution (5 mL) and the resulting biphasic mixture was separated and the aqueous layer was extracted with EtOAc (5×10 mL). Combined organic layers were dried over $Na_2SO_4$, filtered, and concentrated in vacuo. The residue obtained was purified by flash-column chromatography (100:0 hexanes:DCM-40:60 hexanes:DCM) to obtain the 2-hydroperoxyoctane as a clear, colorless oil (109 mg, 0.748 mmol, 44%). Spectral data are in accord with that previously reported in the literature. $R_f$=0.83 (10% ether/DCM; CAM) $^1$H NMR (500 MHz, $CDCl_3$): δ 7.81 (s, 1H), 4.04 (q, 1H), 1.61 (m, 1H), 1.43-1.23 (m, 9H), 1.20 (d, J=6.2 Hz, 3H), 0.87 (t, J=6.9 Hz, 3H). $^{13}$C NMR (126 MHz, $CDCl_3$): δ 81.77, 34.1, 31.84, 29.43, 25.49, 22.69, 18.23, 14.13. HRMS-ESI (m/z): [M+Na]+ calculated for $[C_8H_{18}O_2Na]^+$: 169.1204; found: 169.1215.

Concentrated sulfuric acid (18.4 M, 5 μL, 0.034 mmol, 0.1 equiv.) and 2-hydroperoxyoctane solution (0.34 mmol, 50 mg in 0.7 mL anhydrous DCM, 1.0 equiv.) were added in sequence to a solution of 2-methyltetrahydro-2H-pyran-2-ol (39.5 mg, 0.34 mmol, 1.0 equiv.) in anhydrous DCM (1 mL) at 0° C. under argon atmosphere. The reaction mixture was warmed to room temperature over 20 min and the reaction mixture was stirred for 21 hr. The reaction mixture was then quenched with a chilled solution of $NH_4Cl$ (5 mL) and the resulting biphasic mixture was separated. The aqueous layer was extracted with EtOAc (5×5 mL). Combined organic layers were dried over $Na_2SO_4$, filtered, and concentrated in vacuo. The residue obtained was purified by flash-column chromatography (50:50 Hexanes:DCM-40:60 Hexanes:DCM) to afford MTHP monoperoxy acetal 2f as a colorless oil (58.1 mg, 0.24 mmol, 70%). The MTHP monoperoxy acetal 2f was obtained as a 1:1 ratio of diastereomers. Where doubling of $^1$H and $^{13}$C resonances was observed, one signal is reported. $R_f$=0.5 (DCM; CAM) $^1$H NMR (500 MHz, $CDCl_3$): δ 4.09 (dp, J=12.3, 6.2 Hz, 1H), 3.91 (tt, J=11.6, 2.8 Hz, 1H), 3.72-3.64 (m, 1H), 1.82-1.42 (m, 7H), 1.41 (s, 3H), 1.41-1.22 (m, 9H), 1.21 (d, J=6.2 Hz, 3H), 0.87 (t, J=6.5 Hz, 3H). $^{13}$C NMR (126 MHz, $CDCl_3$): δ 101.89, 79.93, 61.70, 34.78, 33.57, 31.94, 29.53, 25.65, 25.04, 24.85, 22.76, 19.29, 18.93, 14.22. HRMS-ESI (m/z): [M+Na]+ calculated for $[C_{14}H_{28}O_3Na]^+$: 267.1931; found: 267.1929.

Example 5: General Procedure B for Synthesis of MTHP Monoperoxyacetals from Complex Alcohols Via Modification of a Literature Procedure

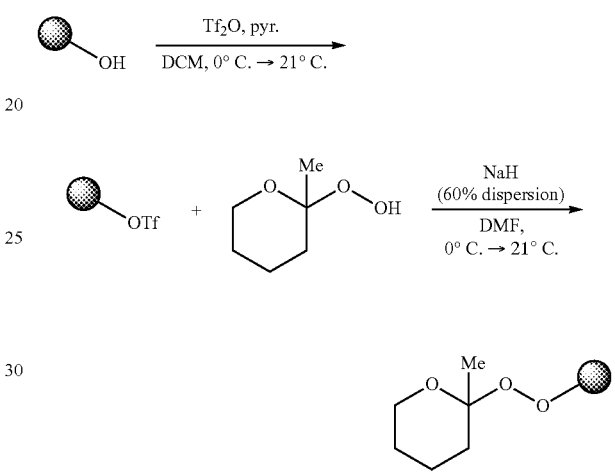

To an oven dried 100 mL flask was added anhydrous DCM (0.13-0.50 M) alcohol (1.0 eq.) and pyridine (2.0 eq.) under an argon atmosphere at 0° C. The solution was stirred for 10 min, after which, $Tf_2O$ (1.2-1.5 eq.) was added dropwise. The solution was stirred for 30 min-1 hr at 0° C. after which the solution was diluted with a few drops of MeOH and HCl (10%, 10 mL). The layers were separated and the organic layer washed with saturated $NaHCO_3$ (1×10 mL). The aqueous layer was extracted with EtOAc (3×5 mL). The combined organics were then washed with saturated NaCl solution (1×10 mL and dried over $MgSO_4$, filtered, and concentrated in vacuo. Flash silica column chromatography (eluent: EtOAc/hexanes) afforded the triflates. A sample of the triflate was then used directly in the following step.

NaH (60% dispersion in mineral oil) (1.2-1.5 eq.) was added in a single portion under an argon atmosphere to a stirred solution of MTHP hydroperoxide (1.0 eq.) in anhydrous DMF (0.3 M). The solution was stirred for 10 min at 0° C., after which the triflate (1.3 eq.) obtained in the previous step was added dropwise via syringe. The solution was stirred for 1 hr, after which the mixture was allowed to reach room temperature and stirred for an additional 1-16 hr. The reaction mixture was then diluted with EtOAc (10 mL) and quenched with saturated $NaHCO_3$ (10 mL). The layers were separated and the aqueous layer extracted with EtOAc (3×5 mL). The combined organic layers were then dried over $MgSO_4$, filtered, and concentrated in vacuo. Flash silica column chromatography (EtOAc:hexanes) afforded the title compound.

Example 6: General Procedure C for Synthesis of N,N,O-Trisubstituted Hydroxylamines Via N—O Bond Formation

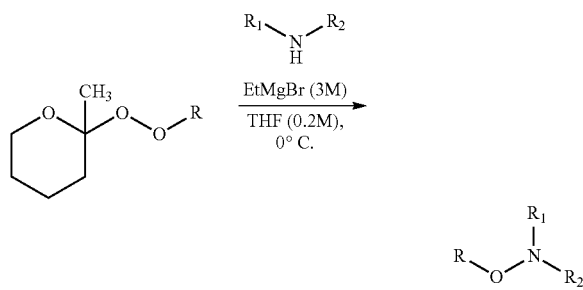

To an oven/flame dried 10 mL flask was added amine (0.25-0.50 mmol, 2.5 eq.) and 0.25-0.50 mL anhydrous THF at 0° C. under an argon atmosphere. To this solution was then added EtMgBr (3M in diethyl ether) (0.20-0.40 mmol, 2.0 eq.) dropwise over 5 min and the reaction mixture was stirred for 10 min at 0° C. After such time, the magnesium amide was transferred via syringe to a stirred solution of the THP (2a) or MTHP (2b) monoperoxyacetal (0.10-0.20 mmol, 1.0 eq.) stirred in an additional 0.25-0.50 mL anhydrous THF (0.2 M total) under an argon atmosphere at 0° C. The solution was stirred for 15 min-3 hr until the starting material had been consumed as indicated by TLC and MS, after which, the mixture was quenched by the addition of chilled water (1 mL) and the layers separated. The aqueous layer was extracted with EtOAc (4×5 mL) and the combined organics were dried over MgSO$_4$/Na$_2$SO$_4$, filtered, and concentrated in vacuo. Flash silica column chromatography (EtOAc:Hexanes or DCM:EtOAc) afforded the title compounds.

Example 7: Synthesis and Characterization of Substrates

2-Tetrahydropyranyl monoperoxyacetal (2a)

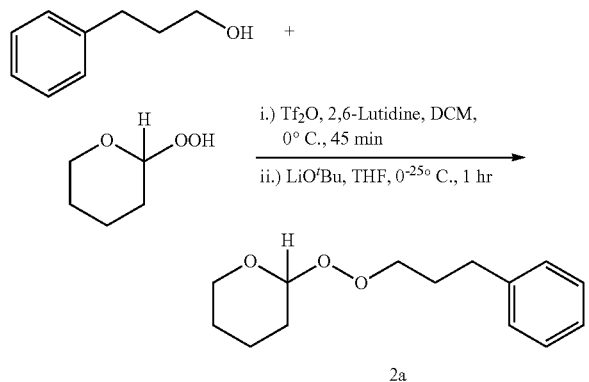

The reaction was performed following GP-A with 3-phenylpropanol (1.5 mL, 11.5 mmol, 1.2 eq.), 2,6-luitidine (2 mL, 17.25 mmol, 1.5 eq.) and Tf$_2$O (2.3 mL, 13.8 mmol, 1.2 eq.) in 22 mL of anhydrous DCM (0.52 M). The solution was stirred for 45 min under an argon atmosphere, after which, the crude mixture was subjected to column chromatography on silica (10:90 EtOAc:hexanes) to afford triflate (2.61 g, 9.75 mmol, 85%).

Following general procedure A, to a solution of 2-hydroperoxy-tetrahydro-2H-pyran (1 b) (472 mg, 4 mmol, 1.5 eq.) dissolved in 10 mL of anhydrous THF (0.4M) was added LiOtBu (280 mg, 3.5 mmol, 1.3 eq.) in a single portion under an argon atmosphere at 0° C. After 10 minutes of stirring, a portion of the triflate (724 mg, 2.7 mmol, 1 eq.) obtained in the previous step was then added and the mixture was allowed to warm to ambient temperature and stirred for 1 hr under an argon atmosphere. The crude mixture was subjected to flash silica column chromatography (10:90 EtOAc:hexanes) to afford the title compound 2a (604 mg, 2.56 mmol, 95%) as a clear oil. R$_f$=0.6 (10:90 EtOAc:Hexanes; UV, CAM). $^1$H NMR (500 MHz, CDCl$_3$): δ 7.27 (dd, J=8.2, 6.9 Hz, 2H), 7.18 (dt, J=8.1, 1.9 Hz, 3H), 5.14 (t, J=3.8 Hz, 1H), 4.11 (t, J=6.4 Hz, 2H), 4.00 (ddd, J=11.1, 8.0, 2.9 Hz, 1H), 3.66-3.58 (m, 1H), 2.71 (dd, J=8.7, 6.8 Hz, 2H), 2.01-1.90 (m, 2H), 1.78-1.66 (m, 2H), 1.66-1.50 (m, 4H). $^{13}$C NMR (126 MHz, CDCl3): δ 141.79, 128.63 (2C), 128.51 (2C), 126.03, 100.98, 74.61, 62.75, 32.31, 29.67, 28.09, 25.30, 19.90. HRMS-ESI (m/z): [M+Na]$^+$ calculated for [C$_{14}$H$_{20}$O$_3$Na]$^+$: 259.1305, found: 259.1299.

MTHP Monoperoxyacetal (2b)

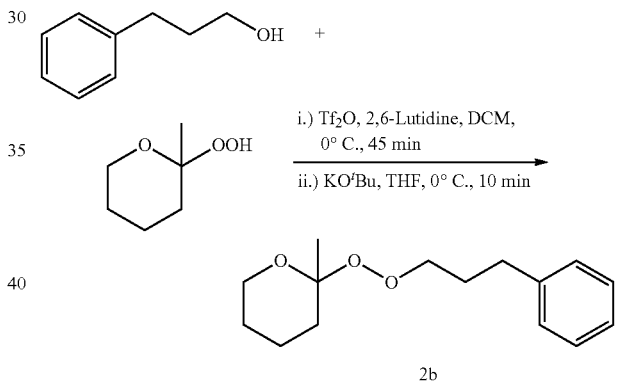

The reaction was performed following general procedure A with 3-phenylpropanol (0.68 mL, 5.0 mmol, 1.0 equiv.), 2,6-lutidine (7.3 mL, 0.84 mmol, 1.5 eq.) and Tf$_2$O (1.2 mL, 1.4 eq. in 30 mL of anhydrous DCM (0.17 M). The solution was stirred for 45 min under an argon atmosphere, after which the crude reaction mixture was subjected to column chromatography (20:80 EtOAc:hexanes) to afford the triflate as a pale yellow oil (1.09 g, 4.1 mmol, 82%).

Following general procedure A, to a solution of 2-hydroperoxy-2-methyltetrahydro-2H-pyran (1b) (1.0 mmol, 132.16 mg, 1.0 equiv.) dissolved in anhydrous THF (4.5 mL) was added in a single portion KOtBu (1.3 mmol, 146 mg, 1.3 mmol) and the solution was stirred for 10 minutes. A portion of the alkyl triflate (2.0 mmol, 540 mg dissolved in 0.5 mL of anhydrous THF, 2 equiv.) obtained in the previous step was then added drop wise over 5 minutes. The reaction was stirred at 0° C. for 10 min under an argon atmosphere. The crude mixture was subjected to flash column chromatography (100:0-90:10 hexanes:EtOAc) to afford MTHP monoperoxy acetal 2b as a colorless oil (172.5 mg, 0.69 mmol, 69%). Spectral data are in accord with what has been previously reported. R$_f$=0.33 (10% EtOAc/hexanes;

UV/CAM). ¹H NMR (500 MHz, CDCl₃) δ 7.31-7.25 (m, 2H), 7.19 (ddt, J=14.2, 6.6, 1.6 Hz, 3H), 4.06 (td, J=6.4, 1.3 Hz, 2H), 3.92 (td, J=11.5, 2.9 Hz, 1H), 3.71 (ddt, J=11.3, 4.6, 1.9 Hz, 1H), 2.72 (dd, J=8.8, 6.9 Hz, 2H), 1.98 (dq, J=9.3, 6.6 Hz, 2H), 1.76 (ddd, J=12.5, 4.1, 2.4 Hz, 1H), 1.75-1.65 (m, 1H), 1.67-1.49 (m, 3H), 1.46 (s, 3H). ¹³C NMR (126 MHz, CDCl₃) δ 141.80, 128.56 (2C), 128.45 (2C), 125.96, 102.33, 74.37, 61.76, 33.38, 32.39, 29.72, 24.91, 24.60, 19.15. HRMS-ESI (m/z): [M+Na]⁺ calculated for [C₁₅H₂₂O₃Na]⁺: 273.1461, found: 273.1457.

MTHP Monoperoxyacetal (2c)

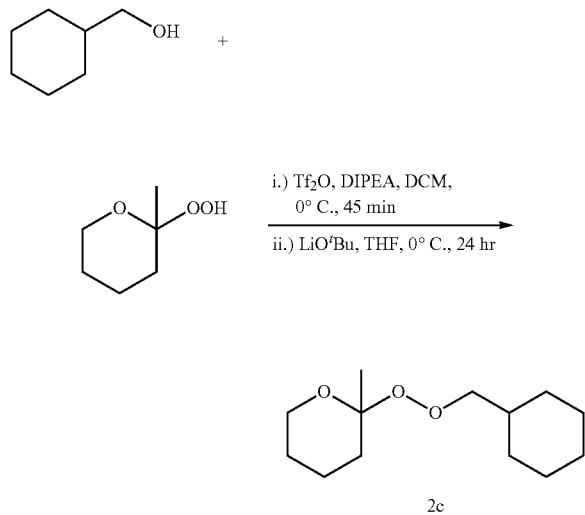

The reaction was performed following general procedure A with cyclohexanemethanol (250 μL, 2 mmol, 1.0 eq.), diisopropylethylamine (520 μL, 3 mmol, 1.5 eq.), and Tf₂O (500 μL, 3 mmol, 1.5 eq.) in 12 mL anhydrous DCM (0.17 M). The solution was stirred for 1 hr under an argon atmosphere, after which the crude reaction mixture was subjected to column chromatography (20:80 EtOAc: hexanes) to afford triflate (470 mg, 1.91 mmol, 95%).

Following general procedure A, to a solution of 2-hydroperoxy-2-methyltetrahydro-2H-pyran (1b) (360 mg, 3.4 mmol, 1.5 eq.) dissolved in 8 mL of anhydrous THF (0.3 M) was added LiOtBu (240 mg, 3.04 mmol, 1.3 eq.) in a single portion under an argon atmosphere at 0° C. The reaction mixture was stirred for 10 min, after which, a portion of the triflate (450 μL, 2.4 mmol, 1.0 eq.) obtained in the previous step was then added and the mixture was allowed to warm to room temperature and stirred for 24 hours under an argon atmosphere. The crude mixture was subjected to flash silica column chromatography (5:95 EtOAc:hexanes) to afford the title compound 2c (334 mg, 1.46 mmol, 61% yield) as a colorless oil. R$_f$=0.30 (10:90 EtOAc:Hexanes; UV, CAM). ¹H NMR (500 MHz, CDCl₃): δ 3.93 (td, J=11.5, 2.9 Hz, 1H), 3.89-3.80 (m, 2H), 3.70 (ddt, J=11.4, 4.4, 1.9 Hz, 1H), 1.84-1.50 (m, 12H), 1.43 (s, 3H), 1.30-1.12 (m, 3H), 1.04-0.92 (m, 2H). ¹³C NMR (126 MHz, CDCl₃): δ 102.40, 80.97, 61.79, 36.78, 33.48, 30.32 (2C), 26.67, 25.94 (2C), 24.98, 24.58, 19.20. HRMS-ESI (m/z): [M+Na]⁺ calculated for [C₁₃H₂₄O₃Na]⁺: 251.1610, found: 251.1618.

MTHP Monoperoxyacetal (2d)

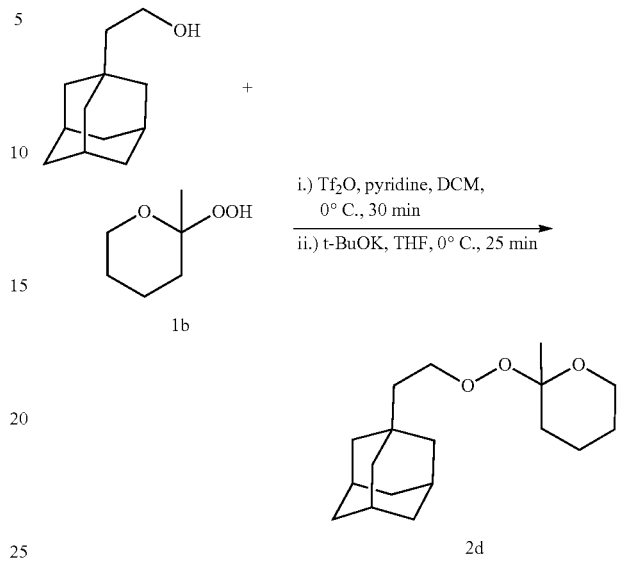

The reaction was performed following general procedure A with adamantylethanol (360 mg, 2 mmol, 1.0 eq.), diisopropylethylamine (520 μL, 3 mmol, 1.5 eq), and Tf2O (500 μL, 3 mmol, 1.5 eq.) in 12 mL anhydrous DCM (0.17 M). The solution was stirred for 30 min under an argon atmosphere, after which, the crude reaction mixture was subjected to column chromatography (10:90 EtOAc:hexanes) to afford triflate (470 mg, 1.50 mmol, 75%).

Following general procedure A, to a solution of 2-hydroperoxy-2-methyltetrahydro-2H-pyran (1b) (2.26 mmol, 299 mg, 1.5 equiv.) under an argon atmosphere dissolved in anhydrous THF (7 mL) was added KOtBu (1.5 mmol, 253.6 mg, 2.26 mmol) in a single portion at 0° C. The solution was stirred for 10 min, after which, the triflate (470 mg, 1.5 mmol, 1.0 eq.) obtained in the previous step dissolved in 0.5 mL of anhydrous THF was added dropwise over 5 min. The reaction was stirred at 0° C. for 25 min under an argon atmosphere. The crude reaction mixture was subjected to flash column chromatography (100:0-90:10 hexanes: EtOAc) to afford the MTHP monoperoxyacetal 2d as a colorless oil (423.5 mg, 1.44 mmol, 96%). R$_f$=0.52 (10% EtOAc/hexanes; CAM). ¹H NMR (500 MHz, CDCl₃): δ 4.08 (qt, J=9.0, 7.3 Hz, 2H), 3.91 (td, J=11.5, 2.9 Hz, 1H), 3.68 (ddt, J=11.4, 4.5, 2.0 Hz, 1H), 1.92 (p, J=3.2 Hz, 3H), 1.76-1.57 (m, 10H), 1.54-1.49 (m, 8H), 1.41 (s, 3H), 1.39 (t, J=7.4 Hz, 2H). ¹³C NMR (126 MHz, CDCl₃): δ 102.36, 71.42, 61.86, 42.82 (3C), 41.54, 37.27(3C), 33.50, 31.90, 28.88 (3C), 25.04, 24.77, 19.27. HRMS-ESI (m/z): [M+Na]⁺ calculated for [C₁₈H₃₀O₃Na]⁺, 317.2087; found: 317.2079.

Synthesis of MTHP Monoperoxyacetal (2e)

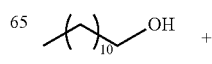

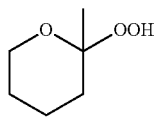

1b i.) Tf$_2$O, 2,6-Lutidine, DCM, 0° C., 1 hr
ii.) t-BuOK, THF, 0° C., 15 min

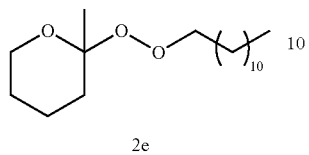

2e

The reaction was performed following general procedure A with dodecanol (2.38 mL, 11.5 mmol, 1.0 eq.), 2,6-lutidine (2.0 mL, 17.25 mmol, 1.5 eq), and Tf$_2$O (2.3 mL, 13.8 mmol, 1.2 eq.) in 22 mL anhydrous DCM (0.5 M). The solution was stirred for 1 hr under an argon atmosphere, after which the crude reaction mixture was subjected to column chromatography (10:90 EtOAc:hexanes) to afford the triflate (3.04 g, 9.55 mmol, 83%) as a colorless oil.

Following general procedure A, to a solution of 2-hydroperoxy-2-methyltetrahydro-2H-pyran (1b) (1.45 mmol, 192 mg, 1.5 equiv) under an argon atmosphere dissolved in anhydrous THF (4.5 mL) was added KOtBu (1.5 mmol, 1.45 mmol, 163 mg) in a single portion at 0° C. The reaction was stirred for 3 min at 0° C., after which, a portion of the triflate (308 mg, 0.97 mmol, 1.0 eq.) obtained in the previous step dissolved in 0.5 mL of anhydrous THF was added dropwise over 5 min. The reaction was stirred at 0° C. for 15 min under an argon atmosphere. The crude reaction mixture subjected to flash column chromatography (100:0-96:4 Hexanes:EtOAc) to afford MTHP monoperoxyacetal 2e as a colorless oil (241 mg, 0.80 mmol, 83%). R$_f$=0.6 (15% EtOAc/hexanes; CAM). $^1$H NMR (500 MHz, CDCl$_3$): δ 4.07-3.97 (m, 2H), 3.92 (td, J=11.5, 2.9 Hz, 1H), 3.69 (ddt, J=11.3, 4.4, 1.9 Hz, 1H), 1.78-1.48 (m, 5H), 1.42 (s, 3H), 1.40-1.24 (m, 9H), 1.24 (s, 11H), 0.86 (t, J=6.9 Hz, 3H). $^{13}$C NMR (126 MHz, CDCl$_3$): δ 102.35, 75.43, 61.79, 33.44, 32.07, 29.80, 29.77, 29.73, 29.68, 29.61, 29.49, 28.06, 26.27, 24.97, 24.60, 22.83, 19.19, 14.26. HRMS-ESI (m/z): [M+Na]$^+$ calculated for [C$_{18}$H$_{36}$O$_3$Na]$^+$, 323.2557; found: 323.2557.

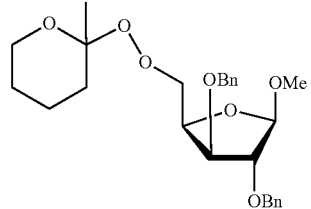

2g

The reaction was performed following general procedure B with methyl β-D-xylofuranoside I1 (816 mg, 2.5 mmol, 1.0 eq.), pyridine (403 μL, 5.0 mmol, 2.0 eq.) and Tf$_2$O (504 μL, 3.0 mmol, 1.2 eq.) in 20 mL of anhydrous DCM (0.13 M). The solution was stirred for 45 min under an argon atmosphere, after which the crude mixture was subjected to column chromatography on silica (15:85 EtOAc:hexanes) to afford the triflate (920 mg, 1.93 mmol, 77%).

Following general procedure B, to a solution of 2-hydroperoxy-2-methyltetrahydro-2H-pyran (200 mg, 1.5 mmol, 1.0 eq.) dissolved in 6 mL of anhydrous DMF was added NaH (60% dispersion in mineral oil) (84 mg, 2.1 mmol, 1.4 eq.) in a single portion under an argon atmosphere at 0° C. After 10 min, the triflate (710 μL, 1.95 mmol, 1.3 eq.) obtained in the previous step was then added and the mixture was allowed to warm to room temperature over 30 min and stirred for 16 h under an argon atmosphere. The crude mixture was subjected to flash column chromatography on silica (eluent: 20:80 EtOAc:Hexanes) to afford MTHP monoperoxyacetal 2 g (279 mg, 0.61 mmol, 41%) as a clear oil. The MTHP monoperoxyacetal 2 g was obtained as a 1:1 ratio of diastereomers. Where doubling of $^1$H and $^{13}$C resonances was observed, one signal is reported. R$_f$=0.60 (30:70 EtOAc:Hexanes; UV, CAM). $^1$H NMR (500 MHz, CDCl$_3$): δ 7.37-7.27 (m, 10H), 4.91 (d, J=5.0 Hz, 1H), 4.64-4.45 (m, 2H), 4.39-4.34 (m, 1H), 4.28-4.22 (m, 1H), 4.09-4.05 (m, 1H), 3.97-3.95 (m, 1H), 3.95-3.88 (m, 1H), 3.70-3.66 (m, 1H), 3.39 (s, 3H), 1.76-1.48 (m, 6H), 1.44 (d, 3H). $^{13}$C NMR (126 MHz, CDCl$_3$): δ 137.9, 137.7, 128.6 (2C), 128.5 (2C), 128.1, 128.0 (3C0, 127.9 (2C0, 108.2, 102.6, 87.2, 82.1, 78.3, 75.1, 72.4, 61.9, 55.7, 33.4, 24.9, 24.7, 24.6, 19.2. HRMS-ESI (m/z): [M+Na]$^+$ calculated for [C$_{26}$H$_{34}$O$_7$Na]$^+$: 481.2181, found: 481.2177.

MTHP Monoperoxyacetal (2q)

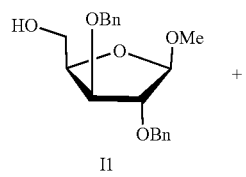

I1

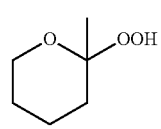

i.) Tf$_2$O, pyridine, DCM, 0° C., 45 min
ii.) NaH, DMF, 0° C., 16 h

MTHP Monoperoxyacetal (2h)

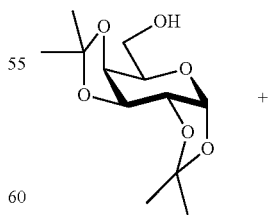

I2

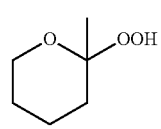

i.) Tf$_2$O, pyridine, DCM, 0° C., 40 min
ii.) NaH, DMF, 0° C. → 21° C., 16 h

-continued

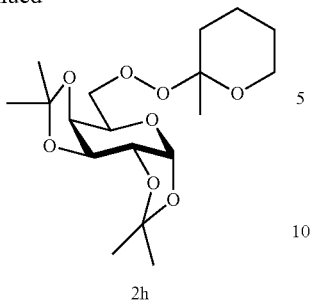

2h

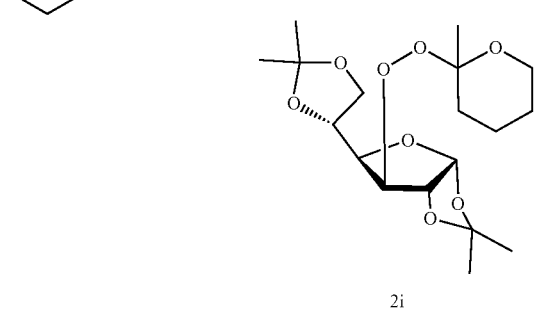

2i

The reaction was performed following general procedure B with diacetone D-galactopyranose 12 (1 g, 3.8 mmol, 1.0 eq.), pyridine (600 μL, 7.7 mmol, 2.0 eq.) and Tf$_2$O (770 μL, 4.6 mmol, 1.2 eq.) in 20 mL of anhydrous DCM (0.19 M). The solution was stirred for 40 min under an argon atmosphere, after which, the crude mixture was subjected to column chromatography on silica (20:80 EtOAc:hexanes) to afford the triflate (1.43 g, 3.65 mmol, 96%).

Following general procedure B, to a stirred solution of 2-hydroperoxy-2-methyltetrahydro-2H-pyran (627 mg, 4.75 mmol, 1.3 eq.) dissolved in anhydrous DMF (15 mL) was added NaH (60% dispersion in mineral oil) (167 mg, 4.38 mmol, 1.2 eq.) in a single portion under an argon atmosphere at 0° C. After 10 min of stirring a solution of alkyl triflate (1.43 g, 3.65 mmol, 1.0 eq.) dissolved in 2 mL of anhydrous DMF obtained in the previous step was then added and the mixture was allowed to warm to room temperature over 30 min and stirred for 4 h under an argon atmosphere. The crude mixture was subjected to flash column chromatography on silica (eluent: 98:2-80:20 Hexanes:EtOAc) to afford the MTHP monoperoxyacetal 2h (1.07 g, 2.86 mmol, 78%) as a clear oil. The MTHP monoperoxyacetal 2h was obtained as a 1:1 mixture of diastereomers. Where doubling of $^1$H and $^{13}$C resonances was observed, one signal is reported. Spectral data are in accord with that previously reported in the literature. R$_f$=0.30 (10:90 EtOAc:Hexanes; CAM, H$_2$SO$_4$). $^1$H NMR (500 MHz, CDCl$_3$): δ 5.54 (dd, J=4.8, 1.8 Hz, 1H), 4.61 (dd, J=7.9, 2.4 Hz, 1H), 4.32-4.28 (m, 2H), 4.28-4.08 (m, 3H), 3.93 (m, 1H), 3.69 (ddt, J=11.3, 4.3, 2.0 Hz, 1H), 1.77-1.54 (m, 4H), 1.54 (s, 3H0, 1.54-1.47 (m, 2H), 1.46-1.41 (m, 6H0, 1.32 (d, J=2.7 Hz, 6H). $^{13}$C NMR (126 MHz, CDCl$_3$): δ 109.5, 108.7, 102.6, 96.6, 74.1, 71.3, 70.8 (2C), 65.0, 61.9, 33.4, 26.2, 26.1, 25.2 (2C), 24.9, 24.7, 19.2. HRMS-ESI (m/z): [M+Na]$^+$ calculated for [C$_{18}$H$_{30}$O$_8$Na]$^+$: 397.1833, found: 397.1829.

MTHP Monoperoxyacetal (2i)

The reaction was performed following general procedure B with diacetone D-allofuranoside (1 g, 3.8 mmol, 1.0 eq.), pyridine (600 μL, 7.7 mmol, 2.0 eq.) and Tf$_2$O (770 μL, 4.6 mmol, 1.2 eq.) in 20 mL of anhydrous DCM (0.19 M). The crude mixture was subjected to column chromatography on silica (20:80 EtOAc:hexanes) to afford the triflate (1.43 g, 3.64 mmol, 96%)

Following general procedure B, to a solution of 2-hydroperoxy-2-methyltetrahydro-2H-pyran (1b) (200 mg, 1.5 mmol, 1.5 equiv.) dissolved in anhydrous DMF (4 mL) was added NaH (60% dispersion in mineral oil) (48 mg, 1.2 mmol, 1.2 equiv.) in a single portion under an argon atmosphere at 0° C. After 10 minutes of stirring, a solution of alkyl triflate (392 mg, 1.0 mmol, 1.0 eq.) obtained in the previous step in 1 mL of anhydrous DMF was then added dropwise and the mixture was allowed to reach room temperature and stirred for 4 hr under an argon atmosphere. The crude reaction mixture was then subjected to flash column chromatography on neutral alumina (100:0-80:20 DCM:EtOAc) to afford the title compound 2i (180 mg, 0.48 mmol, 48%) as a colorless oil. The MTHP monoperoxy acetal 2i was obtained as a 1:1 ratio of diastereomers. Where doubling of $^1$H and $^{13}$C resonances was observed, one signal is reported. R$_f$=0.17 (5% EtOAc/DCM, CAM, H$_2$SO$_4$). $^1$H NMR (500 MHz, CDCl$_3$): δ 5.88 (d, J=3.8 Hz, 1H), 4.86 (dd, J=10.6, 3.9 Hz, 1H), 4.60 (d, J=3.5 Hz), 4.53 (d, J=3.6 Hz), 4.31 (tt, J=6.0, 3.6 Hz, 1H), 4.27 (dd, J=6.3, 3.6 Hz), 4.19 (dd, J=7.7, 3.7 Hz), 4.05 (ddd, J=8.6, 6.2, 4.7 Hz, 1H), 3.93 (ddd, J=8.8, 5.9, 3.1 Hz, 1H), 3.85 (qd, J=11.5, 2.9 Hz, 1H), 3.67 (dddd, J=13.7, 11.7, 4.5, 2.0 Hz, 1H,), 1.80-1.71 (m, 1H), 1.71-1.60 (m, 1H), 1.60-1.50 (m, 4H), 1.49 (s, 3H), 1.46-1.38 (m, 6H), 1.37-1.30 (m, 6H). $^{13}$C NMR (126 MHz, CDCl$_3$): δ 111.88, 109.07, 105.31, 103.19, 86.12, 81.87, 80.25, 72.27, 66.81, 61.90, 33.19, 26.95, 26.43, 25.52, 24.79, 24.29, 19.12. HRMS-ESI (m/z): [M+Na]$^+$ calculated for [C$_{18}$H$_{38}$O$_8$Na]$^+$: 397.1833; found: 397.1833.

MTHP Monoperoxyacetal (2i)

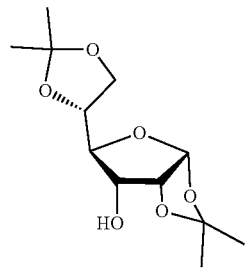

+

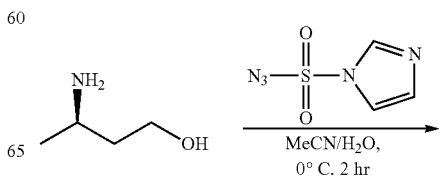

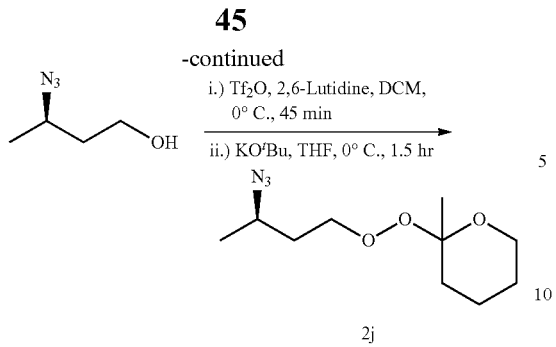

2j

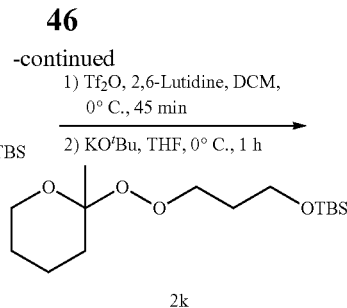

2k

To a solution of (R)-3-aminobutanol (2.0 mL, 22 mmol, 1.0 eq.) in 150 mL of MeCN:H$_2$O (4:1) was added CuSO$_4$ (550 mg, 2.2 mmol, 0.1 eq.) and Et$_3$N (12.3 mL, 88 mmol, 4.0 eq.) at 0° C. The solution was stirred for 5 min, after which 1-imidazolesulfonyl azide (Stick's reagent) (9.2 g, 44 mmol, 2.0 eq.) was added portion-wise and the solution was allowed to warm to room temperature and stirred for 2 h. After such time, the crude reaction mixture was concentrated and redissolved in EtOAc (75 mL) and the organic layer was washed with a 15% HCl solution (4×10 mL), followed by NaHCO$_3$ (2×15 mL) and saturated NaCl (1×20 mL). The organic layers were combined and dried over Na$_2$SO$_4$, filtered, and concentrated in vacuo to give pure azide (1.88 g, 16.3 mmol, 74%) as a yellow oil which was used directly in the next reaction without further purification. Spectral data are in accord with those previously reported. R$_f$=0.50 (1:9 MeOH:DCM; CAM). $^1$H NMR (500 MHz, CDCl$_3$): δ 3.82-3.64 (m, 3H), 1.77-1.64 (m, 3H), 1.32 (d, J=6.6 Hz, 3H). $^{13}$C NMR (126 MHz, CDCl$_3$): δ 59.9, 55.5, 38.7, 19.7. [α]$_D$=−23.0 (c=1.0 g/100 mL, CHCl$_3$).

Following general procedure A with a portion of 3-azidobutanol (1.85 g, 16.09 mmol, 1.0 eq.) obtained in the previous step, 2,6-lutidine (2.8 mL, 24.13 mmol, 1.5 eq.) and Tf$_2$O (3.24 mL, 19.3 mmol, 1.22 eq.) in 40 mL of anhydrous DCM (0.40 M) and the reaction mixture was stirred for 45 min at 0° C. The crude mixture was subjected to column chromatography on silica (1:9 MeOH:DCM) to afford the triflate (3.94 g, 15.9 mmol, 98%).

Following general procedure A, to a solution of 2-hydroperoxy-2-methyltetrahydro-2H-pyran (1b) (2.5 mL, 20.8 mmol, 1.3 equiv.) under an argon atmosphere dissolved in anhydrous THF (55 mL) was added KO$^t$Bu (2.15 g, 19.2 mmol, 1.2 eq) in a single portion at 0° C. The reaction was stirred for 10 min at 0° C., after which a portion of the triflate (3.94 g, 15.9 mmol, 1.0 eq.) obtained in the previous step was added dropwise. The reaction was stirred at 0° C. for 1 hr under an argon atmosphere. The crude reaction mixture was subjected to column chromatography (15:85 EtOAc:Hexanes) to afford the title compound (2j) (1.93 g, 8.42 mmol, 53%) as a colorless oil. R$_f$=0.85 (2:8 EtOAc/Hexanes, CAM). $^1$H NMR (500 MHz, CDCl$_3$): δ 4.17-4.09 (m, 2H), 3.93-3.88 (m, 1H), 3.73-3.65 (m, 2H), 1.85-1.65 (m, 4H), 1.61-1.53 (m, 4H), 1.43 (d, J=5.0 Hz, 3H), 1.30 (d, J=5.0 Hz, 3H). $^{13}$C NMR (126 MHz, CDCl$_3$): δ 102.55, 71.77, 61.87 55.21, 34.80 (2C), 33.32, 24.90 (2C), 19.76, 19.16. HRMS-ESI (m/z): [M+Na]$^+$ calculated for [C$_{10}$H$_{19}$O$_3$N$_3$Na]$^+$: 252.1302; found: 252.1306. [α]$_D$= −32.0° (c=1.0 g/100 mL, CHCl$_3$).

MTHP monoperoxyacetal (2 k)

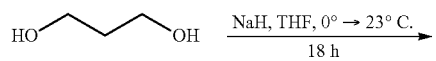

To a solution of NaH (60%) (1.7 g, 26.3 mmol, 1.0 eq) in 45 mL anhydrous THF was added 1,3-propanediol (5.6 mL, 78.9 mmol, 3.0 eq) at 0° C. dropwise under an argon atmosphere. The solution was stirred for 10 minutes after which TBSCl (3.96 g, 26.3 mmol, 1.0 eq) was added portionwise to the solution at 0° C. The solution was allowed to reach ambient temperature (23° C.) over 30 minutes and stirred for 18 hrs. After such time, the reaction mixture was quenched with NaHCO$_3$ (100 mL), and the aqueous layer extracted with Et$_2$O (3×70 mL). The organic layers were combined and dried over Na$_2$SO$_4$, filtered, and concentrated in vacuo to give pure monosilylated product (4.80 g, 25.2 mmol, 96%) as a clear oil. R$_f$=0.5 (20:80 EtOAc:Hexanes; CAM). $^1$H NMR (500 MHz, CDCl$_3$): δ 3.87-3.75 (m, 4H), 1.77 (p, J=5.6 Hz, 2H), 1.24 (s, 1H), 0.89 (s, 9H), 0.06 (s, 6H). $^{13}$C NMR (126 MHz, CDCl$_3$): δ 63.06, 62.58, 34.33, 26.01 (3C), 18.32,-5.36 (2C). HRMS-ESI (m/z): [M+Na]$^+$ calculated for [C$_9$H$_{22}$O$_2$NaSi]$^+$: 213.1281; found: 213.1276.

Following general procedure A with a portion of 3-((tert-Butyldimethylsilyl)oxy)propan-1-ol (1.5 g, 7.89 mmol, 1 eq) obtained in the previous step, 2,6-lutidine (1.4 mL, 11.84 mmol, 1.5 eq) and Tf$_2$O (1.6 mL, 9.46 mmol, 1.2 eq) in 20 mL of anhydrous DCM and the reaction mixture was stirred for 45 min at 0° C. The crude mixture was subjected to column chromatography on silica (20:80 EtOAc:Hexanes) to afford the triflate (2.46 g, 7.6 mmol, 97%).

Following general procedure A, to a solution of 2-hydroperoxy-2-methyltetrahydro-2H-pyran (1b) (1.20 g, 9.1 mmol, 1.2 eq) under an argon atmosphere dissolved in anhydrous THF (22 mL) was added KO$^t$Bu (852 mg, 7.6 mmol, 1.0 eq) in a single portion at 0° C. The reaction was stirred for 10 min at 0° C. after which the triflate (2.46 g, 7.6 mmol, 1.0 eq) obtained in the previous step was added dropwise. The reaction was stirred at 0° C. for 1 hr under an argon atmosphere. The crude reaction mixture was subjected to column chromatography (10:90 EtOAc:hexanes) to afford the title compound (2 k) (2.15 g, 7.06 mmol, 93%) as a colorless oil. R$_f$=0.8 (2:8 EtOAc:hexanes, CAM). $^1$H NMR (500 MHz, CDCl$_3$): δ 4.12 (t, J=6.4 Hz, 2H), 3.91 (td, J=11.4, 2.8 Hz, 1H), 3.73-3.67 (m, 3H), 1.85 (p, J=6.4 Hz, 2H), 1.77-1.63 (m, 2H), 1.57-1.48 (m, 4H), 1.42 (s, 3H), 0.88 (s, 9H), 0.04 (s, 6H). $^{13}$C NMR (126 MHz, CDCl$_3$): δ 102.34, 72.22, 61.80, 60.07, 33.42, 31.48, 26.06 (3C), 24.96, 24.60, 19.18, 18.45, −5.22 (2C). HRMS-ESI (m/z): [M+Na]$^+$ calculated for [C$_{15}$H$_{32}$O$_4$NaSi]$^+$: 327.1959; found: 327.1953.

Example 8: Optimization of Reaction Conditions

The reaction of known 3-phenylpropyl tetrahydropyranyl (THP) monoperoxyacetal (2a) with a range of dialkylamines was evaluated. Unfortunately, no reaction was observed with the amine alone or under the basic conditions reported by Yamamoto for the oxidation of amines with benzoyl peroxide (Table 1; entries 1-4). However, the N,N,O-trisubstituted hydroxylamine (3a) was prepared in 50% yield through reaction of the lithium N-methylanilide with 2a (Table 1; entry 5). A slightly improved yield was observed upon the reaction of corresponding magnesium amide with 2a (Table 1; entry 6)). 3-Phenylpropanol and δ-valerolactone were also formed in a 23% yield, likely through Kornblum-DeLaMare elimination of the tetrahydropyranyl ring in 2a (Table 1; entry 6). To circumvent elimination, the 3-phenylpropyl MTHP monoperoxy acetal (2b) with the magnesium amide was then investigated and a markedly improved yield of 95% of the intended product 3a was observed (Table 1; entry 7).

TABLE 1

Optimization of Reaction Conditions

| Entry[a] | R = | Additive | Solvent | Temperature (° C.) | Yield of 3a (%)[b] |
|---|---|---|---|---|---|
| 1 | H | None | DCM | 40 | 0[c] |
| 2 | H | Cs$_2$CO$_3$ | DCM | 40 | 0[c] |
| 3 | H | Sc(OTf)$_3$ | DCM | 23 | 0[c] |
| 4 | H | Cu(OTf)$_2$ | DCM | 23 | 0[c] |
| 5 | H | n-BuLi (2.5M) | THF | 0 | 50 |
| 6 | H | EtMgBr (3M) | THF | 0 | 54 |
| 7 | Me | EtMgBr (3M) | THF | 0 | 95 |

[a]All reactions were performed at a 0.2 mmol scale
[b]Isolated yields after column chromatography.
[c]Reaction performed for 48 hours with monitoring by TLC and MS.

Scope of Amines Useful in the Process

With optimized reaction conditions in hand for the synthesis of N,N,O-trisubstituted hydroxylamines (Table 1, entry 7), the scope of the amine was investigated (FIG. 4). The reaction was well tolerated with a variety of acyclic secondary amines furnishing products (3a, 3c, 3e, and 3f) in good to excellent yields (64-95%). Interestingly, even electron deficient diphenylamine afforded product (3e) in good yield (64%). The scope of the reaction was then expanded to a variety of N-heterocycles on account of their prevalence in medicinal chemistry and drug discovery. All N-heterocyclic amines reacted smoothly affording the N,N,O-trisubstituted hydroxylamine products (3b, 3d, 3 g, 3h, 3i, and 3j) in very good yields (68-98%).

Simple Alcohol Electrophiles

Figure 5A:
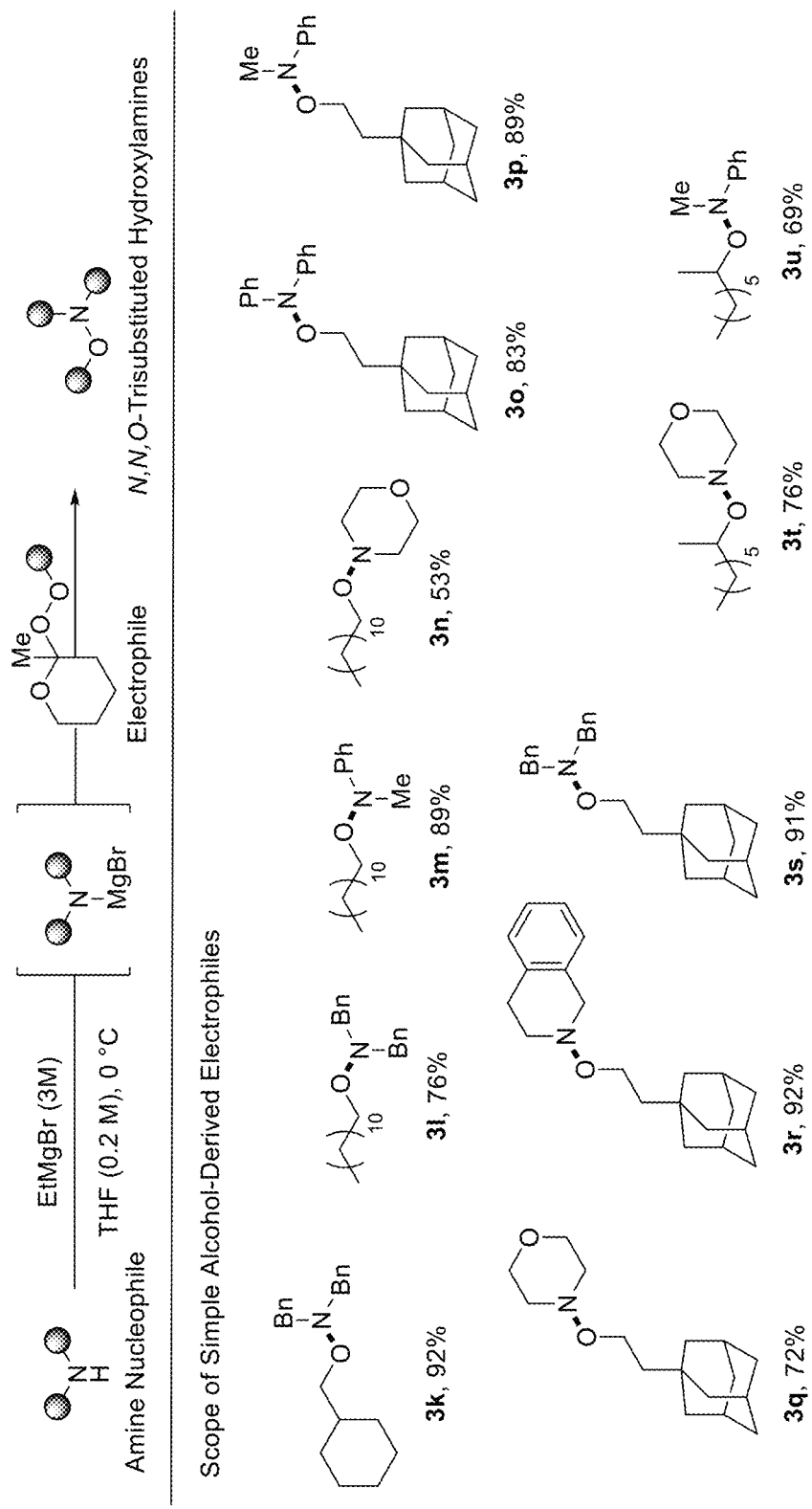
FIG. 5A shows simple alcohol electrophiles useful in the disclosed reactions as well as yields obtained in the reactions using the electrophiles.

With the reaction clearly tolerant of a wide array of amine nucleophiles, the scope of the alcohol-derived portion of the target hydroxylamines was explored (FIG. 5A). The cyclohexanemethanol-derived MTHP was used to probe the effects of sterics at the β-position of the alcohol: on reaction with magnesium dibenzylamide, the product (3 k) was afforded in 92% yield under the optimized conditions. The reaction also worked well with both adamantylethanol and dodecyl alcohol-derived MTHPs, affording products (3l, 3m, 3n, 3o, 3p, 3q, 3r, and 3s) through the reaction with various magnesium amides in good to excellent yields (54-95%). A secondary alcohol-derived MTHP was also a competent electrophile in the reaction, with the MTHP monoperoxyacetal of 2-octanol affording products (3t and 3u) in a 69 and 53% yield, respectively. A tert-butanol-derived MTHP, however, failed to react under the optimized conditions, demonstrating the influence of steric interactions.

Primary and Secondary Carbohydrate Alcohols

Figure 5B:
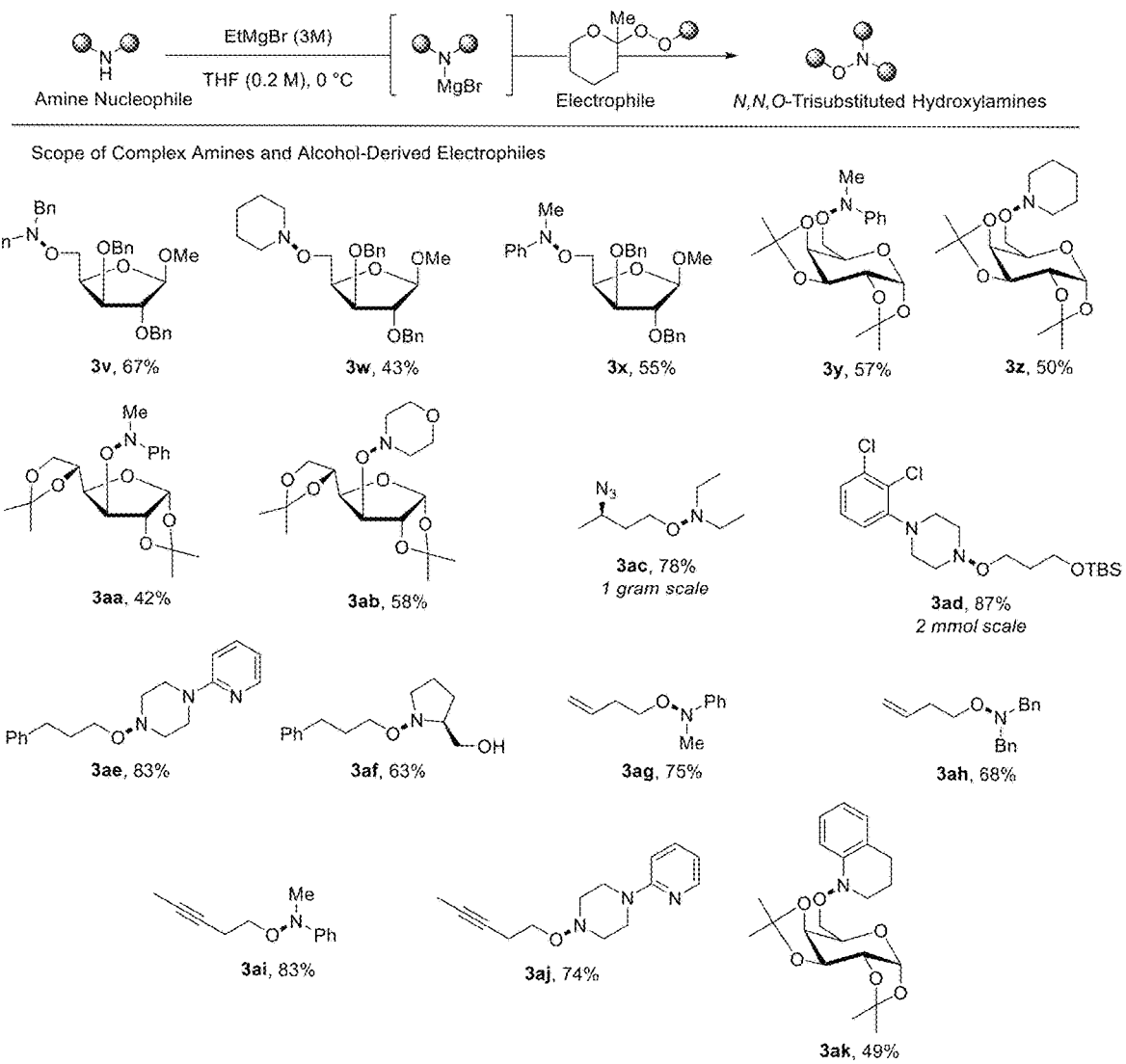
FIG. 5B shows complex alcohol electrophiles useful in the disclosed reactions as well as yields obtained in the reactions using the electrophiles. Additionally.
Figure 5C:
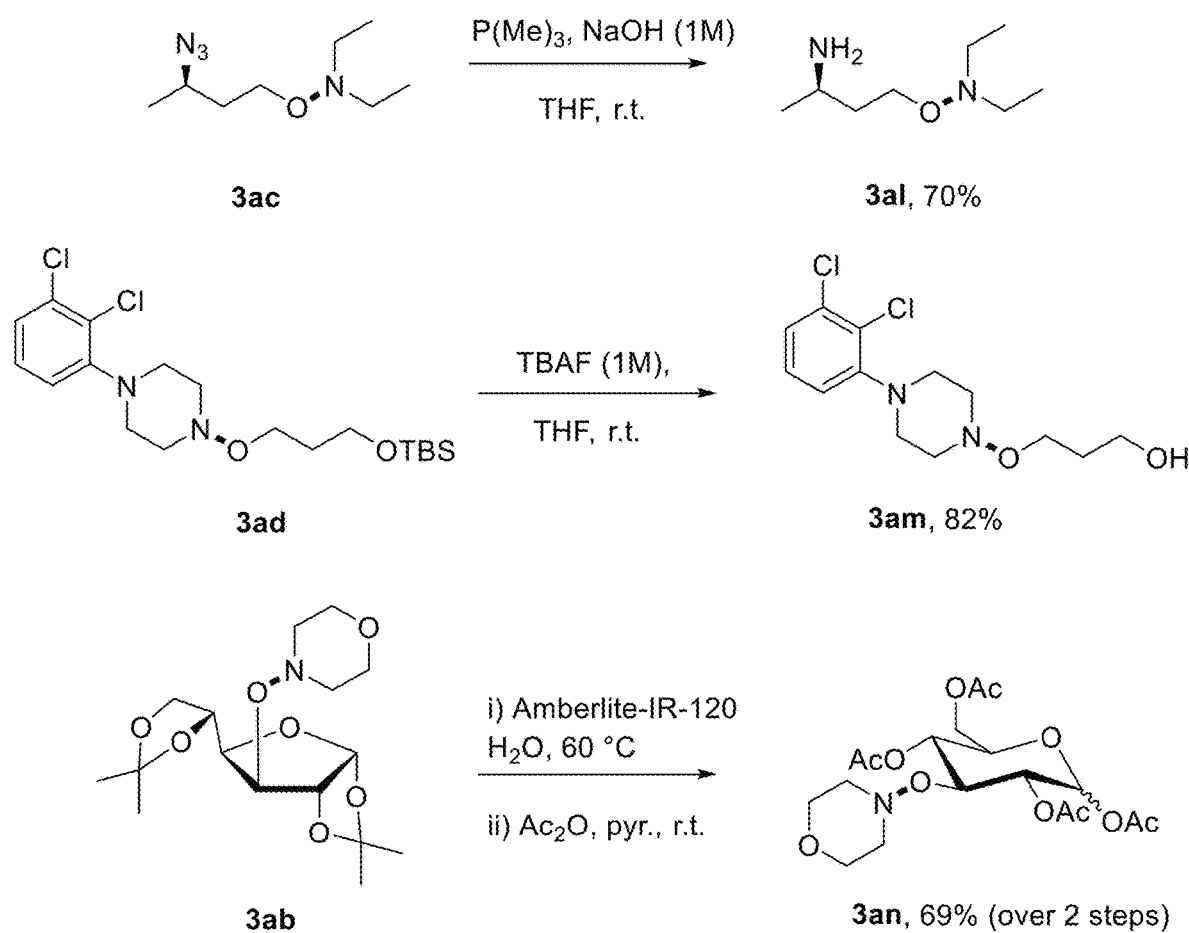
FIG. 5C shows deprotection schemes for exemplary hydroxylamines.

With a view to potential applications in glycodiversification, the tolerance of primary and secondary carbohydrate alcohols was next investigated (FIG. 5B). A 1,2;5,6-diacetoneglucofuranose-derived MTHP reacted under the optimized conditions with the magnesium salts of N-methylaniline and morpholine and affording hydroxylamine derivatives (3aa and 3ab) in fair yields (58 and 42%, respectively), likely reflecting the large steric interactions with the 5,6-acetonide. With the primary xylofuranose-derived MTHP hydroxylamines (3v, 3w, and 3x) were obtained in good yields (43-67%) upon reaction with various magnesium amides. Pyranoses were also well tolerated in the reaction with a 1,2;3,4-diacetonegalactopyranose-derived MTHP affording the expected products (3y and 3z) in good yields (50-57%). The formation of a hydroxylamine in the presence of an azide (3ac) and of a halo-substituted arene and a silyl ether (3ad) was also demonstrated in high yield.

Example 9: Proposed Mechanism

Figure 6:
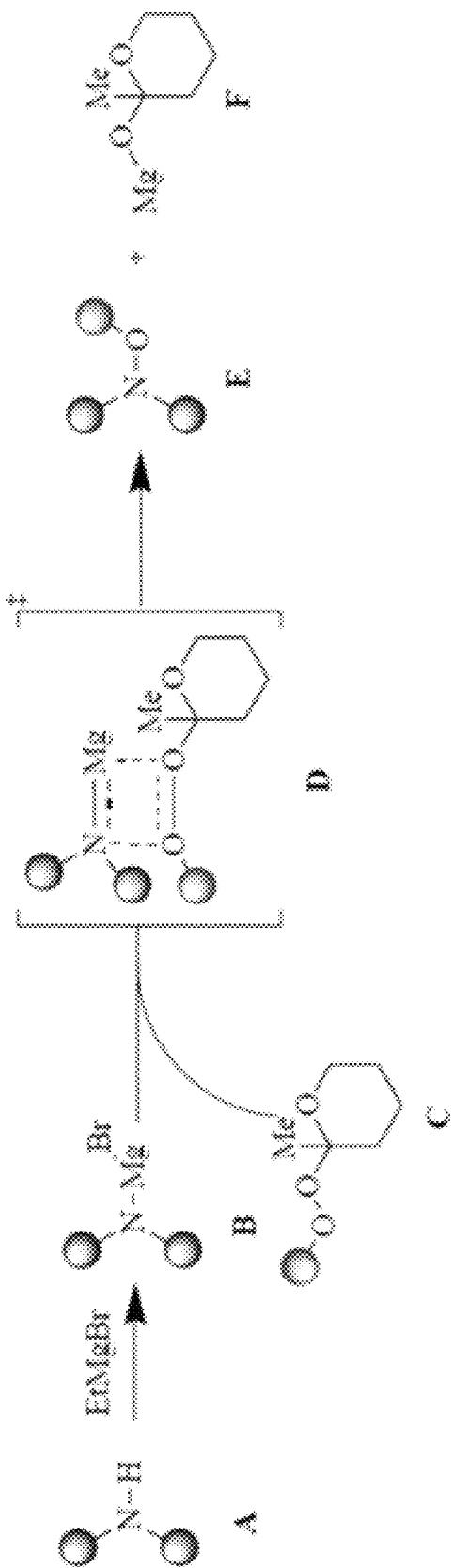
FIG. 6 shows a proposed mechanism for the formation of N,N,O-trisubstituted hydroxylamines according to one aspect of the present disclosure.

Extrapolating from previous work on the reactivity of MTHP monoperoxyacetals with Grignard reagents, a mechanism for the formation of N,N,O-trisubstituted hydroxylamines can be proposed (FIG. 6). Deprotonation of amine (A) with the Grignard reagent affords a magnesium amide (B) potentially reacts through a 4-membered cyclic transition state with the peroxide (D) leading to the N,N,O-trisubstituted hydroxylamine (E) and alkoxide (F). Although the present reaction does not benefit energetically from the release of ring-strain in previous endoperoxide ring-opening studies, the hydroxylamine forming reaction is still likely driven by the exothermic replacement of a labile peroxide bond (36-39 kcal·mol$^{-1}$) to a considerably stronger N—O bond in a hydroxylamine (55-65 kcal·mol$^{-1}$). A further contribution to the exothermicity of the process derives from the conversion of a magnesium amide to a magnesium alkoxide.

Example 10: Synthesis and Characterization of N,N,O-Trisubstituted Hydroxylamines Synthesis of hydroxylamine (3a) with MTHP monoperoxyacetal (2b)

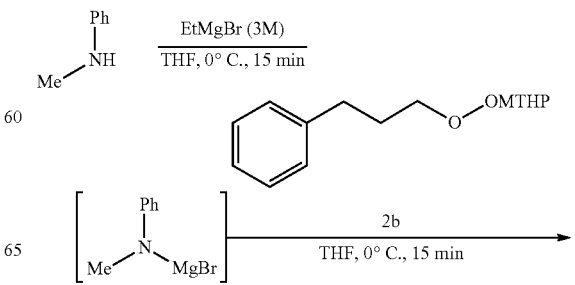

-continued

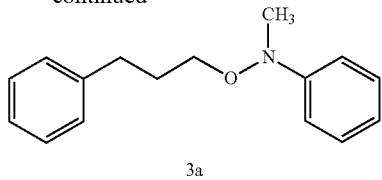

3a

Following general procedure C, N-methylaniline (54 mg, 0.5 mmol, 2.5 eq.) was dissolved in 0.5 mL of anhydrous THF. EtMgBr (3 M) (133 μL, 0.4 mmol, 2.0 eq.) was added dropwise over 5 min and the reaction mixture was stirred for 15 min at 0° C. After which, the magnesium amide solution was transferred to a stirred solution of MTHP monoperoxyacetal (2b) (50 mg, 0.2 mmol, 1 eq.) in 0.5 mL of anhydrous THF (0.2 M) and stirred for 15 min at 0° C. The crude mixture was subjected to flash silica column chromatography (10% EtOAc:hexanes) to afford the title compound 3a (44 mg, 0.19 mmol, 95%) as a colorless oil. $R_f$=0.65 (10% EtOAc:hexanes; UV, CAM). $^1$H NMR (500 MHz, CDCl$_3$): δ 7.34-7.27 (m, 4H), 7.25-7.17 (m, 3H), 7.10-7.04 (m, 2H), 7.02-6.95 (m, 1H), 3.89 (t, J=6.5 Hz, 2H), 3.09 (s, 3H), 2.80-2.70 (m, 2H), 2.07-1.97 (m, 2H). $^{13}$C NMR (126 MHz, CDCl$_3$): δ 153.10, 142.06, 129.09 (2C), 128.69 (2C), 128.63 (2C), 126.11, 122.11, 116.06 (2C), 72.33, 44.79, 32.79, 30.54. HRMS-ESI (m/z): [M+H]$^+$ calculated for [C$_{16}$H$_{20}$NO]$^+$: 242.1539, found: 242.1529.

Synthesis of hydroxylamine 3b with MTHP monoperoxyacetal (2b)

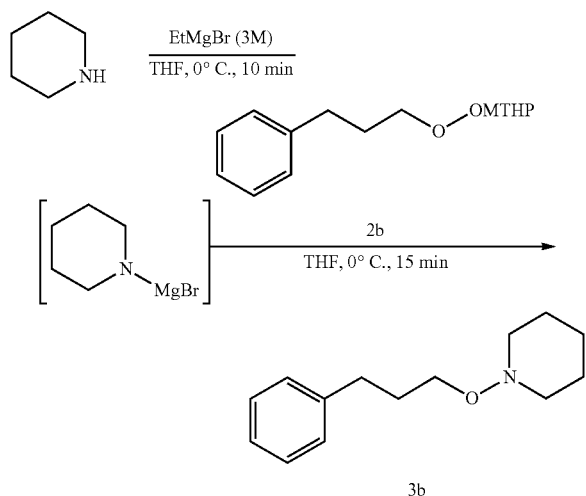

3b

Following general procedure C, piperidine (40 μL, 0.5 mmol, 2.5 eq.) was treated in 0.5 mL anhydrous THF with EtMgBr (3 M) (133 μL, 0.4 mmol, 2.0 eq.) and the solution was stirred for 10 min at 0° C. After which, the magnesium amide was transferred to a stirred solution of MTHP monoperoxyacetal (47 μL, 0.2 mmol, 1.0 eq.) in 0.5 mL anhydrous THF (0.2 M) and stirred for 15 min at 0° C. The crude mixture was subjected to flash silica column chromatography (10:90 EtOAc:Hexanes) to afford the title compound 3b (27 mg, 0.137 mmol, 68%) as a yellow oil. $R_f$=0.60 (10:90 EtOAc:Hexanes; UV, CAM). $^1$H NMR (500 MHz, CDCl$_3$): δ 7.27 (d, J=7.5 Hz, 2H), 7.21-7.15 (m, 3H), 3.70 (t, J=6.5 Hz, 2H), 3.28 (d, J=10.1 Hz, 2H), 2.67 (dd, J=8.8, 6.7 Hz, 2H), 2.36 (t, J=11.2 Hz, 2H), 1.92-1.83 (m, 2H), 1.72 (d, J=13.0 Hz, 2H), 1.58-1.54 (m, 3H), 1.15-1.09 (m, 1H). $^{13}$C NMR (126 MHz, CDCl$_3$): δ 142.3, 128.6 (2C), 128.4 (2C), 125.9, 70.8, 57.1 (2C), 32.6, 30.8, 25.7 (2C), 23.7. HRMS-ESI (m/z): [M+Na]$^+$ calculated for [C$_{14}$H$_{21}$NONa]$^+$: 220.1696, found: 220.1685.

Synthesis of hydroxylamine 3c with MTHP monoperoxyacetal (2b)

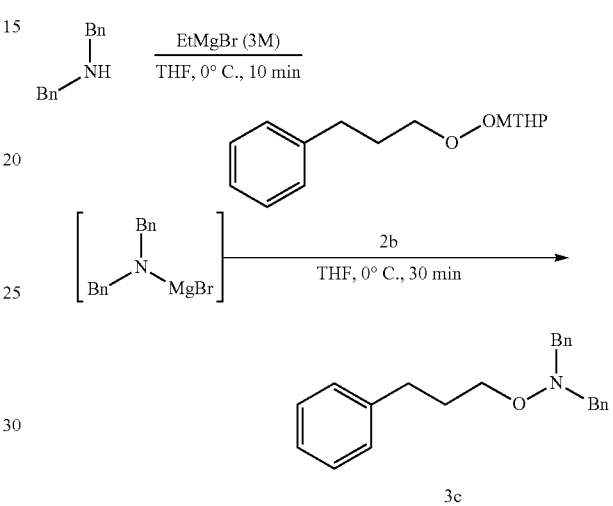

3c

Following general procedure C, dibenzylamine (96 μL, 0.5 mmol, 2.5 eq.) was treated in 0.5 mL of anhydrous THF with EtMgBr (3 M) (133 μL, 0.4 mmol, 2.0 eq.) and the solution was stirred for 10 min at 0° C. After which, the magnesium amide was transferred to a stirred solution of MTHP monoperoxyacetal (2b) (45 μL, 0.2 mmol, 1 eq.) in 0.5 mL of anhydrous THF (0.2 M) and stirred for 30 min at 0° C. The crude mixture was subjected to flash silica column chromatography (10:90 EtOAc:hexanes) to afford the title compound 3c (48 mg, 0.14 mmol, 73%) as colorless oil. $R_f$=0.65 (10:90 EtOAc:Hexanes; UV, CAM). $^1$H NMR (500 MHz, CDCl$_3$): δ 7.42-7.38 (m, 4H), 7.35-7.30 (m, 4H), 7.29-7.25 (m, 2H), 7.24-7.19 (m, 2H), 7.16-7.12 (m, 1H), 7.00 (dd, J=7.1, 1.7 Hz, 2H), 3.88 (s, 4H), 3.36 (t, J=6.3 Hz, 2H), 2.42-2.32 (m, 2H), 1.62-1.53 (m, 2H). $^{13}$C NMR (126 MHz, CDCl$_3$): δ 142.30, 138.04 (2C), 129.80 (4C), 128.45 (2C), 128.31 (2C), 128.26 (4C), 127.34 (2C), 125.71, 72.53, 62.75 (2C), 32.41, 30.28. HRMS-ESI (m/z): [M+H]$^+$ calculated for [C$_{23}$H$_{26}$NO]$^+$: 332.2009, found: 332.1993.

Synthesis of hydroxylamine 3d with MTHP monoperoxyacetal (2b)

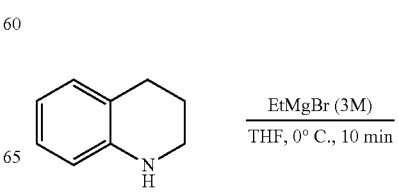

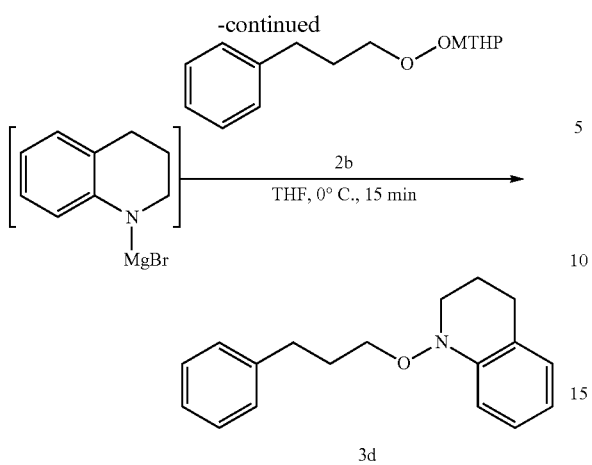

Following general procedure C, tetrahydroquinoline (63 µL, 0.5 mmol, 2.5 eq.) was treated in 0.5 mL of anhydrous THF with EtMgBr (3 M) (133 µL, 0.4 mmol, 2.0 eq.) and the solution was stirred for 10 min at 0° C., after which the magnesium amide was transferred to a stirred solution of MTHP monoperoxyacetal (2b) (43 µL, 0.2 mmol, 1 eq.) in 0.5 mL of anhydrous THF (0.2 M) and stirred for 15 min at 0° C. The crude mixture was subjected to flash silica column chromatography (10:90 EtOAc:hexanes) to afford the title compound 3d (45 mg, 0.17 mmol, 85%) as a colorless oil. $R_f$=0.70 (10:90 EtOAc:hexanes; UV, CAM). $^1$H NMR (500 MHz, CDCl$_3$): δ 7.30 (td, J=7.6, 1.7 Hz, 2H), 7.25-7.18 (m, 3H), 7.15-7.09 (m, 2H), 6.99 (d, J=7.6 Hz, 1H), 6.86-6.81 (m, 1H), 3.98 (td, J=6.6, 1.7 Hz, 2H), 3.38-3.32 (m, 2H), 2.83-2.72 (m, 4H), 2.12-2.00 (m, 4H). $^{13}$C NMR (126 MHz, CDCl$_3$): δ 148.45, 141.94, 128.98, 128.60 (2C), 128.53 (2C), 126.78, 126.03, 124.75, 121.30, 115.81, 72.74, 51.19, 32.68, 30.52, 26.48, 22.17. HRMS-ESI (m/z): [M+H]$^+$ calculated for [C$_{18}$H$_{22}$NO]$^+$: 268.1696, found: 268.1693.

Synthesis of hydroxylamine 3e with MTHP monoperoxyacetal (2b)

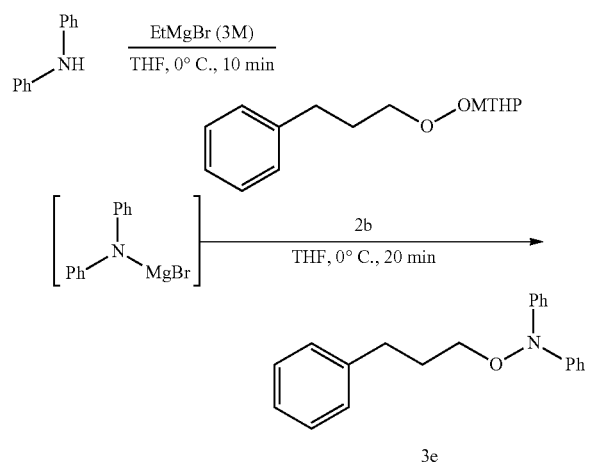

Following general procedure C, diphenylamine (85 mg, 0.5 mmol, 2.5 eq.) was treated in 0.5 mL of anhydrous THF with EtMgBr (3 M) (133 µL, 0.4 mmol, 2.0 eq.) and the solution was stirred for 10 min at 0° C. After which, the magnesium amide was transferred to a stirred solution of MTHP monoperoxyacetal (2b) (43 µL, 0.2 mmol, 1 eq.) in 0.5 mL of anhydrous THF (0.2 M) and stirred for 20 min at 0° C. The crude mixture was subjected to flash silica column chromatography (10:90 EtOAc:hexanes) to afford the title compound 3e (39 mg, 0.13 mmol, 64%) as a colorless oil. $R_f$=0.70 (10:90 EtOAc:hexanes; UV, CAM). $^1$H NMR (500 MHz, CDCl$_3$): δ 7.34-7.09 (m, 15H), 3.99 (t, J=6.4 Hz, 2H), 2.70 (dd, J=8.9, 6.7 Hz, 2H), 2.07-1.96 (m, 2H). $^{13}$C NMR (126 MHz, CDCl$_3$): δ 149.01 (2C), 141.88, 129.04 (4C), 128.59 (2C), 128.49 (2C), 125.98, 124.41 (2C), 121.01 (4C), 73.03, 32.63, 30.38. HRMS-ESI (m/z): [M+H]$^+$ calculated for [O$_{21}$H$_{22}$NO]$^+$: 304.1696, found: 304.1692.

Synthesis of hydroxylamine 3f with MTHP monoperoxyacetal (2b)

Following general procedure C, N,N-diethylamine (46 µL, 0.45 mmol, 2.5 eq.) was treated in 0.5 mL of anhydrous THF with EtMgBr (3 M) (120 µL, 0.36 mmol, 2.0 eq.) and the solution was stirred for 15 min at 0° C. After which, the magnesium amide was added dropwise to a stirred solution of MTHP monoperoxyacetal (2b) (45 mg, 0.18 mmol, 1.0 eq.) in 0.4 mL anhydrous THF (0.2 M) and stirred for 15 min at 0° C. The crude mixture was subjected to flash silica column chromatography (eluent: 10:90 EtOAc:Hexanes) to afford the title compound 3f (40 mg, 0.196 mmol, 98%) as a colorless oil. $R_f$=0.75 (10:90 EtOAc:Hexanes; UV, CAM). $^1$H NMR (500 MHz, CDCl$_3$): δ 7.27 (t, J=7.6 Hz, 2H), 7.22-7.13 (m, 3H), 3.73 (t, J=6.6 Hz, 2H), 2.72 (q, J=7.1 Hz, 4H), 2.72-2.65 (m, 2H), 1.92-1.83 (m, 2H), 1.13 (t, J=7.2 Hz, 6H). $^{13}$C NMR (126 MHz, CDCl$_3$): δ 142.3, 128.6 (2C), 128.5 (2C), 125.9, 73.6, 52.9 (2C), 32.9, 30.8, 12.5 (2C). HRMS-ESI (m/z): [M+H]$^+$ calculated for [C$_{13}$H$_{22}$NO]$^+$: 208.1696, found: 208.1690.

Synthesis of hydroxylamine 3q with MTHP monoperoxyacetal (2b)

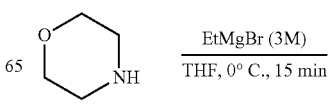

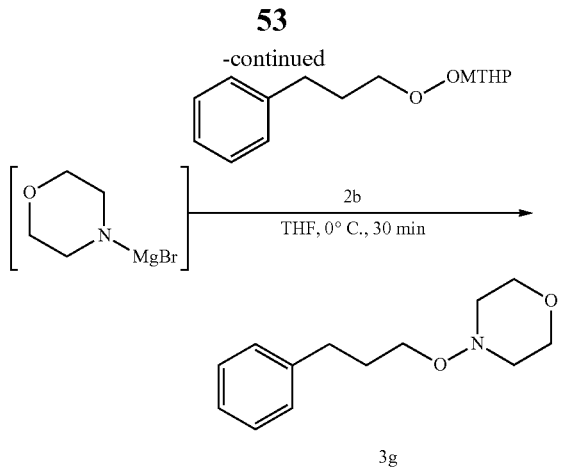

Following general procedure C, morpholine (44 μL, 0.5 mmol, 2.5 eq.) was treated in 0.5 mL of anhydrous THF with EtMgBr (3 M) (133 μL, 0.4 mmol, 2.0 eq.) and the solution was stirred for 15 min at 0° C., after which the magnesium amide was added to a stirred solution of MTHP monoperoxyacetal (2b) (50 mg, 0.2 mmol, 1 eq.) in 0.5 mL of anhydrous THF (0.2 M) and stirred for 30 min at 0° C. The crude mixture was subjected to flash silica column chromatography (10% EtOAc:hexanes) to afford the title compound 3 g (34.5 mg, 0.156 mmol, 81%) as a colorless oil. Rf=0.70 (25% EtOAc:hexanes; UV, CAM). $^1$H NMR (500 MHz, CDCl$_3$): δ 7.27 (dd, J=8.3, 6.9 Hz, 2H), 7.18 (d, J=7.4 Hz, 3H), 3.88 (d, J=11.6 Hz, 2H), 3.71 (t, J=6.6 Hz, 2H), 3.58 (t, J=11.7 Hz, 2H), 3.14 (d, J=10.5 Hz, 2H), 2.68 (d, J=7.5 Hz, 2H), 2.68-2.61 (m, 2H), 1.93-1.84 (m, 2H). $^{13}$C NMR (126 MHz, CDCl$_3$): δ 142.14, 128.66 (2C), 128.55 (2C), 126.02, 70.82, 66.51 (2C), 56.60 (2C), 32.59, 30.69. HRMS-ESI (m/z): [M+H]$^+$ calculated for [C$_{13}$H$_{20}$NO$_2$]$^+$: 222.1489, found: 222.1482.

Synthesis of hydroxylamine 3h with MTHP monoperoxyacetal (2b)

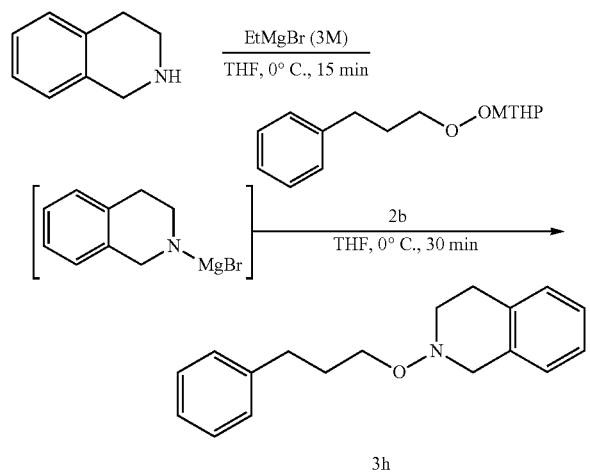

Following general procedure C, 1,2,3,4-tetrahydroisoquinoline (63 μL, 0.5 mmol, 2.5 equiv.) was treated in 0.5 mL of anhydrous THF with EtMgBr (3 M) (133 μL, 0.4 mmol, 2.0 eq.) and the solution was stirred for 15 min at 0° C., after which the magnesium amide solution was added to a stirred solution of MTHP monoperoxyacetal (2b) (50 mg, 0.2 mmol, 1.0 eq.) in 0.5 mL of anhydrous THF (0.2 M) and stirred for 30 min at 0° C. The crude mixture was subjected to flash column chromatography on neutral alumina (100:0-98:2 hexanes:EtOAc) to afford the title compound 3h (26 mg, 0.1 mmol, 50%) as a colorless oil. R$_f$=0.45 (10% EtOAc:hexanes; UV, CAM). $^1$H NMR (500 MHz, CDCl$_3$, 45° C.) δ 7.31-7.24 (m, 2H), 7.23-7.16 (m, 3H), 7.15-7.11 (m, 2H), 7.10-7.08 (m, 1H), 7.06-7.00 (m, 1H), 4.08 (br s, 2H), 3.81 (t, J=6.5 Hz, 2H), 3.19 (br s, 1H), 2.99 (t, J=6.13 Hz, 2H), 2.71 (dd, J=8.8, 6.7 Hz, 2H), 2.00-1.90 (m, 2H). $^{13}$C NMR (126 MHz, CDCl$_3$, 45° C.): δ 42.23, 133.86 (2C), 133.65 (2C), 128.69, 128.55, 128.47, 127.15, 126.70, 126.13, 126.00, 71.35, 58.37, 53.45, 32.67, 30.79, 28.57. HRMS-ESI (m/z): [M+H]$^+$ calculated for [C$_{18}$H$_{22}$NO]$^+$: 268.1696, found: 268.1693.

Synthesis of hydroxylamine 3i with MTHP monoperoxyacetal (2b)

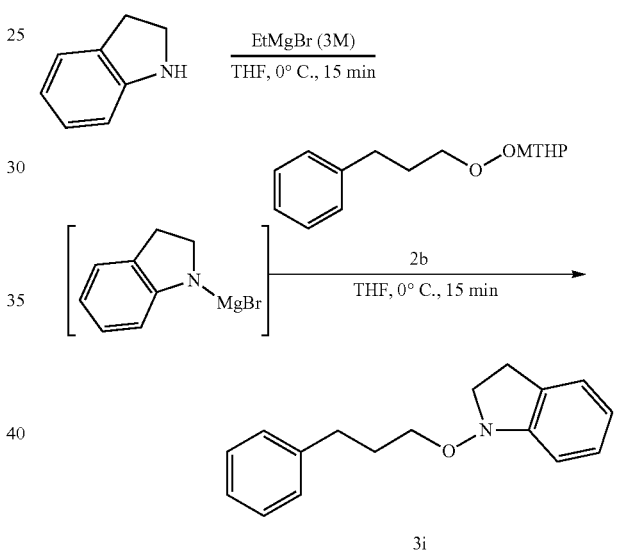

Following general procedure C, indoline (28 μL, 0.25 mmol, 2.5 equiv.) was treated in 0.25 mL of anhydrous THF with EtMgBr (3 M in diethyl ether) (66 μL, 0.2 mmol, 2.0 eq.) and the solution was stirred for 15 min at 0° C. After which, the magnesium amide was added to a stirred solution of MTHP monoperoxyacetal (2b) (26 mg, 0.1 mmol, 1.0 eq.) in 0.25 mL of anhydrous THF (0.2 M) and stirred for 15 min at 0° C. The crude mixture was subjected to flash column chromatography on neutral alumina (100:0-98:2 hexanes:EtOAc) to afford the title compound 3i (25 mg, 0.096 mmol, 96%) as a colorless oil. R$_f$=0.45 (10% EtOAc:Hexanes; UV, CAM). $^1$H NMR (500 MHz, CDCl$_3$): δ 7.31-7.11 (m, 7H), 6.98 (d, J=7.7 Hz, 1H), 6.91 (td, J=7.4, 1.1 Hz, 1H), 4.03 (t, J=6.6 Hz, 2H), 3.54 (t, J=7.6 Hz, 2H), 2.91 (t, J=7.6 Hz, 2H), 2.80-2.66 (m, 2H), 2.10-2.01 (m, 2H). $^{13}$C NMR (126 MHz, CDCl$_3$): δ 152.95, 142.02, 128.64 (2C), 128.54 (2C), 128.19, 127.50, 126.02, 124.77, 122.66, 113.34, 73.94, 58.01, 32.55, 30.95, 29.86, 27.89. HRMS-ESI (m/z): [M+H]$^+$ calculated for [C$_{17}$H$_{20}$NO]$^+$: 254.1539, found: 254.1531.

Synthesis of hydroxylamine 3i with MTHP monoperoxyacetal (2b)

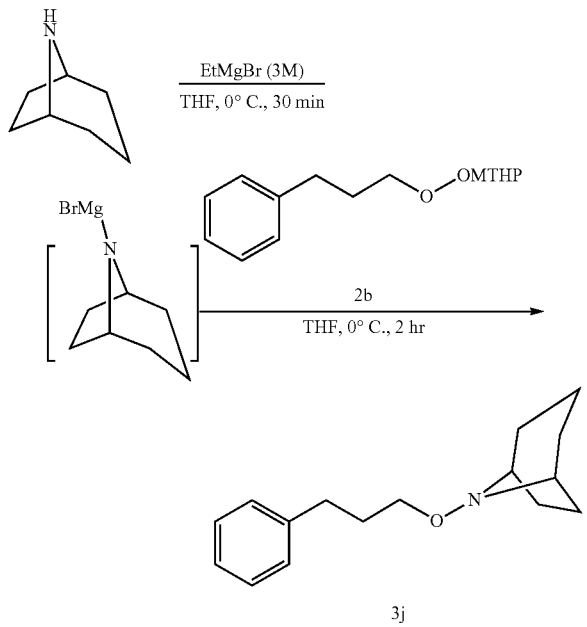

Following general procedure C, 8-azabicyclo[3.2.1]octane (55.5 mg, 0.5 mmol, 2.5 equiv.) was treated in 0.5 mL of anhydrous THF with EtMgBr (3 M) (133 µL, 0.4 mmol, 2.0 eq.) and the reaction mixture was stirred for 30 min at 0° C. After which, the magnesium amide was engaged dropwise to a stirred solution of MTHP monoperoxyacetal (2b) (50 mg, 0.2 mmol, 1.0 eq.) in 0.5 mL of anhydrous THF (0.2 M) and stirred for 2 hr at 0° C. The crude mixture was subjected to flash column chromatography on neutral alumina (100:0-96:4 hexanes:EtOAc) to afford the title compound 3j (37.5 mg, 0.153 mmol, 77%) as a colorless oil. $R_f$=0.3 (10% EtOAc:hexanes; CAM). $^1$H NMR (500 MHz, CDCl$_3$): δ 7.29-7.23 (m, 2H), 7.22-7.13 (m, 3H), 3.68 (t, J=6.4 Hz, 2H), 3.53 (p, J=3.2 Hz, 2H), 2.64 (dd, J=8.9, 6.8 Hz, 2H), 2.05-1.99 (m, 1H), 2.02-1.94 (m, 1H), 1.87 (dq, J=9.4, 6.6 Hz, 2H), 1.70 (ddd, J=14.1, 10.2, 4.3 Hz, 2H), 1.54-1.42 (m, 4H), 1.38-1.22 (m, 2H). $^{13}$C NMR (126 MHz, CDCl$_3$): δ 142.46, 128.60 (2C), 128.42 (2C), 125.81, 70.84, 64.29 (2C), 32.67, 32.20 (2C), 30.90, 27.09 (2C), 15.61. HRMS-ESI (m/z): [M+H]$^+$ calculated for [C$_{16}$H$_{24}$NO]$^+$: 246.1852, found: 246.1852.

Synthesis of hydroxylamine 3 k with MTHP monoperoxyacetal (2c)

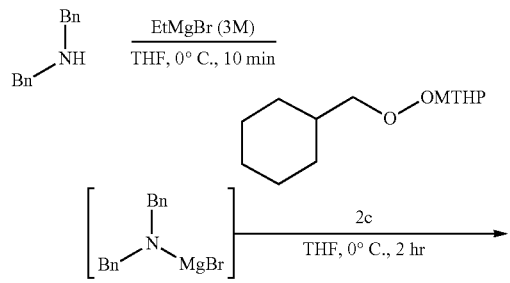

Following general procedure C, dibenzylamine (95 µL, 0.5 mmol, 2.5 eq.) was treated in 0.5 mL of anhydrous THF with EtMgBr (3 M) (133 µL, 0.4 mmol, 2.0 eq.) and the solution was stirred for 10 min at 0° C. After which, the magnesium amide was transferred to a stirred solution of MTHP monoperoxyacetal (2c) (46 µL, 0.2 mmol, 1 eq.) in 0.5 mL of anhydrous THF (0.2 M) and stirred for 2 hr at 0° C. The crude mixture was subjected to flash silica column chromatography (10:90 EtOAc:hexanes) to afford the title compound 3 k (57 mg, 0.184 mmol, 92%) as a yellow oil. $R_f$=0.60 (10:90 EtOAc:Hexanes; UV, CAM). $^1$H NMR (500 MHz, CDCl$_3$): δ 7.41-7.35 (m, 4H), 7.37-7.24 (m, 4H), 7.27-7.22 (m, 2H), 3.84 (s, 4H), 3.13 (d, J=6.4 Hz, 2H), 1.80-1.67 (m, 1H), 1.55 (m, 3H), 1.50-1.42 (m, 2H), 1.34-1.16 (m, 1H), 1.12-1.01 (m, 2H), 0.72-0.60 (m, 2H). $^{13}$C NMR (126 MHz, CDCl3): δ 138.07 (2C), 129.82 (4C), 128.19 (4C), 127.25 (2C), 79.04, 62.55 (2C), 37.14, 30.20 (2C), 26.66, 25.95 (2C). HRMS-ESI (m/z): [M+H]$^+$ calculated for [C$_{21}$H$_{28}$NO]$^+$: 310.2125, found: 310.2123.

Synthesis of hydroxylamine 3l with MTHP monoperoxyacetal (2e)

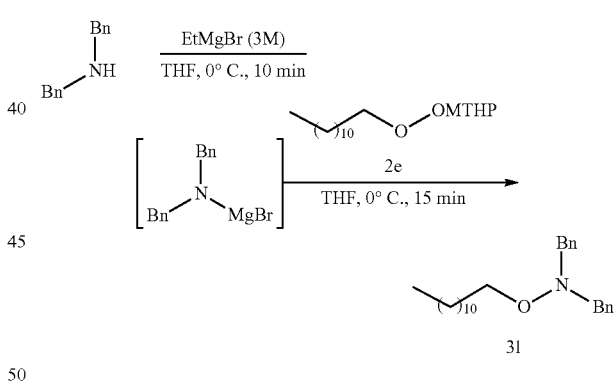

Following GP-C, dibenzylamine (95 µL, 0.5 mmol, 2.5 eq.) was treated in 0.5 mL of anhydrous THF with EtMgBr (3 M) (133 µL, 0.4 mmol, 2.0 eq.) and the solution was stirred for 10 min at 0° C., after which the magnesium amide was transferred to a stirred solution of MTHP monoperoxyacetal (2e) (60 µL, 0.2 mmol, 1 eq.) in 0.5 mL of anhydrous THF (0.2 M) and stirred for 15 mins at 0° C. The crude mixture was subjected to flash silica column chromatography (10:90 EtOAc:hexanes) to afford the title compound 3l (58 mg, 0.152 mmol, 76%) as a clear oil. $R_f$=0.70 (10:90 EtOAc:Hexanes; UV, CAM). $^1$H NMR (500 MHz, CDCl$_3$): δ 7.38 (d, J=8.0 Hz, 4H), 7.35-7.29 (m, 4H), 7.32-7.22 (m, 2H), 3.85 (s, 4H), 3.32-3.26 (m, 2H), 1.35-1.18 (m, 16H), 1.10-1.01 (m, 4H), 0.89 (q, J=5 Hz, 3H). $^{13}$C NMR (126 MHz, CDCl$_3$): δ 138.10 (2C), 129.81 (4C), 128.20 (4C), 127.28 (2C), 73.34, 62.74 (2C), 32.08, 29.81, 29.79, 29.72, 29.66, 29.51 (2C), 28.68, 26.22, 22.84, 14.26. HRMS-ESI (m/z): [M+H]+ calculated for [C$_{26}$H$_{40}$NO]+: 382.3104, found: 382.3097.

Synthesis of hydroxylamine 3m with MTHP monoperoxyacetal (2e)

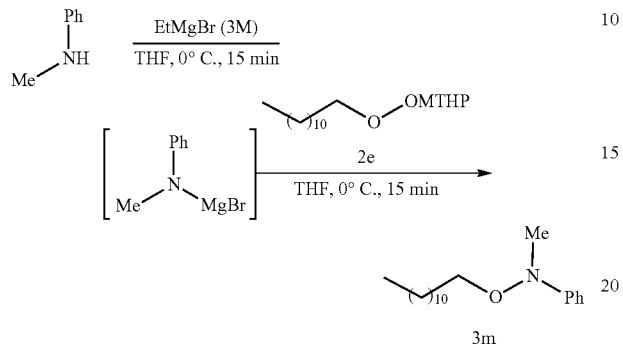

Following general procedure C, N-methylaniline (54 μL, 0.5 mmol, 2.5 equiv.) was treated in 0.5 mL of anhydrous THF with EtMgBr (3 M) (133 μL, 0.4 mmol, 2.0 equiv.) and the solution was stirred for 15 min at 0° C. After which, the magnesium amide was transferred dropwise to a stirred solution of MTHP monoperoxyacetal (2e) (60 mg, 0.2 mmol, 1 eq.) in 0.5 mL of anhydrous THF (0.2 M) and stirred for 15 mins at 0° C. The crude mixture was subjected to flash silica column chromatography (100:0-98:2 hexanes:EtOAc) to afford the title compound 3m (52 mg, 0.178 mmol, 89%) as a clear oil. R$_f$=0.66 (10:90 EtOAc:hexanes; UV, CAM). $^1$H NMR (500 MHz, CDCl3): δ 7.30-7.24 (m, 2H), 7.05-6.99 (m, 2H), 6.94 (td, J=7.2, 1.2 Hz, 1H), 3.82 (t, J=6.7 Hz, 2H), 3.05 (s, 3H), 1.65 (dt, J=15.0, 6.8 Hz, 2H), 1.44-1.34 (m, 2H), 1.27 (d, J=18.1 Hz, 16H), 0.87 (t, J=6.9 Hz, 3H). $^{13}$C NMR (126 MHz, CDCl3): δ 153.02, 128.97 (2C), 121.82, 115.80 (2C), 77.41, 77.16, 76.90, 73.12, 44.47, 32.08, 29.81, 29.79, 29.76, 29.74, 29.69, 29.50, 28.75, 26.43, 22.84, 14.26. HRMS-ESI (m/z): [M+H]+ calculated for [C$_{19}$H$_{34}$NO]+: 292.2635, found: 292.2635.

Synthesis of hydroxylamine 3n with MTHP monoperoxyacetal (2e)

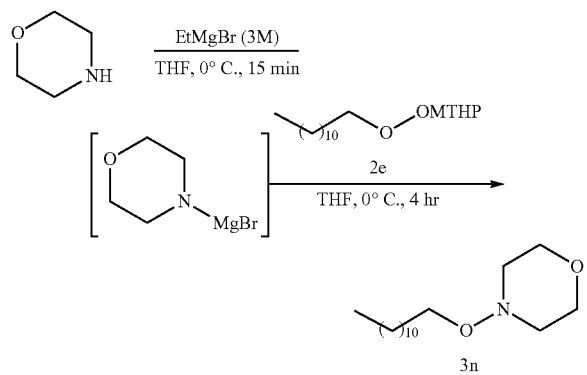

Following general procedure C, morpholine (44 μL, 0.5 mmol, 2.5 eq.) was treated in 0.5 mL of anhydrous THF with EtMgBr (3 M in diethyl ether) (133 μL, 0.4 mmol, 2.0 eq.) and the solution was stirred for 15 min at 0° C. After which, the magnesium amide was added dropwise to a stirred solution of MTHP monoperoxyacetal (2e) (60 mg, 0.2 mmol, 1.0 eq.) in 0.5 mL of anhydrous THF (0.2 M) and stirred for 4 h at 0° C. The crude product mixture was subjected to flash column chromatography on silica (eluent: 100:0-96:4 Hexanes:EtOAc) to afford the title compound 3n (29 mg, 0.11 mmol, 53%) as a colorless oil. R$_f$=0.28 (10:90 EtOAc:Hexanes; CAM). $^1$H NMR (500 MHz, CDCl3): δ 3.86 (d, J=6.7 Hz, 2H), 3.57 (t, J=11.4 Hz, 2H), 3.12 (d, J=10.5 Hz, 2H), 2.66-2.58 (m, 2H), 1.52 (q, J=7.0 Hz, 2H), 1.25 (d, J=10.6 Hz, 18H), 0.86 (t, J=6.8 Hz, 3H). $^{13}$C NMR (126 MHz, CDCl3): δ 71.7, 66.4 (2C), 56.5 (2C), 32.1, 29.8 (2C), 29.7 (2C), 29.6, 29.5, 29.0, 26.3, 22.8, 14.2. HRMS-ESI (m/z): [M+H]+ calculated for [C$_{16}$H$_{34}$NO$_2$]+: 272.2584, found: 272.2581.

Synthesis of hydroxylamine 3o with MTHP monoperoxyacetal (2d)

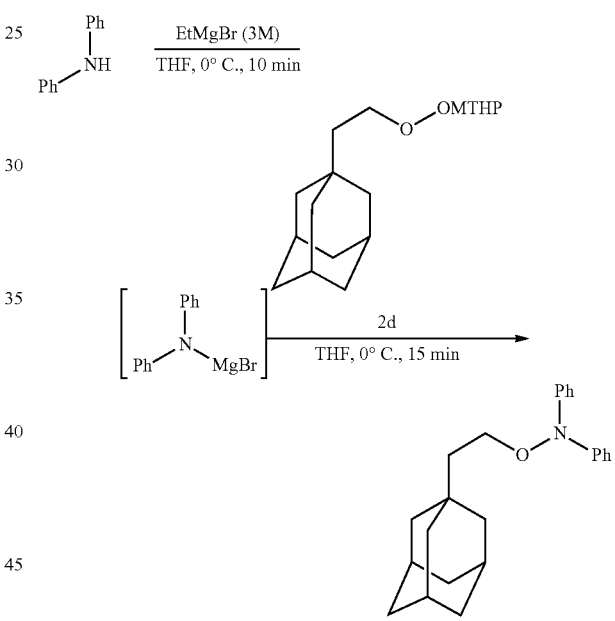

Following general procedure C, diphenylamine (85 mg, 0.5 mmol, 2.5 eq.) was treated in 0.5 mL of anhydrous THF with EtMgBr (3M in diethyl ether) (133 μL, 0.4 mmol, 2.0 eq.) and the solution was stirred for 10 min at 0° C., after which the magnesium amide was transferred to a stirred solution of MTHP monoperoxyacetal (2d) (58 mg, 0.2 mmol, 1.0 eq.) in 0.5 mL anhydrous THF (0.2 M) and stirred for 15 min at 0° C. The crude mixture was subjected to flash column chromatography on silica (eluent: 10:90 EtOAc:Hexanes) to afford the title compound 3o (58 mg, 0.167 mmol, 83%) as a clear oil. R$_f$=0.80 (10:90 EtOAc:Hexanes; UV, CAM). $^1$H NMR (500 MHz, CDCl3): δ 7.33-7.28 (m, 4H), 7.15-7.11 (m, 4H), 7.09 (td, J=7.3, 1.3 Hz, 2H), 4.04-3.96 (m, 2H), 1.92 (p, J=3.1 Hz, 3H), 1.68 (dt, J=12.1, 3.3 Hz, 3H), 1.60 (dq, J=12.3, 2.1 Hz, 3H), 1.50 (t, J=3.6 Hz, 8H). $^{13}$C NMR (126 MHz, CDCl3): δ 148.9 (2C), 129.0 (4C), 124.2 (2C), 120.9 (4C), 69.9, 42.8 (3C), 42.2, 37.2

(3C), 31.9, 28.8 (3C). HRMS-ESI (m/z): [M+Na]+ calculated for [C$_{24}$H$_{29}$NONa]+: 370.2141, found: 370.2124.

Synthesis of hydroxylamine 3p with MTHP monoperoxyacetal (2d)

Synthesis of hydroxylamine 3q with MTHP monoperoxyacetal (2d)

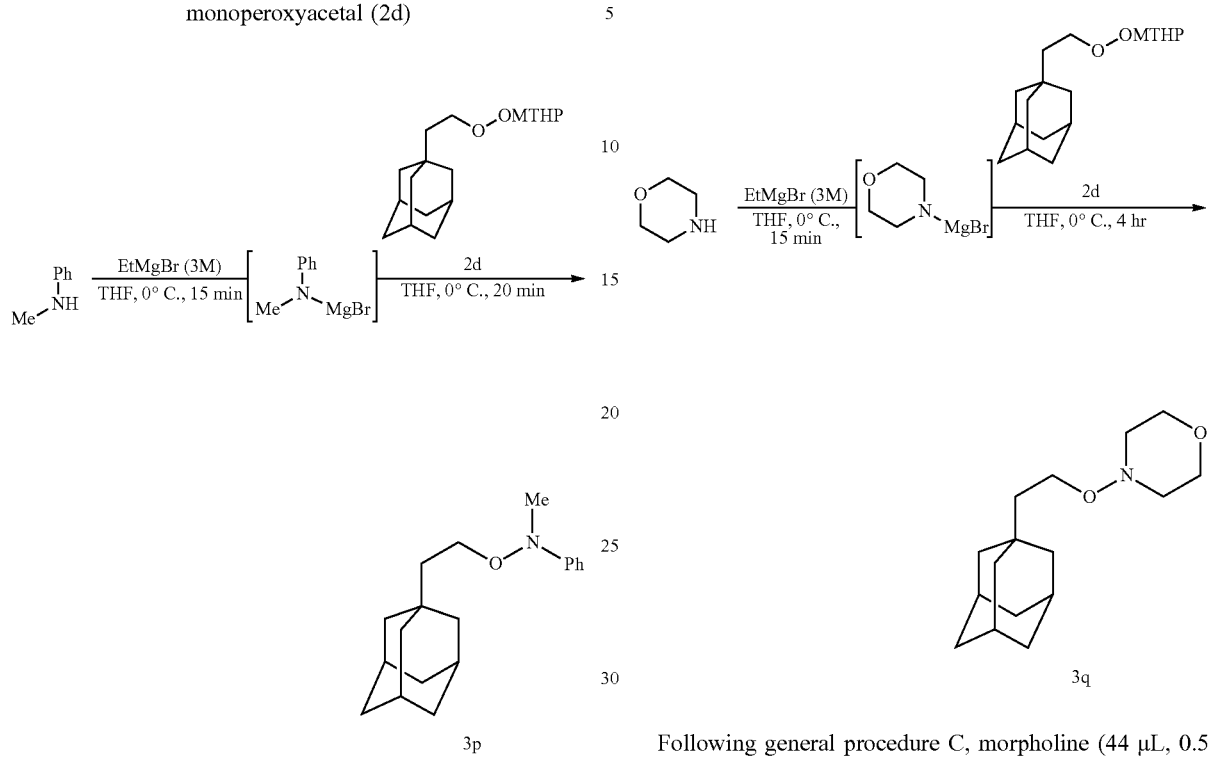

3p

3q

Following general procedure C, N-methylaniline (68 μL, 0.625 mmol, 2.5 eq.) was treated in 0.5 mL of anhydrous THF with EtMgBr (3 M) (166 μL, 0.5 mmol, 2.0 eq.) and the solution was stirred for 15 min at 0° C. After which, the magnesium amide was transferred dropwise to a stirred solution of MTHP monoperoxyacetal (2d) (71.4 mg, 0.25 mmol, 1.0 eq.) in 0.75 mL of anhydrous THF (0.2 M) and stirred for 20 min at 0° C. The crude mixture was subjected to flash silica column chromatography (100:0-96:4 Hexanes:EtOAc) to afford the title compound 3p (63.5 mg, 0.223, 89%) as a clear oil. R$_f$=0.55 (10:90 EtOAc:Hexanes; UV, CAM). $^1$H NMR (500 MHz, CDCl$_3$): δ 7.29 (dd, J=8.7, 7.1 Hz, 2H), 7.07-7.00 (m, 2H), 6.99-6.92 (m, 1H), 3.93-3.87 (m, 2H), 3.07 (s, 3H0, 1.96 (p, J=3.1 Hz, 3H), 1.75-1.60 (m, 6H), 1.56 (d, J=3.1 Hz, 6H), 1.51-1.46 (m, 2H). $^{13}$C NMR (126 MHz, CDCl$_3$): δ 152.9, 128.9 (2C), 121.8, 115.8 (2C), 68.9, 44.6, 42.9 (3C), 42.4, 37.2 (3C), 31.8, 28.8 (3C). HRMS-ESI (m/z): [M+H]+ calculated for [C$_{19}$H$_{28}$NO]+: 286.2165, found: 286.2187.

Following general procedure C, morpholine (44 μL, 0.5 mmol, 2.5 equiv) was treated in 0.5 mL of anhydrous THF with EtMgBr (3 M) (133 μL, 0.4 mmol, 2.0 equiv) and the solution was stirred for 15 min at 0° C., after which the magnesium amide was added dropwise to a stirred solution of MTHP monoperoxyacetal (2d) (59 mg, 0.2 mmol, 1 eq.) in 0.5 mL of anhydrous THF (0.2 M) and stirred for 4 hr at 0° C. The crude mixture was subjected to flash silica column chromatography (100:0-96:4 hexanes:EtOAc) to afford the title compound 3q (38 mg, 0.14 mmol, 72%) as a colorless oil. R$_f$=0.20 (10% EtOAc:hexanes; CAM). $^1$H NMR (500 MHz, CDCl$_3$): δ 3.91-3.83 (m, 2H), 3.77-3.71 (m, 2H), 3.57 (t, J=11.5 Hz, 2H), 3.14 (d, J=10.5 Hz, 2H), 2.65-2.57 (m, 2H), 1.91 (p, J=3.1 Hz, 3H), 1.67 (dt, J=12.3, 3.2 Hz, 3H), 1.63-1.56 (m, 3H), 1.49 (d, J=2.9 Hz, 6H), 1.32 (t, J=7.5 Hz, 2H). $^{13}$C NMR (126 MHz, CDCl3): δ 67.37, 66.43 (2C), 56.48 (2C), 42.88 (3C), 42.75, 37.25 (3C), 31.87, 28.81 (3C). HRMS-ESI (m/z): [M+H]+ calculated for [C$_{16}$H$_{28}$NO$_2$]+: 266.2115; found: 266.2083.

Synthesis of hydroxylamine 3r with MTHP monoperoxyacetal (2d)

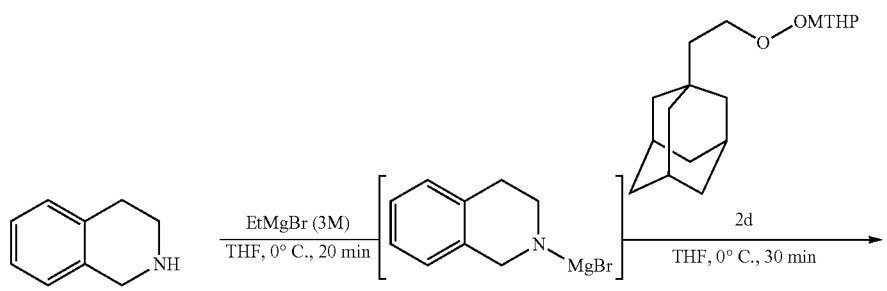

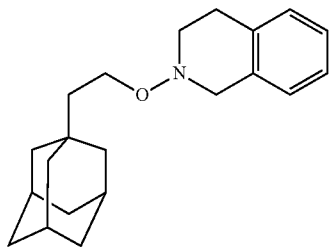

3r

Following general procedure C, 1,2,3,4-tetrahydroisoquinoline (63 μL, 0.5 mmol, 2.5 eq.) was treated in 0.5 mL of anhydrous THF with EtMgBr (3 M) (133 μL, 0.4 mmol, 2.0 eq.) and the solution was stirred for 20 min at 0° C. After which, the magnesium amide was added dropwise to a stirred solution of MTHP monoperoxyacetal (2d) (58 mg, 0.2 mmol, 1.0 eq.) in 0.5 mL anhydrous THF (0.2 M) and stirred for 30 min at 0° C. The crude mixture was subjected to flash silica column chromatography (eluent: 100:0-98:2 Hexanes:EtOAc) to afford the title compound 3r (57.3 mg, 0.184 mmol, 92%) as a colorless oil. $R_f$=0.40 (10:90 EtOAc:Hexanes;CAM). $^1$H NMR (500 MHz, CDCl$_3$, T=343 K) (Due to the presence of rotamers, the spectra was obtained at 343 K): δ 7.11 (q, J=4.7 Hz, 2H), 7.07 (q, J=4.8 Hz, 1H), 7.04-6.99 (m, 1H), 4.21-3.97 (m, 2H), 3.85 (m, 2H), 3.26 (m, 2H), 2.98 (m, 2H), 1.97-1.90 (m, 3H), 1.70 (d, J=12.1 Hz, 3H), 1.62 (m, 3H), 1.53 (d, J=2.9 Hz, 6H), 1.40 (t, J=2H). $^{13}$C NMR (126 MHz, CDCl$_3$): δ 133.8, 133.6, 128.4, 127.1, 126.6, 126.0, 67.9, 58.3, 53.4, 42.9 (3C), 37.3 (3C), 31.9, 28.8 (3C), 28.6. HRMS-ESI (m/z): [M+H]$^+$ calculated for [C$_{21}$H$_{30}$NO]$^+$: 312.2322, found: 312.2321.

Synthesis of hydroxylamine 3s with MTHP monoperoxyacetal (2d)

Following general procedure C, dibenzylamine (95 μL, 0.5 mmol, 2.5 eq.) was treated in 0.5 mL of anhydrous THF with EtMgBr (3 M) (133 μL, 0.4 mmol, 2.0 eq.) and the solution was stirred for 10 min at 0° C., after which the magnesium amide was transferred to a stirred solution of MTHP monoperoxyacetal (2d) (58 μL, 0.2 mmol, 1 eq.) in 0.5 mL of anhydrous THF (0.2 M) and stirred for 20 mins at 0° C. The crude mixture was subjected to flash silica column chromatography (10:90 EtOAc:hexanes) to afford the title compound 3s (69 mg, 0.183 mmol, 91%) as a clear oil. $R_f$=0.80 (10:90 EtOAc:hexanes; UV, CAM). $^1$H NMR (500 MHz, CDCl$_3$): δ 7.40-7.36 (m, 4H), 7.33-7.29 (m, 4H), 7.27-7.22 (m, 2H), 3.83 (s, 4H), 3.33 (t, J=7.3 Hz, 2H), 1.81 (p, J=3.2 Hz, 3H), 1.60 (dt, J=12.6, 2.4 Hz, 3H), 1.50 (dq, J=12.5, 2.0 Hz, 3H), 1.23 (d, J=2.9 Hz, 6H), 1.03 (t, J=7.3 Hz, 2H). $^{13}$C NMR (126 MHz, CDCl$_3$): δ 138.16 (2C), 129.77 (4C), 128.22 (4C), 127.28 (2C), 69.15, 62.75 (2C), 42.55 (3C), 42.39, 37.17 (3C), 31.55, 28.75 (3C). HRMS-ESI (m/z): [M+Na]$^+$ calculated for [C$_{26}$H$_{33}$NONa]$^+$: 398.2430, found 398.2436.

Synthesis of hydroxylamine 3t with MTHP monoperoxyacetal (2f)

Following general procedure C, morpholine (43 μL, 0.5 mmol, 2.5 eq.) was treated in 0.5 mL of anhydrous THF with EtMgBr (3 M) (133 μL, 0.4 mmol, 2.0 eq.) and the solution was stirred for 15 min at 0° C. After which, the magnesium amide was transferred to a stirred solution of MTHP monoperoxyacetal (20 (51 mg, 0.2 mmol, 1.0 eq.) in 0.5 mL of anhydrous THF (0.2 M) and stirred for 1 h at 0° C. The crude mixture was subjected to flash column chromatography on silica (eluent: 100:0-92:8 Hexanes:EtOAc) to afford the title compound 3t (33 mg, 0.153 mmol, 76%) as a colorless oil. $R_f$=0.25 (10:90 EtOAc:Hexanes;CAM). $^1$H NMR (500 MHz, CDCl$_3$): δ 3.84 (d, J=8.5 Hz, 2H), 3.71 (q, J=6.1 Hz, 1H), 3.60 (d, J=11.5 Hz, 2H), 3.05 (d, J=10.4 Hz, 2H), 2.64 (q, J=11.9 Hz, 2H), 1.50 (tdd, J=8.2, 6.8, 6.0, 3.8 Hz, 1H), 1.39-1.28 (m, 2H), 1.27 (m, 6H), 1.13 (d, J=6.2 Hz, 3H), 0.87 (t, J=6.8 Hz, 3H). $^{13}$C NMR (126 MHz, CDCl$_3$): δ 77.2 (2C), 66.5, 57.6, 56.8, 35.8, 32.0, 29.6, 25.8, 22.8, 20.1, 14.2. HRMS-ESI (m/z): [M+H]$^+$ calculated for [C$_{12}$H$_{25}$NO$_2$]$^+$: 216.1958, found: 216.1950.

Synthesis of hydroxylamine 3u with MTHP monoperoxyacetal (2f)

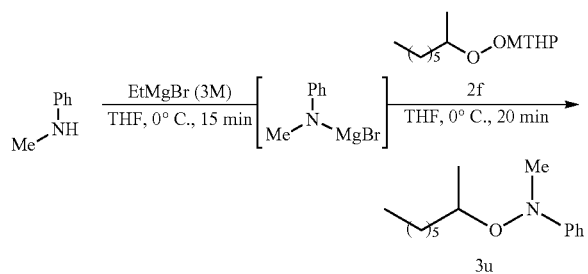

Following general procedure C, N-methylaniline (54 µL, 0.5 mmol, 2.5 eq.) was treated in 0.5 mL of anhydrous THF with EtMgBr (3 M) (133 µL, 0.4 mmol, 2.0 eq.) and the reaction mixture was stirred for 15 min at 0° C. After which, the magnesium amide was transferred to a stirred solution of MTHP monoperoxyacetal (20 (50 mg, 0.2 mmol, 1.0 eq.) in 0.5 mL of anhydrous THF (0.2 M) and stirred for 15 min at 0° C. The crude mixture was subjected to flash column chromatography on silica (eluent: 100:0-92:8 Hexanes:EtOAc) to afford the title compound 3u (32.5 mg, 0.138 mmol, 69%) as a colorless oil. $R_f$=0.46 (10:90 EtOAc:Hexanes;UV, CAM). $^1$H NMR (500 MHz, CDCl$_3$): δ 7.30-7.22 (m, 2H), 7.07-6.99 (m, 2H), 6.92 (tt, J=7.3, 1.2 Hz, 1H), 3.84 (p, J=6.0 Hz, 1H), 3.04 (s, 3H), 1.69 (m, 1H), 1.50-1.32 (m, 2H), 1.30 (s, 7H), 1.22 (d, J=6.1 Hz, 3H), 0.92-0.84 (m, 3H). $^{13}$C NMR (126 MHz, CDCl$_3$): δ 153.8, 128.8 (2C), 121.6, 116.0 (2C), 78.2, 45.6, 35.5, 32.0, 29.6, 25.8, 22.8, 19.4, 14.2. HRMS-ESI (m/z): [M+H]$^+$ calculated for [C$_{15}$H$_{26}$NO]$^+$: 236.2009, found: 236.2005.

Synthesis of hydroxylamine 3v with MTHP monoperoxyacetal (2q)

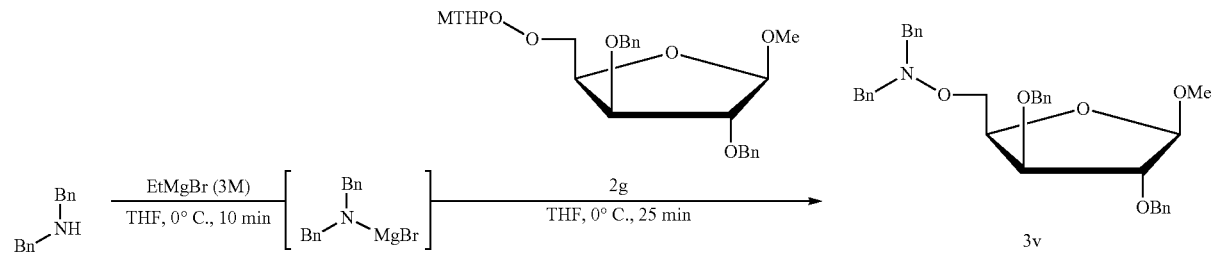

Following general procedure C, dibenzylamine (48 µL, 0.25 mmol, 2.5 eq.) was treated in 0.25 mL of anhydrous THF with EtMgBr (3 M) (66 µL, 0.2 mmol, 2.0 eq.) and the solution was stirred for 10 min at 0° C., after which the magnesium amide was transferred to a stirred solution of MTHP monoperoxyacetal (2 g) (45 mg, 0.1 mmol, 1 eq.) in 0.25 mL of anhydrous THF (0.2 M) and stirred for 25 mins at 0° C. The crude mixture was subjected to flash silica column chromatography (20:80 EtOAc:hexanes) to afford the title compound 3v (36 mg, 0.067 mmol, 67%) as a clear oil. $R_f$=0.65 (30:70 EtOAc:Hexanes; UV, CAM). $^1$H NMR (500 MHz, CDCl$_3$): δ 7.38-7.18 (m, 20H), 4.79 (d, J=2 Hz, 1H), 4.44-4.41 (m, 2H), 4.36-4.27 (m, 2H), 4.16-4.13 (m, 1H), 3.92-3.85 (m, 4H), 3.83 (m, 1H), 3.76-3.70 (m, 2H), 3.59 (dd, J=11.0, 4.2 Hz, 1H), 3.28 (s, 3H). $^{13}$C NMR (126 MHz, CDCl$_3$): δ 137.96 (3C), 137.80, 129.76 (4C), 128.54 (2C), 128.84 (2C), 128.30 (4C), 127.93, 127.87 (2C), 127.84, 127.77 (2C), 127.34 (2C), 108.04, 87.09, 81.56, 78.91, 72.67, 72.12, 71.92, 62.40 (2C), 55.57. HRMS-ESI (m/z): [M+Na]$^+$ calculated for [C$_{34}$H$_{37}$NO$_5$Na]$^+$: 540.2744, found: 540.2739. [α]$_D$=−4.0° (c=1.0 g/100 mL, CHCl$_3$).

Synthesis of hydroxylamine 3w with MTHP monoperoxyacetal (2q)

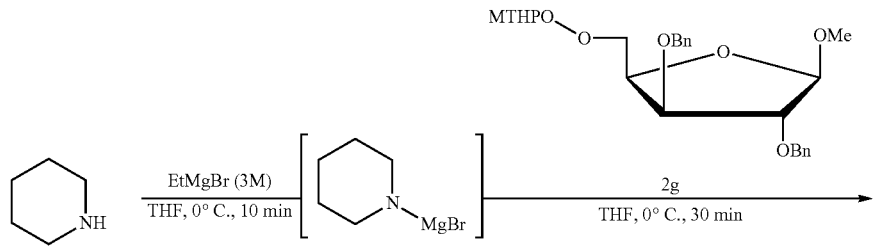

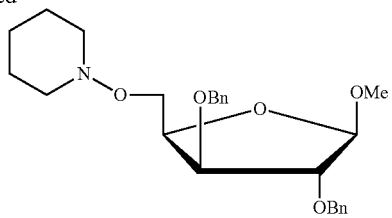

3w

Following general procedure C, piperidine (50 μL, 0.50 mmol, 2.5 eq.) was treated in 0.50 mL of anhydrous THF with EtMgBr (3 M) (133 μL, 0.4 mmol, 2.0 eq.) and the solution was stirred for 10 min at 0° C., after which the magnesium amide was transferred to a stirred solution of MTHP monoperoxyacetal (2 g) (92 mg, 0.2 mmol, 1 eq.) in 0.50 mL of anhydrous THF (0.2 M) and stirred for 30 mins at 0° C. The crude mixture was subjected to flash silica column chromatography (5% EtOAc:DCM) to afford the title compound 3w (37 mg, 0.087 mmol, 43%) as a clear oil. $R_f$=0.50 (5:95 EtOAc:DCM; UV, CAM). $^1$H NMR (500 MHz, CDCl$_3$): δ 7.36-7.25 (m, 10H), 4.90 (d, J=1.4 Hz, 1H), 4.61-4.44 (m, 4H), 4.48-4.42 (m, 1H), 4.04 (dd, J=6.0, 2.5 Hz, 1H), 4.01-3.95 (m, 2H), 3.91 (dd, J=11.0, 7.8 Hz, 1H), 3.40 (s, 3H), 3.30 (d, J=9.9 Hz, 2H), 2.38 (q, J=9.2 Hz, 2H), 1.70 (s, 2H), 1.53 (q, J=13.2, 12.4 Hz, 3H), 1.11 (m, 1H). $^{13}$C NMR (126 MHz, CDCl3): δ 138.01, 137.76, 128.58 (2C), 128.51 (2C), 127.97 (3C), 127.88 (3C), 108.11, 87.28, 81.99, 79.12, 72.34, 72.07, 71.02, 57.19, 56.73, 55.62, 25.66 (2C), 23.64. HRMS-ESI (m/z): [M+Na]$^+$ calculated for [C$_{25}$H$_{33}$NO$_5$Na]$^+$: 450.2251, found: 450.2229. [α]$_D$=−4.2° (c=1.0 g/100 mL, CHCl$_3$).

Synthesis of hydroxylamine 3x with MTHP monoperoxyacetal (2h)

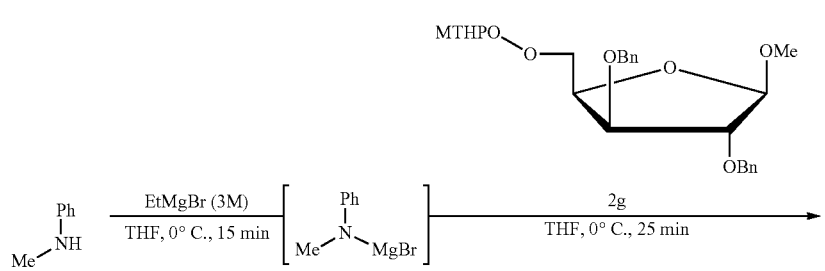

3x

Following general procedure C, N-methylaniline (38 μL, 0.35 mmol, 2.5 eq.) was treated in 0.5 mL of anhydrous THF with EtMgBr (3 M) (95 μL, 0.28 mmol, 2.0 eq.) and the solution was stirred for 15 min at 0° C. After which, the magnesium amide was transferred to a stirred solution of MTHP monoperoxyacetal (2 g) (61.5 mg, 0.14 mmol, 1.0 eq.) in 0.2 mL anhydrous THF (0.2 M) and stirred for 25 min at 0° C. The crude mixture was subjected to flash column chromatography on silica (eluent: 100:0-80:20 Hexanes: EtOAc) to afford the title compound 3x (34.5 mg, 0.077 mmol, 55%) as a colorless oil. $R_f$=0.15 (10:90 EtOAc: Hexanes; UV, CAM, H$_2$SO$_4$). $^1$H NMR (500 MHz, CDCl$_3$): δ 7.36-7.27 (m, 10H), 7.27-7.23 (m, 2H), 7.11-7.05 (m, 2H), 6.98-6.91 (m, 1H), 4.94 (d, J=1.5 Hz, 1H), 4.58 (d, J=12.2 Hz, 1H), 4.58-4.53 (m, 1H), 4.53 (d, J=4.2 Hz, 1H), 4.48 (dd, J=12.0, 3.6 Hz, 2H), 4.12 (dd, J=11.1, 4.3 Hz, 1H), 4.12-4.05 (m, 2H), 4.01 (dd, J=2.8, 1.6 Hz, 1H), 3.44 (s, 3H), 3.08 (s, 3H). $^{13}$C NMR (126 MHz, CDCl$_3$): δ 152.9, 137.8, 137.7, 128.9 (2C), 128.4 (4C), 128.1, 128.0 (3C), 127.9 (2C), 122.0, 116 (2C), 108.3, 87.1, 82.1, 78.7, 72.7, 72.4, 72.2, 55.7, 44.5. HRMS-ESI (m/z): [M+Na]$^+$ calculated for [C$_{27}$H$_1$NO$_5$Na]$^+$: 472.2094, found: 472.2085. [α]$_D$=−2.3 (c=1.0 g/100 mL, CHCl$_3$).

Synthesis of hydroxylamine 3y with MTHP monoperoxyacetal (2h)

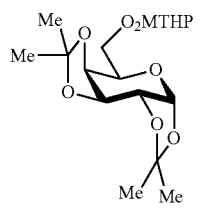

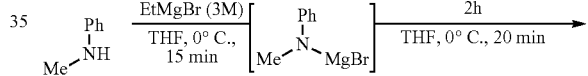

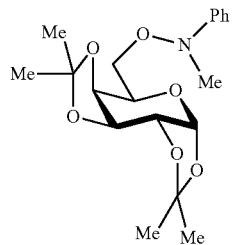

3y

Following general procedure C, N-methylaniline (27 μL, 0.25 mmol, 2.5 equiv.) was treated in 0.25 mL of anhydrous THF with EtMgBr (3M) (68 μL, 0.20 mmol, 2.0 equiv.) and the solution was stirred for 15 min at 0° C., after which the magnesium amide was transferred dropwise to a stirred solution of MTHP monoperoxyacetal (2h) (39 mg, 0.10 mmol, 1.0 eq.) in 0.25 mL of anhydrous THF (0.2 M) and stirred for 20 mins at 0° C. The crude mixture was subjected to flash silica column chromatography (100:0-85:15 hexanes:EtOAc) to afford the title compound 3y (21 mg, 0.057 mmol, 57%) as a colorless oil. $R_f$=0.15 (10% EtOAc/hexanes; UV, CAM, $H_2SO_4$). $^1$H NMR (500 MHz, CDCl3): δ 7.30-7.24 (m, 2H), 7.10-7.04 (m, 2H), 6.98-6.91 (m, 1H), 5.59 (d, J=5.1 Hz, 1H), 4.59 (dd, J=7.7, 2.4 Hz, 1H), 4.32 (dd, J=5.0, 2.5 Hz, 1H), 4.20 (ddd, J=8.0, 5.6, 2.0 Hz, 2H), 4.03-3.93 (m, 2H), 3.09 (s, 2H), 1.45 (s, 3H), 1.43 (s, 3H), 1.32 (s, 3H), 1.32 (s, 3H). $^{13}$C NMR (126 MHz, CDCl3): δ 153.07, 128.99 (2C), 122.23, 116.40 (2C), 109.65, 108.85, 96.76, 72.41, 71.91, 71.05, 70.69, 65.81, 45.30, 26.22, 25.97, 25.23, 24.75. HRMS-ESI (m/z): [M+Na]$^+$ calculated for $[C_{19}H_{27}NO_6Na]^+$: 388.1731; found: 388.1729. $[α]_D$= -5.2° (c=1.0 g/100 mL, CHCl$_3$).

Synthesis of hydroxylamine 3z with MTHP monoperoxyacetal (2h)

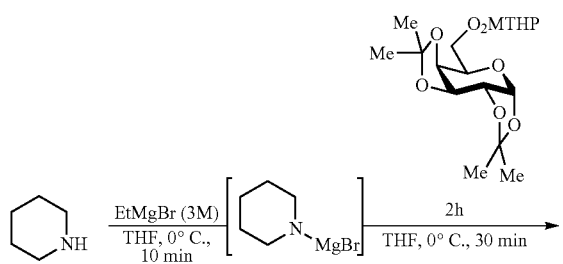

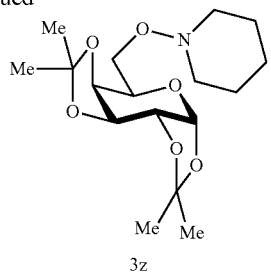

3z

Following general procedure C, piperidine (50 μL, 0.50 mmol, 2.5 eq.) was treated in 0.50 mL of anhydrous THF with EtMgBr (3 M) (133 μL, 0.4 mmol, 2.0 eq.) and the solution was stirred for 10 min at 0° C., after which the magnesium amide was transferred to a stirred solution of MTHP monoperoxyacetal (2h) (75 mg, 0.2 mmol, 1 eq.) in 0.50 mL of anhydrous THF (0.2 M) and stirred for 30 mins at 0° C. The crude mixture was subjected to flash silica column chromatography (5% EtOAc:DCM) to afford the title compound 3z (34 mg, 0.100 mmol, 50%) as a clear oil. $R_f$=0.10 (5:95 EtOAc:DCM; CAM, $H_2SO_4$). $^1$H NMR (500 MHz, CDCl$_3$): δ 5.56 (d, J=5.1 Hz, 1H), 4.58 (dd, J=7.9, 2.4 Hz, 1H), 4.30 (dd, J=5.1, 2.5 Hz, 1H), 4.21 (dd, J=10.0, 5.0 Hz, 1H), 4.17 (m, 1H), 3.84-3.74 (m, 2H), 3.38 (d, J=10.0 Hz, 1H), 3.23 (d, J=10.0 Hz, 1H), 2.36 (q, J=10 Hz, 2H), 1.68 (m, 2H), 1.55-1.46 (m, 6H), 1.42 (s, 3H), 1.32 (d, 6H), 1.10 (m, 1H). $^{13}$C NMR (126 MHz, CDCl3): δ 109.49, 108.58, 96.78, 71.80, 71.04, 70.69, 70.52, 65.51, 57.28, 56.76, 26.13, 26.07, 25.73, 25.63, 25.16, 24.74, 23.64. HRMS-ESI (m/z): [M+H]$^+$ calculated for $[C_{17}H_{30}NO_6]^+$: 344.2068; found: 344.2056. $[α]_D$=-6.5° (c=1.0 g/100 mL, CHCl$_3$).

Synthesis of hydroxylamine 3aa with MTHP monoperoxyacetal (2i)

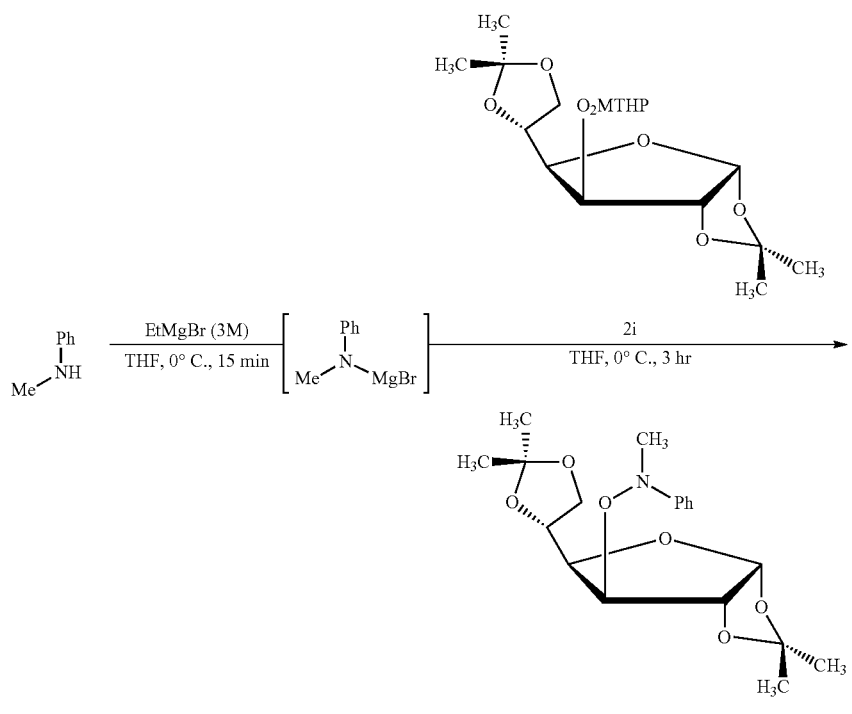

Following general procedure C, N-methylaniline (27 μL, 0.25 mmol, 2.5 equiv.) was treated in 0.25 mL of anhydrous THF with EtMgBr (3M) (68 μL, 0.20 mmol, 2.0 equiv.) and the solution was stirred for 15 min at 0° C., after which the magnesium amide was transferred dropwise to a stirred solution of MTHP monoperoxyacetal (2i) (37 mg, 0.10 mmol, 1.0 eq.) in 0.25 mL of anhydrous THF (0.2 M) and stirred for 3 hours at 0° C. The crude mixture was subjected to flash silica column chromatography (100:0-98:2-90:10 hexanes:EtOAc) to afford the title compound 3aa (15.2 mg, 0.042 mmol, 42%) as a colorless oil. $R_f$=0.12 (5% EtOAc/hexanes; UV, CAM, $H_2SO_4$). $^1$H NMR (500 MHz, CDCl$_3$): δ 7.30-7.25 (m, 2H), 7.09-7.03 (m, 2H), 7.00 (td, J=7.2, 1.2 Hz, 1H), 5.93 (d, J=3.8 Hz, 1H), 4.72 (d, J=3.8 Hz, 1H), 4.42 (dt, J=7.5, 5.9 Hz, 1H), 4.33 (d, J=3.4 Hz, 1H), 4.20 (dd, J=7.6, 3.3 Hz, 1H), 4.12 (dd, J=8.5, 6.2 Hz, 1H), 4.02 (dd, J=8.6, 5.7 Hz, 1H), 3.06 (s, 3H), 1.48 (s, 3H), 1.44 (s, 3H), 1.37 (s, 3H), 1.27 (s, 4H). $^{13}$C NMR (126 MHz, CDCl3): δ 153.02, 129.05 (2C), 122.84, 116.51 (2C), 111.92, 109.22, 105.29, 83.48, 82.40, 80.35, 72.49, 67.54, 51.33, 26.98, 26.96, 26.41, 25.60. HRMS-ESI (m/z): [M+Na]$^+$ calculated for [C$_{19}$H$_{27}$NO$_6$Na]$^+$: 388.1731; found: 388.1730. [α]$_D$= –18.5° (c=1.0 g/100 mL, CHCl$_3$).

Synthesis of hydroxylamine 3ab with MTHP monoperoxyacetal (2i)

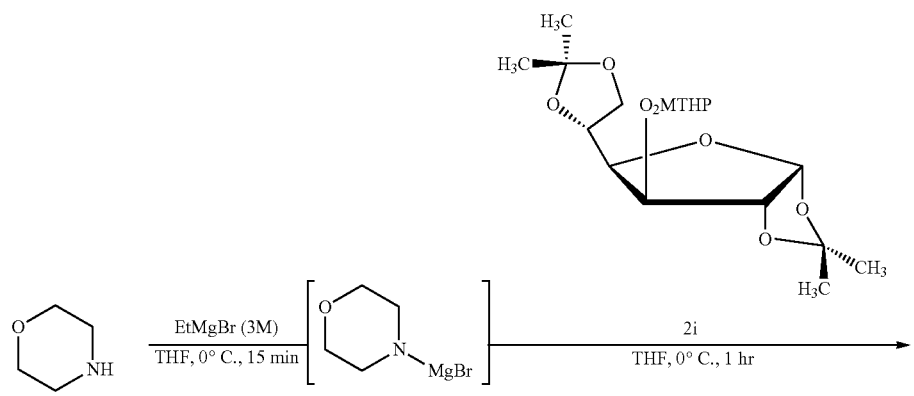

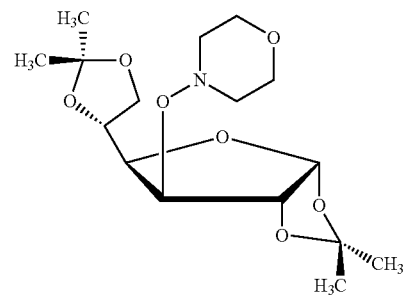

3ab

Following general procedure C, vacuum distilled morpholine (30 μL, 0.35 mmol, 2.5 eq) was treated in 0.50 mL of anhydrous THF with EtMgBr (3 M) (95 μL, 0.28 mmol, 2.0 eq) and the solution was stirred for 15 min at 0° C., after which the magnesium amide was transferred dropwise to a stirred solution of MTHP monoperoxyacetal (2i) (53 mg, 0.14 mmol, 1.0 eq.) in 0.2 mL of anhydrous THF (0.2 M) and stirred for 3 hours at 0° C. The crude mixture was subjected to flash silica column chromatography (100:0-60:40 hexanes:EtOAc) to afford the title compound 3ab (28 mg, 0.08 mmol, 58%) as a colorless oil. $R_f$=0.1 (10% EtOAc/hexanes; CAM, $H_2SO_4$). $^1$H NMR (500 MHz, CDCl$_3$): δ 5.86 (d, J=3.7 Hz, 1H), 4.68 (d, J=3.7 Hz, 1H), 4.26 (dt, J=7.5, 5.9 Hz, 1H), 4.24 (d, J=3.4 Hz, 1H), 4.13 (dd, J=7.5, 3.4 Hz, 1H), 4.06 (dd, J=8.6, 6.2 Hz, 1H), 3.94 (dd, J=8.6, 5.8 Hz, 1H), 3.88 (t, J=12.5 Hz, 2H), 3.59 (dtd, J=17.5, 11.4, 2.5 Hz, 2H), 3.21 (d, J=10.7 Hz, 1H), 3.08-3.03 (m, 1H), 2.74 (td, J=10.6, 3.3 Hz, 1H), 2.65 (td, J=10.6, 3.2 Hz, 1H), 1.49 (s, 3H), 1.41 (s, 3H), 1.33 (s, 3H), 1.32 (s, 3H). $^{13}$C NMR (126 MHz, CDCl$_3$): δ 111.95, 108.92, 105.27, 83.11, 82.94, 80.36, 72.54, 67.37, 66.23, 66.14, 57.74, 55.56, 27.00, 26.97, 26.46, 25.56. HRMS-ESI (m/z): [M+H]$^+$ calculated for $[C_{16}H_{28}NO_7]^+$: 346.1860; found: 346.1856. $[α]_D$=−5.0° (c=1.0 g/100 mL, CHCl$_3$).

Synthesis of hydroxylamine 3ac

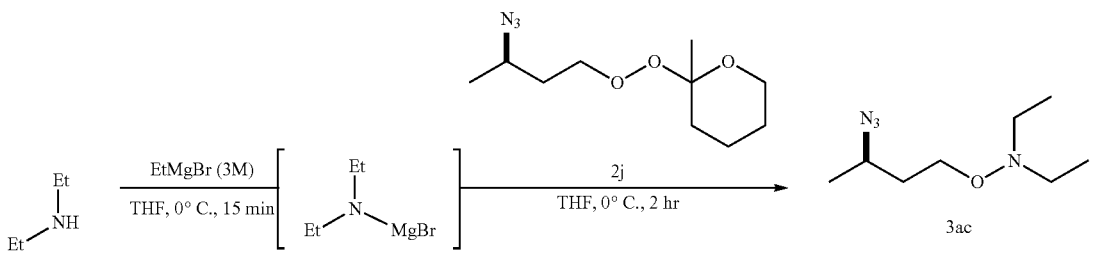

Following general procedure C, diethylamine (1.1 mL, 10.9 mmol, 2.5 eq) was treated in 11 mL of anhydrous THF with EtMgBr (3 M) (2.9 mL, 8.7 mmol, 2.0 eq) and the solution was stirred for 15 min at 0° C., after which the magnesium amide was transferred dropwise to a stirred solution of MTHP monoperoxyacetal (2j) (1 g, 4.36 mmol, 1 eq) in 11 mL of anhydrous THF (0.2 M) and stirred for 2 hr at 0° C. The crude reaction mixture was subjected to flash silica column chromatography (20:80 EtOAc:hexanes) to afford the title compound 3ac (628.9 mg, 3.38 mmol, 78%) as a colorless oil. $R_f$=0.4 (20:80 EtOAc/Hexanes; CAM). $^1$H NMR (500 MHz, CDCl$_3$): δ 3.81-3.71 (m, 2H), 3.62-3.58 (m, 1H), 2.70 (q, J=10 Hz, 4H), 1.71-1.63 (m, 2H), 1.26 (d, J=5 Hz, 3H), 1.11 (t, J=10 Hz, 6H). $^{13}$C NMR (126 MHz, CDCl$_3$): δ 70.25, 55.30, 52.72 (2C), 35.55, 19.80, 12.36 (2C). HRMS-ESI (m/z): [M+H]$^+$ calculated for $[C_8H_{19}ON_4]^+$: 187.1553; found: 187.1545. $[α]_D$=−25.0° (c=1.0 g/100 mL, CHCl$_3$).

Synthesis of hydroxylamine (3ad)

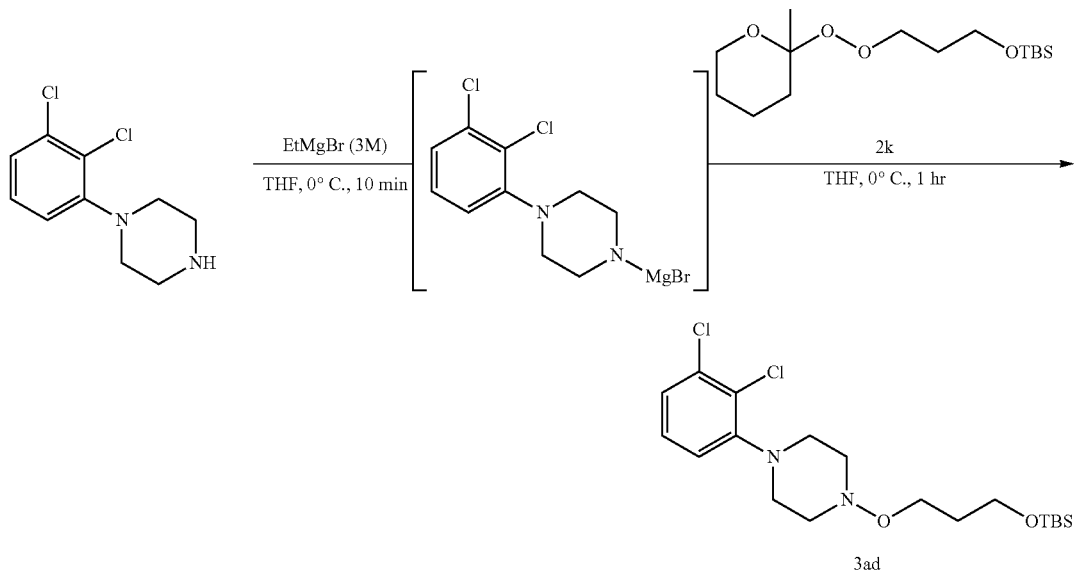

Following general procedure C, 1-(2,3-dichlorophenyl)piperazine (1.15 g, 5.0 mmol, 2.5 eq) was treated in 5 mL of anhydrous THF with EtMgBr (3 M) (1.33 mL, 4.0 mmol, 2 eq) and the solution was stirred for 10 min at 0° C. After which, the magnesium amide was transferred dropwise to a stirred solution of MTHP monoperoxyacetal (2 k) (608 mg, 2.0 mmol, 1 eq) in 5 mL of anhydrous THF (0.2 M) and stirred for 1 hr at 0° C. The crude reaction mixture was subjected to flash silica column chromatography (10:88:2 EtOAc:hexanes:Et$_3$N) to afford the title compound 3ad (728 mg, 1.74 mmol, 87%) as a yellow oil. R$_f$=0.8 (20:80 EtOAc:hexanes; CAM). $^1$H NMR (500 MHz, CDCl$_3$): δ 7.17-7.10 (m, 2H), 6.93 (dd, J=7.5, 2.0 Hz, 1H), 3.80 (t, J=6.3 Hz, 2H), 3.69 (t, J=6.2 Hz, 2H), 3.29 (m, 4H), 2.90 (m, 4H), 1.79 (p, J=6.3 Hz, 2H), 0.89 (s, 9H), 0.05 (s, 6H). $^{13}$C NMR (126 MHz, CDCl$_3$): δ 150.93, 134.27, 127.74, 127.55, 124.86, 118.76, 68.37, 60.23, 55.52 (2C), 50.02 (2C), 32.34, 26.10 (3C), 18.48, −5.17 (2C). HRMS-ESI (m/z): [M+H]$^+$ calculated for [C$_{19}$H$_{33}$O$_2$N$_2$Cl$_2$Si]$^+$: 419.1683; found: 419.1672.

Synthesis of hydroxylamine 3ae

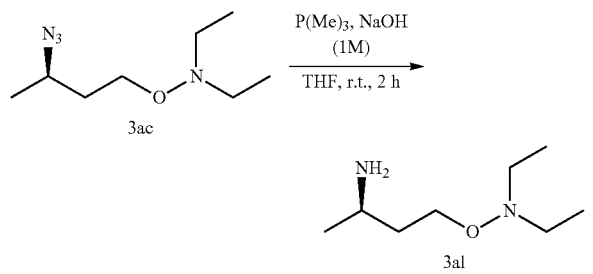

To a stirred solution of 3ac (530 mg, 2.85 mmol, 1.0 eq.) in THF (10.6 mL) was added NaOH (1M) (8.85 mL, 8.85 mmol, 3.1 eq.) at 0° C. The solution was stirred for 2 min, after which, P(Me)$_3$ (1M) (5.7 mL, 5.7 mmol, 2.0 eq.) was added dropwise and the solution was allowed to reach r.t. and stirred for 2 h. After such time, the solution was diluted with H$_2$O (20 m) and the aqueous layer was extracted with DCM (3×20 mL). The combined organic layers were dried over Na$_2$SO$_4$, filtered and concentrated in vacuo. The crude reaction mixture was subjected to flash silica column chromatography (1:9 MeOH:DCM-1:0 MeOH:DCM) to afford the title compound 3al (319 mg, 1.99 mmol, 70%) as a yellow oil. R$_f$=0.10 (1:9 MeOH:DCM;CAM). $^1$H NMR (500 MHz, CD$_3$OD): δ 3.86-3.75 (m, 2H), 3.25 (h, J=6.6 Hz, 1H), 2.73 (q, J=7.1 Hz, 4H), 1.90-1.78 (m, 1H), 1.74-1.63 (m, 1H), 1.23 (d, J=6.6 Hz, 3H), 1.12 (t, J=7.1 Hz, 6H). $^{13}$C NMR (126 MHz, CD$_3$OD): δ 71.4, 53.3 (2C), 46.7, 36.5, 20.4, 12.4 (2C). HRMS-ESI (m/z): [M+H]$^+$ calculated for [C$_8$H$_{21}$ON$_2$]$^+$: 161.1648, found: 161.1645. [α]$_D$=−32.0 (c=1.0 g/100 mL, CHCl$_3$).

Synthesis of hydroxylamine (3af)

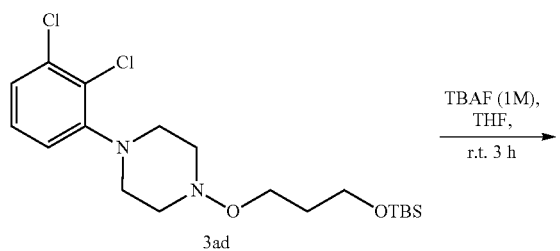

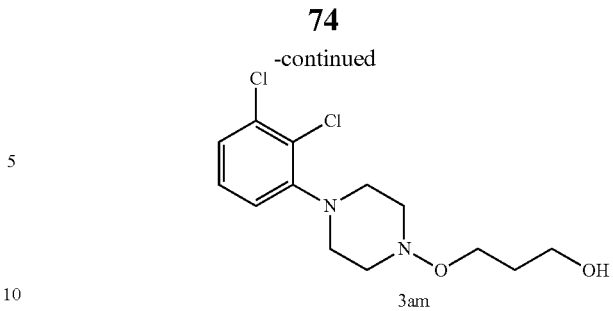

To a stirred solution of 3ad (700 mg, 1.67 mmol, 1.0 eq.) in 30 mL anhydrous THF was added TBAF (1 M) (5 mL, 5 mmol, 3.0 eq.) at 0° C. The solution was stirred for 30 min at 0° C., after which, it was warmed to r.t. and stirred for an additional 2.5 h. After such time, the mixture was quenched via addition of H$_2$O (30 mL) and the aqueous layer extracted with EtOAc (3×20 mL). The organic layers were combined and washed with brine (1×20 mL) and dried over Na$_2$SO$_4$, filtered, and concentrated in vacuo. The residue obtained was subjected to flash silica column chromatography (98:2 EtOAc:Et$_3$N) to afford the title compound 3 am (416 mg, 1.37 mmol, 82%) as a yellow oil. R$_f$=0.50 (98:2 EtOAc:Et$_3$N;CAM). $^1$H NMR (500 MHz, CDCl$_3$): δ 7.18-7.09 (m, 2H), 6.93 (dd, J=7.8, 1.8 Hz, 1H), 3.93-3.87 (t, J=5 Hz, 2H), 3.73 (q, J=5.7 Hz, 2H), 3.33 (d, J=8.7 Hz, 4H), 2.94 (t, J=5 Hz, 1H), 2.90 (m, 4H), 1.87 (h, J=5.8 Hz, 2H). $^{13}$C NMR (126 MHz, CDCl$_3$): δ 150.6, 134.3, 127.8, 15.0, 118.8, 70.0, 61.4, 55.4 (2C), 49.9 (2C), 32.6. HRMS-ESI (m/z): [M+H]$^+$ calculated for [C$_{13}$H$_{19}$O$_2$N$_2$Cl$_2$]: 305.0818, found: 305.0808.

Example 11: Synthesis of Hydroxylamines from Monoperoxyacetals

Synthesis of MTHP Monoperoxyacetal (21)

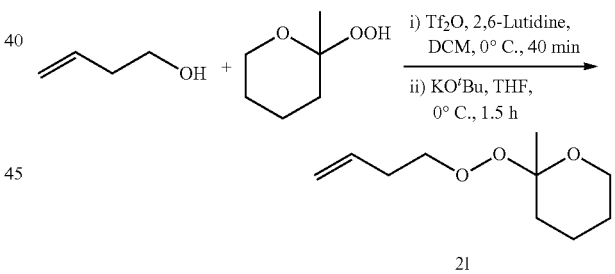

The reaction was performed following general procedure A with 3-butene-1-ol (500 μL, 5.81 mmol, 1.0 eq.), 2,6-lutidine (1 mL, 8.72 mmol, 1.5 eq.), and Tf$_2$O (1.17 mL, 6.97 mmol, 1.2 eq.) in 20 mL anhydrous DCM (0.29 M). The solution was stirred for 40 min under an argon atmosphere, after which, the crude reaction mixture was subjected to column chromatography on silica (eluent: 10:90 EtOAc:Hexanes) to afford the triflate (1.09 g, 5.34 mmol, 92%).

Following general procedure A, to a solution of 2-hydroperoxy-2-methyltetrahydro-2H-pyran (396 mg, 3.0 mmol, 1.5 eq.) under an argon atmosphere dissolved in 10 mL anhydrous THF (0.3 M) was added KO$^t$Bu (291 mg, 2.6 mmol, 1.3 eq.) in a single portion at 0° C. The reaction was stirred for 10 min at 0° C., after which, a portion of the triflate (408 mg, 2.0 mmol, 1.0 eq.) obtained in the previous step dissolved in 0.5 mL of anhydrous THF was added dropwise over 5 min. The reaction was stirred at 0° C. for 1.5 h under an argon atmosphere. The crude reaction mixture was subjected to flash column chromatography on silica (eluent: 10:90 EtOAc:Hexanes) to afford MTHP monoperoxyacetal 21 (356 mg, 1.91 mmol, 95%) as a clear oil. $R_f$=0.50 (10:90 EtOAc:Hexanes; CAM). $^1$H NMR (500 MHz, CDCl$_3$): δ 5.81 (m, 1H), 5.09 (dd, J=15.0, 1.6 Hz, 1H), 5.04 (d, J=10.1, 1H), 4.07 (m, 2H), 3.91 (td, J=11.5, 2.8, 1H), 3.69 (m, 1H), 2.40 (qd, J=6.8, 1.5 Hz, 2H), 1.76-1.40 (m, 6H), 1.42 (d, J=1.1 Hz, 3H). $^{13}$C NMR (126 MHz, CDCl$_3$): δ 134.7, 116.8, 102.4, 74.5, 61.8, 33.4, 32.6, 24.9, 24.6, 19.2. HRMS-ESI (m/z): [M+Na$^+$] calculated for [C$_{10}$H$_{18}$O$_3$Na]$^+$: 209.1148, found, 209.1138.

Synthesis of MTHP Monoperoxyacetal (2m)

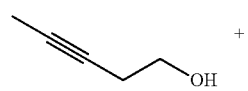

+

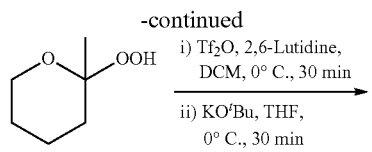

i) Tf$_2$O, 2,6-Lutidine, DCM, 0° C., 30 min
ii) KO$^t$Bu, THF, 0° C., 30 min

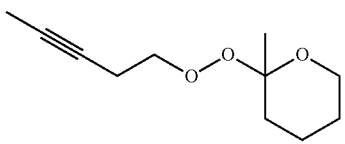

2m

The reaction was performed following general procedure A with 3-pentyn-1-ol (500 μL, 5.42 mmol, 1.0 eq.), 2,6-lutidine (942 μL, 8.13 mmol, 1.2 eq.), and Tf$_2$O (1.09 mL, 6.50 mmol, 1.2 eq.) in 20 mL anhydrous DCM (0.27 M). The solution was stirred for 30 min under an argon atmosphere, after which, the crude mixture was subjected to column chromatography on silica (eluent: 10:90 EtOAc:Hexanes) to afford the triflate (1.12 g, 5.18 mmol, 96%).

Following general procedure A, to a stirred solution of 2-hydroperoxy-2-methyltetrahydro-2H-pyran (396 mg, 3.0 mmol, 1.5 eq.) dissolved in anhydrous THF (10 mL), was added KOtBu (291 mg, 2.6 mmol, 1.2 eq.) in a single portion under an argon atmosphere at 0° C. After 10 minutes of stirring, a portion of the triflate (432 mg, 2.0 mmol, 1.0 eq.) dissolved in anhydrous THF (1.0 mL) was added dropwise. The solution was stirred for 30 min at 0° C. under an argon atmosphere. The crude mixture was then subjected to flash column chromatography on silica (eluent: 10:90 EtOAc:Hexanes) to afford the MTHP monoperoxyacetal 2m (345 mg, 1.74 mmol, 87%) as a pale yellow oil.

Synthesis of Hydroxylamine 3ae, with MTHP Monoperoxyacetal (2b)

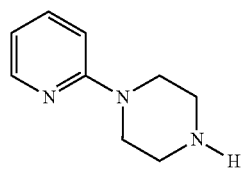 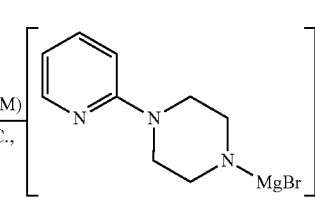 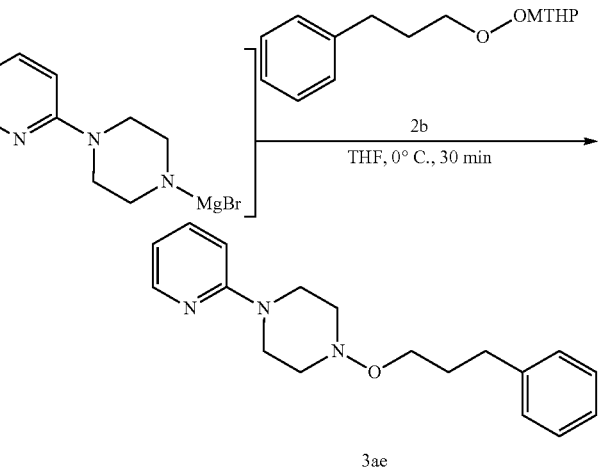

Following general procedure C, 1-(2-pyridyl)piperazine (76 μL, 0.5 mol, 2.5 eq.) was treated in 0.5 mL of anhydrous THF with EtMgBr (3 M) (133 μL, 0.4 mmol, 2.0 eq.) and the solution was stirred for 15 min at 0° C., after which the magnesium amide was transferred to a stirred solution of MTHP monoperoxyacetal (2b) (50.1 mg, 0.2 mmol, 1.0 eq.) in 0.5 mL of anhydrous THF (0.2 M) and stirred for 30 min at 0° C. The crude mixture was subjected to flash column chromatography on silica (eluent: 1:4 EtOAc:Hexanes) to afford the title compound 3ae (49 mg, 0.17 mmol, 83%) as a light yellow oil. $R_f$=0.10 (1:9 EtOAc:Hexanes; UV, CAM). $^1$H NMR (600 MHz, CDCl$_3$): δ 8.16 (dd, J=4.9, 2.0 Hz, 1H), 7.45 (ddd, J=8.9, 7.1, 2.0 Hz, 1H), 7.29-7.23 (m, 2H), 7.20-7.13 (m, 3H), 6.64-6.58 (m, 2H), 4.12 (br d, J=12.8 Hz, 2H), 3.74 (t, J=6.5 Hz, 2H), 3.29 (br d, J=10.4 Hz, 2H), 3.06 (br t, J=12.1 Hz, 2H), 2.71-2.65 (m, 4H), 1.94-1.85 (m, 2H). $^{13}$C NMR (151 MHz, CDCl$_3$): δ 159.2, 148.0, 142.1, 137.6, 128.6 (2C), 128.4 (2C), 125.9, 113.5, 107.1, 70.9, 55.3 (2C), 44.3 (2C), 32.5, 30.6. HRMS-ESI (m/z): [M+H]$^+$ calculated for [C$_{18}$H$_{23}$N$_3$O]$^+$: 298.1914, found: 298.1905.

Synthesis of Hydroxylamine 3af, with MTHP Monoperoxyacetal (2b)

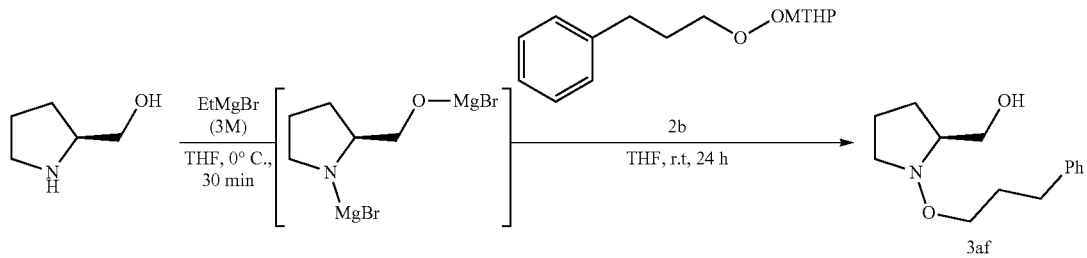

To an oven dried 10 mL flask was added (S)-(+)-2-pyrrolidinemethanol (39 µL, 0.4 mmol, 2.0 eq.) and 0.5 mL anhydrous THF at 0° C. To this solution was then added EtMgBr (3 M) (270 µL, 0.8 mmol, 4.0 eq.) in two portions with a 5 min interval, followed by stirring for 30 min 0° C. The magnesium amide solution was then transferred via syringe to a stirred solution of the MTHP monoperoxyacetal (2b) (51 mg, 0.2 mmol, 1.0 eq.) in 0.5 mL anhydrous THF (0.2 M total) at 0° C. The solution was stirred for 24 h at room temperature until starting material had been consumed as indicated by TLC and MS, after which the mixture was quenched by addition of chilled water (5 mL) and the layers separated. The aqueous layer was re-extracted with EtOAc (4×, 5 mL). The organic layers were combined, dried over $Na_2SO_4$, filtered, and concentrated in vacuo. Flash silica column chromatography (eluent: 1:9 EtOAc:DCM) afforded the title compound 3af (30 mg, 0.12 mmol, 63%) as a light yellow oil. $R_f$=0.43 (1:4 EtOAc:DCM; UV, CAM). $^1$H NMR (600 MHz, $CDCl_3$, Major Rotamer): δ 7.34-7.26 (m, 2H), 7.23-7.18 (m, 3H), 3.82-3.72 (m, 3H), 3.52-3.45 (m, 1H), 3.29 (ddd, J=10.8, 7.4, 4.4, 1H), 3.21-3.16 (m, 1H), 2.96-2.89 (m, 1H), 2.72-2.67 (m, 2H), 2.48-2.37 (br s, 1H), 1.97-1.85 (m, 4H), 1.78-1.67 (m, 1H), 1.62-1.53 (m, 1H). $^{13}$C NMR (151 MHz, $CDCl_3$): δ 142.0, 128.6 (2C), 128.5 (2C), 126.1, 72.6, 68.4, 63.0, 55.7, 32.5, 30.7, 23.9, 21.2. HRMS-ESI (m/z): [M+H]$^+$ calculated for $[C_{14}H_{21}N_2O]^+$: 236.1645, found: 236.1639.

Synthesis of Hydroxylamine 3aq, with MTHP Monoperoxyacetal (21)

Following general procedure C, N-methylaniline (108 µL, 1.0 mmol, 2.5 eq.) was treated in 1 mL of anhydrous THF with EtMgBr (3 M) (267 µL, 0.8 mmol, 2.0 eq.) and the solution was stirred for 10 min at 0° C., after which the magnesium amide was transferred to a stirred solution of MTHP monoperoxyacetal (21) (75 mg, 0.4 mmol, 1.0 eq.) in 1 mL of anhydrous THF (0.2 M) and stirred for 30 min at 0° C. The crude mixture was subjected to flash column chromatography on silica (eluent: 2:98 EtOAc:Hexanes) to afford the title compound 3ag (53 mg, 0.3 mmol, 75%) as a clear oil. $R_f$=0.80 (10:90 EtOAc:Hexanes; UV, CAM). $^1$H NMR (500 MHz, $CDCl_3$): δ 7.31-7.26 (m, 2H), 7.06-7.02 (m, 2H), 6.99-6.93 (m, 1H), 5.87 (ddt, J=17.1, 10.2, 6.7 Hz, 1H), 5.13 (dq, J=17.2, 1.6 Hz, 1H), 5.08 (dq, J=10.2, 1.4 Hz, 1H), 3.89 (t, J=6.8 Hz, 2H), 3.07 (s, 3H), 2.44 (qt, J=6.8, 1.4 Hz, 2H). $^{13}$C NMR (126 MHz, $CDCl_3$): δ 152.9, 135.2, 128.9 (2C), 122.0, 116.8, 115.9 (2C), 72.2, 44.7, 33.2. HRMS-ESI (m/z): [M+H]$^+$ calculated for $[C_{11}H_{16}ON]^+$: 178.1226, found: 178.1219.

Synthesis of Hydroxylamine 3ah, with MTHP Monoperoxyacetal (21)

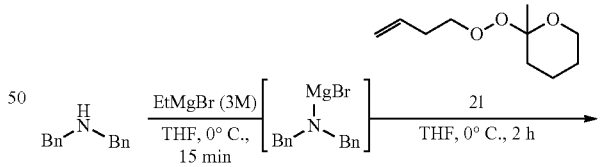

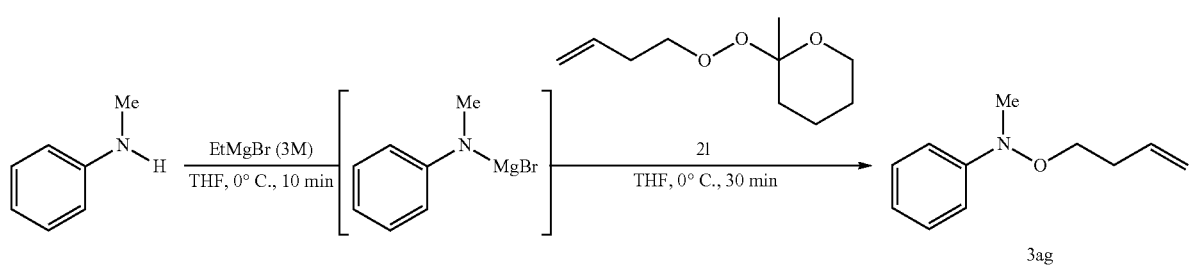

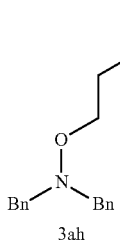
3ah

Following general procedure C, dibenzylamine (192 μL, 1.0 mmol, 2.5 eq.) was treated in 1 mL of anhydrous THF with EtMgBr (3 M) (267 μL, 0.8 mmol, 2.0 eq.) and the solution was stirred for 15 min at 0° C., after which, the magnesium amide was transferred to a stirred solution of MTHP monoperoxyacetal (21) (75, 0.4 mmol, 1.0 eq.) in 1 mL of anhydrous THF (0.2 M) and stirred for 2 h at 0° C. The crude mixture was subjected to flash column chromatography on silica (eluent: 5:95 diethyl ether:Hexanes) to afford the title compound 3ah (73 mg, 0.27 mmol, 68%) as a white oil. $R_f$=0.70 (5:95 diethyl ether:Hexanes; UV, CAM). $^1$H NMR (500 MHz, CDCl$_3$): δ 7.43-7.39 (m, 4H), 7.36-7.31 (m, 4H), 7.31-7.25 (m, 2H), 5.61-5.50 (m, 1H), 4.92 (dq, J=2.9, 1.7 Hz, 1H), 4.89 (m, 1H), 3.88 (s, 4H), 3.38 (t, J=6.7 Hz, 2H), 2.03 (qt, J=6.3, 1.3 Hz, 2H). $^{13}$C NMR (126 MHz, CDCl$_3$): δ 137.9 (2C), 135.6, 129.8 (4C), 128.2 (4C), 127.3 (2C), 115.9, 72.6, 62.7 (2C), 33.1. HRMS-ESI (m/z): [M+H]$^+$ calculated for [C$_{18}$H$_{22}$ON]$^+$: 268.1696, found: 268.1695.

Synthesis of Hydroxylamine 3ai, with MTHP Monoperoxyacetal (2m)

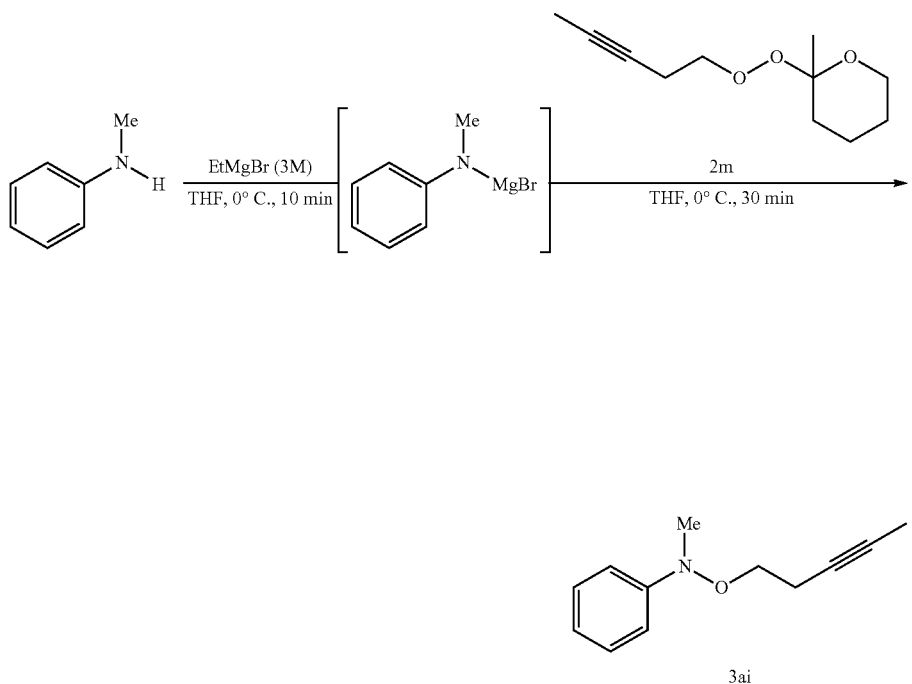

3ai

Following general procedure C, N-methylaniline (108 μL, 1.0 mmol, 2.5 eq.) was treated in 1.0 mL of anhydrous THF with EtMgBr (3 M) (267 μL, 0.8 mmol, 2.0 eq.) and the solution was stirred for 10 min at 0° C. After which, the magnesium amide was transferred to a stirred solution of MTHP monoperoxyacetal (2m) (79 mg, 0.4 mmol, 1.0 eq.) in 1.0 mL of anhydrous THF (0.2 M) and stirred for 30 min at 0° C. The crude mixture was subjected to flash column chromatography on silica (eluent: 10:90 EtOAc:Hexanes) to afford the title compound 3ai (63 mg, 0.333 mmol, 83%) as a yellow oil. $R_f$=0.80 (10:90 EtOAc:Hexanes; UV, CAM). $^1$H NMR (500 MHz, CDCl$_3$): δ 7.28 (t, J=10.0 Hz, 2H), 7.08 (d, J=8.5 Hz, 2H), 6.97 (t, J=7.3 Hz, 1H), 3.91 (t, J=6.8 Hz, 2H), 3.08 (s, 3H), 2.51 (m, 2H), 1.80 (t, J=2.6 Hz, 3H). $^{13}$C NMR (126 MHz, CDCl$_3$): δ 152.9, 128.9 (2C), 122.1, 116.0 (2C), 76.9, 76.0, 71.4, 44.9, 19.1, 3.6. HRMS-ESI (m/z): [M+H]$^+$ calculated for [C$_{12}$H$_{16}$ON]$^+$: 190.1226, found: 190.1217.

Synthesis of Hydroxylamine 3aj, with MTHP Monoperoxyacetal (2m)

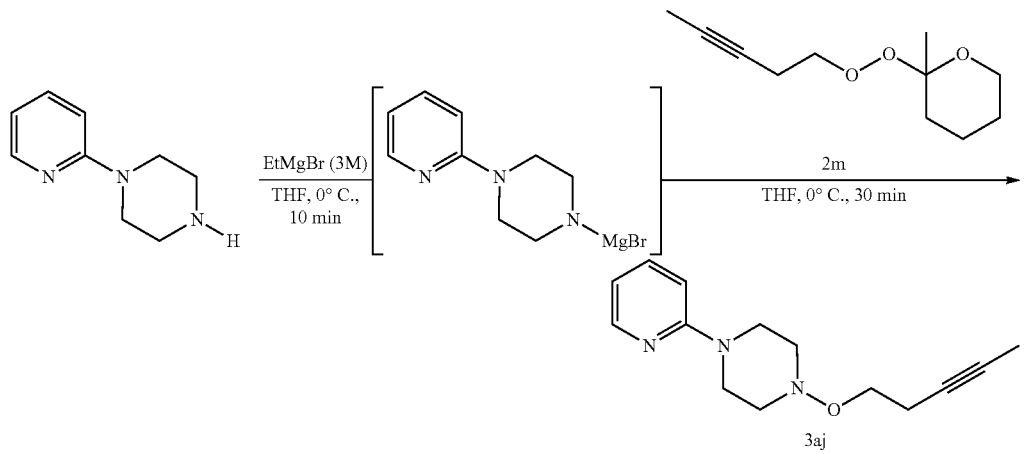

Following general procedure C, 1-(2-pyridyl)piperazine (76 μL, 0.5 mmol, 2.5 eq.) was treated in 0.5 mL of anhydrous THF with EtMgBr (3 M) (133 μL, 0.4 mmol, 2.0 eq.) and the solution was stirred for 10 min at 0° C. After which, the magnesium amide was transferred to a stirred solution of MTHP monoperoxyacetal (2m) (39.6 mg, 0.2 mmol, 1.0 eq.) in 0.5 mL of anhydrous THF (0.2 M) and stirred for 30 min at 0° C. The crude mixture was subjected to flash column chromatography on silica (eluent: 30:70 EtOAc:Hexanes) to afford the title compound 3aj (36.3 mg, 0.148 mmol, 74%) as a yellow oil. $R_f$=0.80 (1:1 EtOAc:Hexanes; UV, CAM). $^1$H NMR (500 MHz, CDCl$_3$): δ 8.16 (dd, J=5.0, 2.1 Hz, 1H), 7.46 (ddd, J=8.9, 7.0, 2.0 Hz, 1H), 6.64-6.58 (m, 2H), 4.13 (d, J=12.7 Hz, 2H), 3.78 (t, J=6.9 Hz, 2H), 3.29 (d, J=10.2 Hz, 2H), 3.05 (t, J=11.8 Hz, 2H), 2.77-2.65 (m, 2H), 2.45 (tq, J=6.9, 2.5 Hz, 2H), 1.77 (t, J=2.6 Hz, 3H). $^{13}$C NMR (126 MHz, CDCl$_3$): δ 159.2, 148.1, 137.6, 113.6, 107.1, 76.7, 76.1, 70.4, 55.4 (2C), 44.3 (2C), 19.5, 3.6. HRMS-ESI (m/z): [M+H]$^+$ calculated for [C$_{14}$H$_{20}$N$_3$O]$^+$: 246.1601, found: 246.1598.

Synthesis of Hydroxylamine 3ak, with MTHP Monoperoxyacetal (2h)

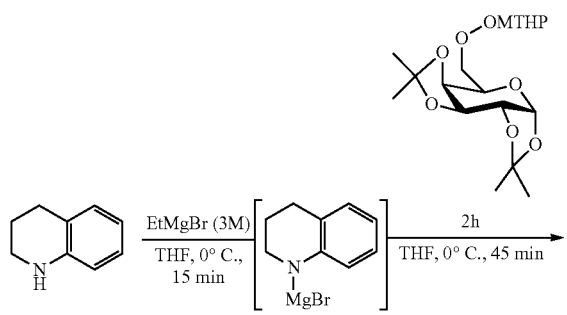

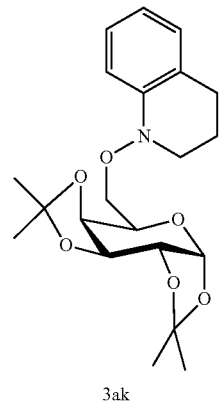

Following general procedure C, 1,2,3,4-tetrahydroquinoline (126 μL, 1.0 mmol, 2.5 eq.) was treated in 1.0 mL of anhydrous THF with EtMgBr (3 M) (267 μL, 0.8 mmol, 2.0 eq.) and the solution was stirred for 15 min at 0° C. After which, the magnesium amide was transferred to a stirred solution of MTHP monoperoxyacetal (2h) (150 mg, 0.4 mmol, 1.0 eq.) in 1.0 mL of anhydrous THF and stirred for 45 min at 0° C. Due to similar $R_f$ values between the amine and product 3ak, the excess amine was removed from the organic layer via acid wash (1 N HCl, 10 mL) followed by NaHCO$_3$ (10 mL). The crude reaction mixture was subjected to flash column chromatography on silica (eluent: 2:98-15:85 diethyl ether:Hexanes) to afford the title compound 3ak (77 mg, 0.196 mmol, 49%) as an orange oil. $R_f$=0.40 (20:80 diethyl ether:Hexanes; CAM). $^1$H NMR (500 MHz, CDCl$_3$): δ 7.29-7.22 (m, 1H), 7.15-7.06 (m, 1H), 6.96 (dd, J=7.5, 1.5 Hz, 1H). 6.82 (td, J=7.4, 1.3 Hz, 1H), 5.62 (d, J=5.2 Hz, 1H), 4.61 (dd, J=7.8, 2.5 Hz, 1H), 4.34 (dd, J=5.1, 2.4 Hz, 1H), 4.25 (dd, J=7.9, 2.0 Hz, 1H), 4.19 (ddd, J=6.4, 4.1, 2.0 Hz, 1H), 4.14-4.07 (m, 2H), 3.43 (ddd, J=11.1, 7.3, 4.0 Hz, 1H), 3.35 (ddd, J=10.0, 7.4, 4.0 Hz, 1H), 2.73 (t, J=6.7 Hz, 2H), 2.05 (dq, J=10.8, 6.8, 3.4, 2H), 1.46 (d, J=3.6 Hz, 6H), 1.34 (d, J=6.5 Hz, 6H). $^{13}$C NMR (126 MHz, CDCl$_3$): δ 148.5, 128.8, 126.8, 124.9, 121.5, 116.4, 109.5, 108.7, 96.7, 72.9, 71.8, 70.9, 70.5, 65.8, 51.4, 26.4, 26.1, 26.0, 25.1, 24.7, 22.2.

HRMS-ESI (m/z): [M+H]+ calculated for [$C_{21}H_{30}O_6N$]+: 392.2068, found: 392.2053. [α]$_D$=−7.6 (c=1.0 g/100 mL, CHCl$_3$).

Synthesis of Hydroxylamine (3an)

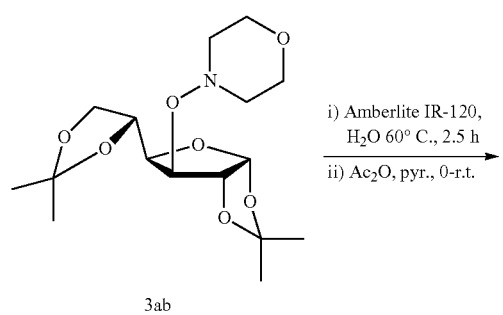

3ab i) Amberlite IR-120, H$_2$O 60° C., 2.5 h
ii) Ac$_2$O, pyr., 0-r.t.

3an

To a stirred solution of 1,2:5,6-di-O-isopropylidene-3-O-(morpholin-1-yl)-α-D-glucofuranose (3ab) (28 mg, 0.082 mmol, 1.0 eq.) in H$_2$O (1.65 mL) was added Amberlite® IR-120, hydrogen form (112 mg) in one portion and the reaction mixture was brought to 60° C. and stirred for 2.5 h. After such time, the reaction mixture was cooled to room temperature and diluted with acetone (5 mL). Solid resin was filtered and washed with acetone (2×5 mL). The filtrate was concentrated in vacuo to afford a white residue that was used directly in the next step without further purification. The residue obtained from the previous step was dissolved in pyridine (0.5 mL) and cooled to 0° C. Acetic anhydride (0.5 mL, 0.656 mmol, 8.0 eq.) was then added dropwise over 2 min and the reaction was stirred at room temperature for 12 h. After such time, the solvent was removed in vacuo and the residue obtained was subjected to flash column chromatography on silica (eluent: 4:1 DCM:EtOAc) to afford the title compound 3an (24.4 mg, 0.056 mmol, 69% over 2 steps) as a colorless oil. R$_f$=0.50 (1:4 EtOAc:DCM; H$_2$SO$_4$). $^1$H NMR (600 MHz, CDCl$_3$) (Product was obtained as an α:β 1:1.6 mixture): δ 6.31 (d, J=3.8 Hz, 1H), 5.66 (d, J=8.2 Hz, 1H), 5.14-5.02 (m, 4H), 4.25-4.16 (m, 3H), 4.10 (d, J=2.3 Hz, 2H), 4.06-4.00 (m, 2H), 3.86 (d, J=11.6 Hz, 4H), 3.75 (ddd, J=10.0, 5.0, 2.4 Hz, 1H0, 3.52 (q, J=13.1, 11.3 Hz, 4H), 3.11-2.96 (m, 4H), 2.66-2.55 (m, 4H), 2.17 (s, 3H), 2.11 (d, J=0.7 Hz, 6H), 2.09 (d, J=1.6 Hz), 2.08 (d, J=0.8 Hz, 6H), 2.06 (s, 3H). $^{13}$C NMR (151 MHz, CDCl$_3$): δ 170.7, 169.5, 169.3, 92.1, 89.5, 80.7, 78.5, 73.0, 70.7, 70.2, 69.6, 68.3, 68.2, 66.1, 61.9, 56.7, 21.0, 20.93, 20.90, 20.8, 20.7. HRMS-ESI (m/z): [M+Na]+ calculated for [$C_{18}H_{27}NO_{11}Na$]+: 456.1476, found: 456.1477.

Example 12: Synthesis of O-tert-Butyl-N,N-Disubstituted Hydroxylamines, Related Compounds, and Precursors The reaction of commercially available tert-butyl peroxybenzoate (TBPB) with the magnesium salt of dibenzylamine was evaluated using conditions resembling a previously reported hydroxylamine forming reaction (Scheme 1). The O-tert-butyl-N,N-disubstituted hydroxylamine (4a) was formed in a 67% isolated yield with the corresponding benzamide (5a) formed in only 6% yield. Swapping the magnesium salt for the lithium salt of dibenzylamine yielded only trace amounts of the intended product (4a) at −78° C. with the major product isolated being the corresponding benzamide (5a) (62%). Treating the lithium salt of dibenzylamine with TBPB at 0° C. resulted in markedly decreased yields of both products. A slight decrease in yield was observed by switching the solvent from THF to ether or toluene, with the intended product (4a) formed in a 63 and 59% yield, respectively, and the corresponding benzamide (5a) formed in comparable yields as with THF (8 and 7%). Under neutral conditions or Lewis acidic conditions, no reaction was observed with only starting material detected by NMR spectroscopy of the crude reaction mixture.

TABLE 2

Optimization of Reaction Conditions$^a$

| Entry | Variation of Standard Condition | 4a yield (%) | 5a yield (%) |
|---|---|---|---|
| 1 | None | 69 (67) | 6 |
| 2 | n-BuLi instead of EtMgBr (−78° C.) | Trace | 68 (62) |
| 3 | n-BuLi instead of EtMgBr (0° C.) | 10 | 5 |
| 4 | Et$_2$O instead of THF | 63 | 8 |
| 5 | Toluene instead of THF | 59 | 7 |
| 6 | No EtMgBr | n.r.$^b$ | n.r.$^b$ |
| 7 | MgBr$_2$ instead of EtMgBr | n.r.$^b$ | n.r.$^b$ |

$^a$All reactions run on the 0.3 mmol scale. NMR yield determined by using 1,3,5-trimethoxybenzene as internal standard (isolated yield in parentheses).
$^b$Reaction run for 24 h and monitored by TLC and MS. Crude NMR taken after 24 h to confirm no reaction.

Working with the magnesium amides, the scope of the amine nucleophiles was investigated. Surprisingly however, upon treatment of the magnesium salt of N-methylbenzylamine with TBPB only 21% of the desired product (4b) was observed, with the major product observed as the benzamide (5b) (63%). Considering the major steric dependency observed by Benn in the reaction of lithium amides with TBPB, ortho,ortho-disubstituted esters were used to retard 1,2-addition. Accordingly, 2,6-dimethyl-tert-butyl peroxybenzoate was prepared by standard acylation chemistry for further investigation. Upon reaction of the magnesium salt of N-methylbenzylamine with 2,6-dimethyl-tert-butyl peroxybenzoate an improved isolated yield of 55% was obtained for the desired product (4b) with only trace amounts of the benzamide (5b) observed, thereby highlighting the dependence on the chemoselective reaction of peresters with metal amides of steric interactions. Additionally, the reaction of magnesium dibenzylamide with 2,6-dimethyl-tert-butylperoxybenzoate afforded the intended product (4a) in a 62% yield, comparable to that obtained upon reaction with TBPB. Effectively, the less hindered amide nucleophile is best paired with the ortho, ortho-disubstituted electrophile, while the more hindered nucleophile functions well with either electrophile.

TABLE 3

Investigation of Steric Effects on Regioselectivity[a]

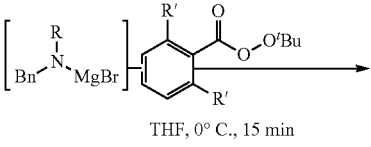

| Entry | R | R' | 4a-4b yield (%) | 5a-5b yield (%) |
|---|---|---|---|---|
| 1 | Me | H | 21 | 66 (63) |
| 2 | Me | Me | 60 (55) | Trace |
| 3 | Bn | H | 69 (67) | 6 |
| 4 | Bn | Me | 62 | trace |

[a]All reactions were run on the 0.3 mmol scale. NMR yield determined by using 1,3,5-trimethoxybenzene as internal standard (isolated yield in parentheses).

With the reaction now optimized to favor 1,4-addition, the tolerance of a variety of amine nucleophiles bearing a wide range of functional groups was investigated (Scheme 4).

Scheme 4. Synthesis of O-tert-butyl-N,N-disubstituted hydroxylamines.

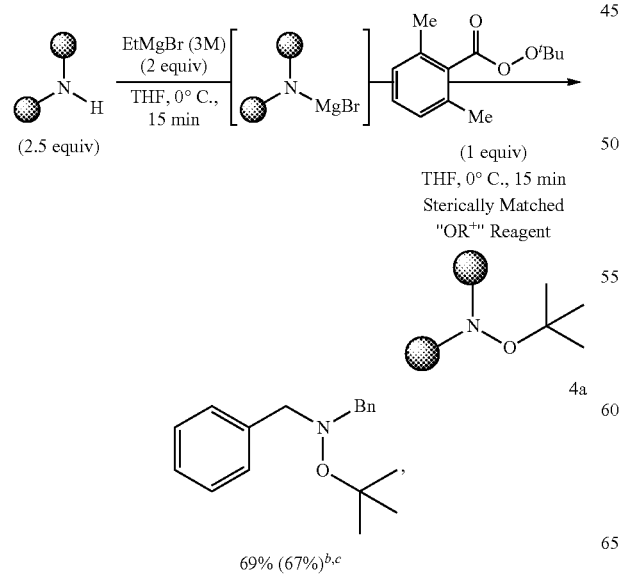

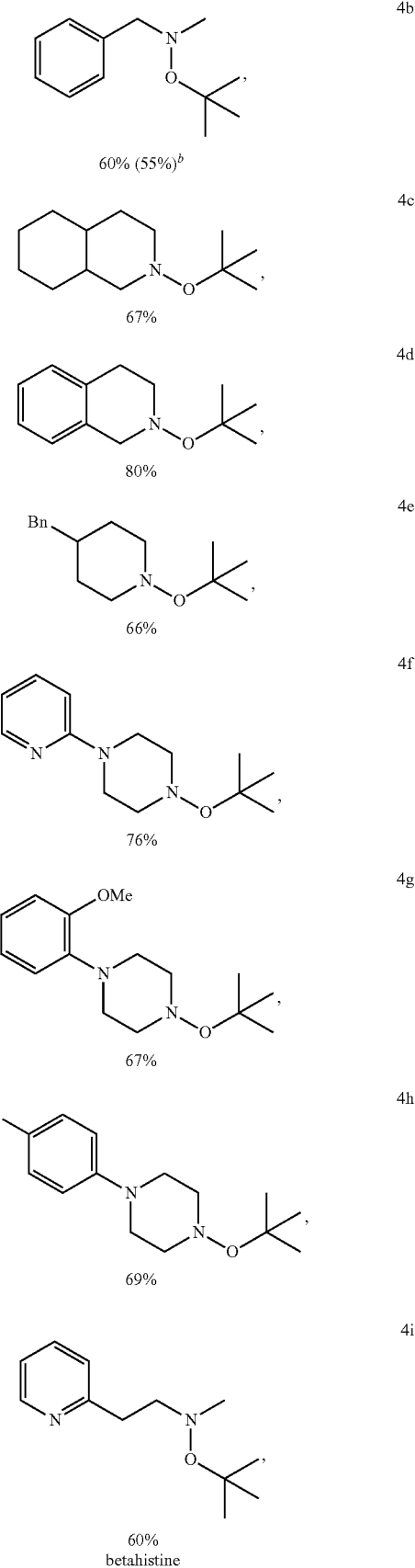

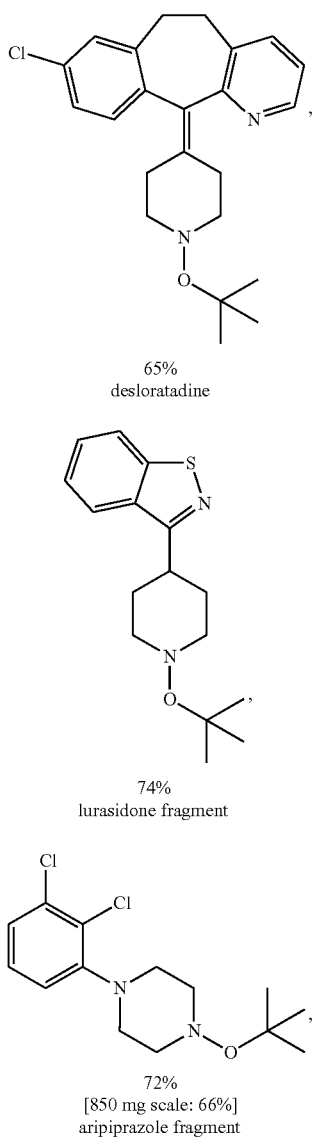

65%
desloratadine

74%
lurasidone fragment

72%
[850 mg scale: 66%]
aripiprazole fragment

[a]Reactions performed on a 0.4 mmol scale. All reported yields are after isolation unless otherwise stated. [b]Reaction run on the 0.3 mmol scale. NMR yield determined by using 1,3,5-trimethoxybenzene as internal standard (isolated yield in parenthesis ). [c]tert-butylperoxybenzoate (TBPB) used as electrophile.

With emphasis on heterocycles commonly encountered in drug motifs perhydro- and tetrahydro-isoquinoline derived magnesium salts were used as starting points, which afforded products (4c-4d) in good yields (67-80%) upon reaction with the sterically matched electrophile. A substituted piperidine derivative was also well tolerated in the reaction with 4-benzyl-piperidine affording the corresponding product (4e) in a 66% yield. N-Aryl-piperazines were also well tolerated in the reaction, with 1-(2-pyridyl)-piperazine, 1-(2-methoxyphenyl)-piperazine and 1-(4-trifluoromethylphenyl)-piperazine derived magnesium salts affording products (4f-h) in 76, 67 and 69% yields, respectively, upon reaction with the sterically matched electrophile. As a further demonstration of the methodology, frameworks encountered in pharmaceutical agents were next investigated. All such fragments tested afforded products (4i-l) in fair to good yields (60-74%) with even alkenes and thiazoles being well tolerated when paired with the sterically matched electrophile. As a further demonstration of the methodology, 1-(2,3-dichlorophenyl)piperazine, a fragment of the widely used antipsychotic aripiprazole, was reacted on the 850 mg scale, affording the intended product (4l) in a 66% yield when paired with the sterically matched electrophile.

Mechanistically, the observed reactivity can be rationalized by the occurrence of an irreversible attack on the peroxy oxygen bond in competition with a reversible carbonyl addition as was previously observed by Cline and Hanna for the aminolysis of N-hydroxysuccinimide esters (Scheme 5).

Scheme 5 Proposed reaction pathway.

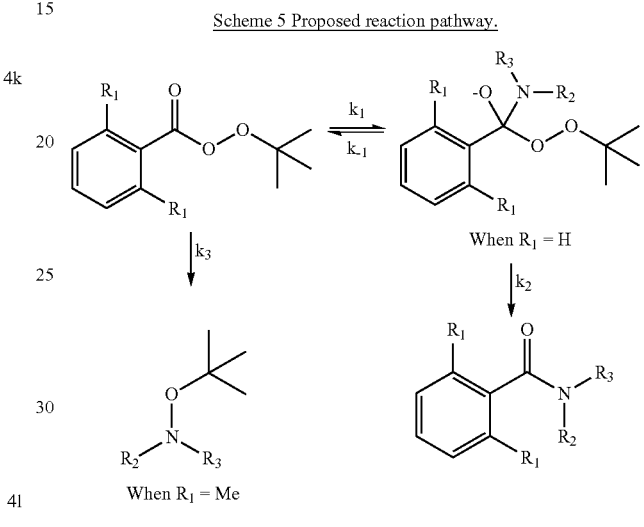

For unsubstituted TBPB, $k_1 > k_3$, which following irreversible collapse ($k_2$) of the tetrahedral intermediate affords the benzoylated product observed in this study and those seen by Benn. Switching to the sterically matched 2,6-dimethyl-tert-butylperoxybenzoate results in 1,2-addition to the carbonyl being sufficiently slow, as was seen in the hydrolysis study of ortho-substituted benzoylcholine esters, so that $k_3 > k_1$. Thus, irreversible 1,4-peroxy oxygen addition ($k_3$) by N—O bond formation predominates and the intended O-tert-butyl-N,N-disubstituted hydroxylamines are formed in high yields. This same effect was observed earlier by Benn and Meesters, wherein, 0-tert-butyl-N-monosubstituted hydroxylamines could only be obtained using sterically encumbered nucleophiles which sufficiently retard 1,2-addition to the carbonyl ($k_1$) to a point where 1,4-peroxy oxygen addition ($k_3$) by N—O bond formation is observed (FIG. 8D). The insensitivity of the more-bulky nucleophiles to ortho-substitution is best accounted for by reversible 1,2-addition with collapse of the tetrahedral intermediate to the amide ($k_2$) being retarded both by the steric nature of the product and also the increasing crowding of the $sp^3$ transition state.

General Experimental

All reactions were conducted in oven dried glassware capped with a rubber septum under an argon atmosphere unless otherwise stated. All organic solutions were concentrated under reduced pressure on a rotary evaporator and water bath. Flash-column chromatography was performed using silica gel (Fischer Silica Gel Sorbent (230-400 Mesh, Grade 60)). Thin-layer chromatography (TLC) was carried out with 250 μm glass back silica (XHL) plates with fluorescent indicator (254 nm). TLC plates were visualized by exposure to ultraviolet light (UV) and/or submersion in ceric ammonium molybdate solution (CAM) or p-anisaldehyde solution in ethanol followed by heating on a hot plate (120° C., 10-15 s).

Materials

Commercial solvents and reagents were used as received without further purification. EtMgBr (3 M in diethyl ether) was purchased from Sigma-Aldrich. tert-Butylperoxybenzoate (TBPB) was purchased from Sigma-Aldrich as a 98% neat solution. tert-butylhydroperoxide (TBHP) was purchased from Sigma-Aldrich as a 5.0-6.0 M solution in decane. Oxalyl chloride and NaH (60% dispersion in mineral oil) were purchased from Sigma-Aldrich. 2,6-Dimethylbenzoic acid was purchased from OakWood chemicals. N-methylbenzylamine, N,N-dibenzylamine, 1,2,3,4-tetrahydroisoquinoline, perhydroisoquinoline, 4-benzylpiperidine, 1-(2-pyridyl)piperazine, 1-(2-methoxyphenyl)piperazine, 1-(4-trifluoromethylphenyl)piperazine were purchased from Sigma-Aldrich in their free base forms. Desloratadine and betahistine were purchased from AK Scientific in their free base forms. 3-(1-Piperazinyl)-1,2-benzoisothiazole and 1-(2,3-dichlorophenyl)piperazine were purchased from OakWood chemicals in their free base form.

Instrumentation

Nuclear magnetic resonance (NMR) spectra of all compounds were obtained in either CDCl$_3$ ($\delta$ 7.26 and 77.16 ppm, respectively) or DMSO-d$_6$ ($\delta$ 2.50 and 39.52 ppm, respectively) using a 500 MHz, EZC500 JEOL instrument. The chemical shifts ($\delta$) are calculated with respect to residual solvent peak and are given in ppm. Multiplicities are abbreviated as follows: s (singlet), multiplet (m), br (broad), d (doublet), t (triplet), q (quartet). High resolution mass spectra were obtained on a ThermoFisher Orbitrap Q-Exactive using electrospray ionization (ESI). Melting points were determined on a Barstead Electrothermal 9100.

Synthesis of 2,6-Dimethyl-tert-butylperoxybenzoate (51)

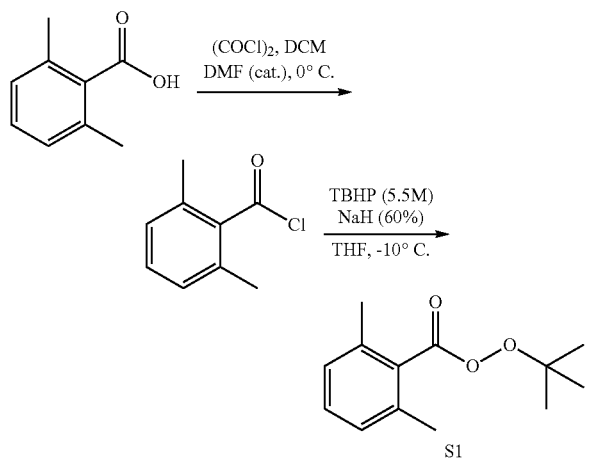

To a stirred solution of 2,6-dimethylbenzoic acid (3 g, 20 mmol, 1.0 eq.) in anhydrous DCM (60 mL) was added DMF (10 drops, cat.) followed by dropwise addition of oxalyl chloride (3.43 mL, 40 mmol, 2.0 eq.) at 0° C. The solution was gradually brought to r.t. and stirred for 2 h. After such time, the volatiles were removed by concentration of the crude reaction mixture and the crude acid chloride was used directly in the following step without purification.

To a stirred solution of TBHP (5.5 M in decane) (7.3 mL, 40 mmol, 2.0 eq.) in anhydrous THF (75 mL) was added NaH (60% dispersion in mineral oil) (1.59 g, 40 mmol, 2.0 eq.) and the solution was stirred for 20 min at −10° C. (salt water/ice). After such time, the crude acid chloride obtained in the previous step was added dropwise in 5.0 mL anhydrous THF and the solution was stirred for 20 min at −10° C. After such time, the reaction mixture was quenched with NaHCO$_3$ (50 mL) and stirred until effervescence ceased. The layers were separated and the organic layer was washed with brine (1×30 mL), dried over Na$_2$SO$_4$, filtered and concentrated in vacuo. The crude mixture was purified by flash column chromatography on silica (10:90 EtOAc:Hexanes) to afford the title compound (51) contaminated with decane. To remove decane, the residue obtained was dissolved in 50 mL CH$_3$CN and washed with Hexanes (2×15 mL) affording pure perester (51) (4.03 g, 18.14 mmol, 91% over 2 steps) as a colorless oil. TLC: R$_f$=0.50 (10:90 EtOAc:Hexanes; UV, p-anisaldehyde). $^1$H NMR (500 MHz, CDCl$_3$): $\delta$ 7.23 (t, J=7.62 Hz, 1H), 7.05 (d, J=7.63 Hz, 2H), 2.37 (s, 6H), 1.40 (s, 9H). $^{13}$C NMR (126 MHz, CDCl$_3$): $\delta$ 167.4, 136.2 (2C), 130.7, 130.3, 127.7 (2C), 83.7, 26.6 (3C), 19.8 (2C). HRMS-ESI (m/z): [M+Na]$^+$ calculated for [C$_{13}$H$_{18}$O$_3$Na]$^+$: 245.1148, found: 245.1143.

*2,6-Dimethyl-tert-butylperoxybenzoate is a stable oil if kept in the refrigerator for long periods of time. No issues have been encountered in decomposition, but standard caution should be exercised when working with peroxides (e.g. avoid exposure to light, reducing agents, heat). For a detailed summary on the safety of peresters please see the recent review by Locklear and Dussault.

General Procedure D for the Synthesis of O-Tert-Butyl-N,N-Disubstituted Hydroxylamines

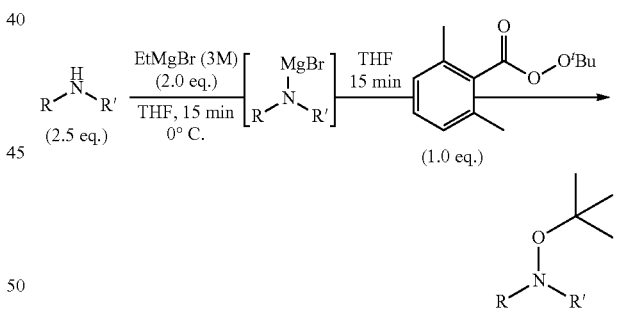

To a stirred solution of amine (0.75-1.0 mmol, 2.5 eq.) in 0.75-1.0 mL anhydrous THF under an argon atmosphere at 0° C. was added EtMgBr (3 M in diethyl ether) (0.6-0.8 mmol, 2.0 eq.) and the solution was stirred for 15 min. After such time, perester (0.3-0.4 mmol, 1.0 eq.) was added dropwise as a solution in 0.75-1.0 mL anhydrous THF (0.2 M total) to the stirred magnesium amide solution. The solution was stirred for an additional 15 min (30 min total reaction time) at 0° C., after which, the solution was diluted with EtOAc (10 mL) and washed with NaHCO$_3$ (1×10 mL) followed by brine (1×10 mL). The organic layer was then dried over Na$_2$SO$_4$, filtered, and concentrated in vacuo. Flash column chromatography on silica (EtOAc:Hexanes) of the crude material afforded the title O-tert-butyl-N,N-disubstituted hydroxylamines.

*Note on magnesium amide formation: while no issues have been encountered generating the corresponding magnesium amides in this work, caution should be exercised on larger scales as ethane gas is rapidly evolved upon deprotonation.

Synthesis of N,N-dibenzylbenzamide (5a)

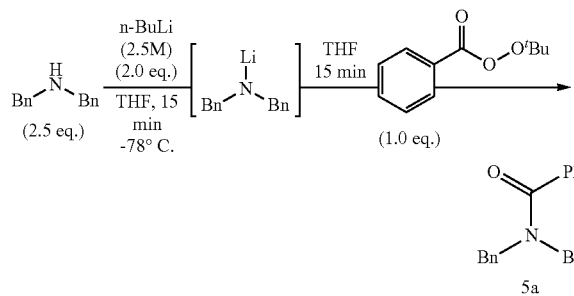

Following the general procedure, N,N-dibenzylamine (144 μL, 0.75 mmol, 2.5 eq.) in 0.75 mL anhydrous THF was added n-BuLi (2.5 M in hexanes) (240 μL, 0.6 mmol, 2.0 eq.) and the solution was stirred for 15 min at −78° C. After which, tert-butyl peroxybenzoate (58 mg, 0.3 mmol, 1.0 eq.) was added dropwise in 0.75 mL anhydrous THF. The solution was stirred for an additional 15 min at −78° C. Following work-up, the crude reaction mixture was checked by NMR spectroscopy with 1,3,5-trimethoxybenzene as internal standard. The crude mixture was then purified by flash column chromatography on silica (eluent: 10:90 EtOAc:Hexanes) to afford the title compound (5a) (56 mg, 0.186 mmol, 62%) as a white solid. TLC: $R_f$=0.50 (25:75 EtOAc:Hexanes; UV, CAM). $^1$H NMR (500 MHz, CDCl$_3$): δ 7.52 (m, 2H), 7.41-7.30 (m, 11H), 7.15 (br s, 2H), 4.72 (br s, 2H), 4.42 (br s, 2H). Spectral data are in accord with that previously reported in the literature. HRMS-ESI (m/z): [M+H]$^+$ calculated for [C$_{21}$H$_{20}$ON]$^+$: 302.1539, found: 302.1528.

Synthesis of N-benzyl-N-methylbenzamide (5b)

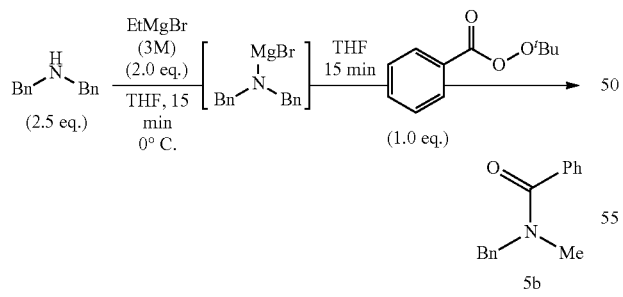

Following general procedure D, N-methylbenzylamine (97 μL, 0.75 mmol, 2.5 eq.) in 0.75 mL anhydrous THF was added EtMgBr (3 M in diethyl ether) (200 μL, 0.6 mmol, 2.0 eq.) and the solution was stirred for 15 min. After which, tert-butyl peroxybenzoate (58 mg, 0.3 mmol, 1.0 eq.) was added dropwise in 0.75 mL anhydrous THF. The solution was stirred for an additional 15 min at 0° C. Following work-up, the crude reaction mixture was checked by NMR spectroscopy with 1,3,5-trimethoxybenzene as internal standard. The crude mixture was then purified by flash column chromatography on silica (eluent: 10:90 EtOAc:Hexanes) to afford the title compound (5b) (42.5 mg, 0.189 mmol, 63%) as a colorless oil. TLC: $R_f$=0.45 (20:80 EtOAc:Hexanes; UV, CAM). $^1$H NMR (500 MHz, DMSO-d$_6$) (343K): δ 7.44-7.22 (m, 10H), 4.60 (br s, 2H), 2.87 (s, 3H). Spectral data are in accord with that previously reported in the literature. HRMS-ESI (m/z): [M+H]$^+$ calculated for [C$_{15}$H$_{16}$ON]$^+$: 226.1226, found: 226.1221.

Synthesis of N,N-dibenzyl-O-(tert-butyl)hydroxylamine (4a)

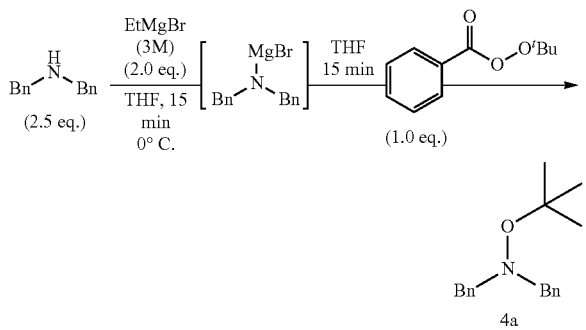

Following general procedure D, dibenzylamine (144 μL, 0.75 mmol, 2.5 eq.) in 0.75 mL anhydrous THF was added EtMgBr (3 M in diethyl ether) (200 μL, 0.6 mmol, 2.0 eq.) and the solution was stirred for 15 min. After which, tert-butyl peroxybenzoate (58 mg, 0.3 mmol, 1.0 eq.) was added dropwise in 0.75 mL anhydrous THF. The solution was stirred for an additional 15 min at 0° C. Following work-up, the crude reaction mixture was purified by flash column chromatography on silica (eluent: 10:90 EtOAc: Hexanes) to afford the title compound (4a) (54.1 mg, 0.201 mmol, 67%) as a yellow oil. TLC: $R_f$=0.90 (10:90 EtOAc: Hexanes, UV, CAM). $^1$H NMR (500 MHz, CDCl$_3$): δ 7.34-7.23 (m, 10H), 3.86 (d, J=12.84 Hz, 2H), 3.79 (d, J=13.02 Hz, 2H), 1.04 (s, 9H). $^{13}$C NMR (126 MHz, CDCl$_3$): δ 138.1 (2C), 130.1 (4C), 128.2 (4C), 127.3 (2C), 77.9, 62.9 (2C), 27.7 (3C). HRMS-ESI (m/z): [M+H]$^+$ calculated for [C$_{18}$H$_{24}$ON]$^+$: 270.1852, found: 270.1853.

Synthesis of N-benzyl-N-methyl-O-(tert-butyl)hydroxylamine (4b)

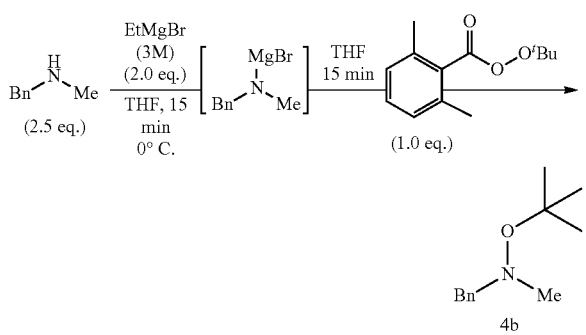

Following general procedure D, N-methylbenzylamine (97 μL, 0.75 mmol, 2.5 eq.) in 0.75 mL anhydrous THF was added EtMgBr (3 M in diethyl ether) (200 μL, 0.6 mmol, 2.0 eq.) and the solution was stirred for 15 min. After which, 2,6-dimethyl-tert-butyl peroxybenzoate (51) (67 mg, 0.3 mmol, 1.0 eq.) was added dropwise in 0.75 mL anhydrous THF. The solution was stirred for an additional 15 min at 0° C. Following work-up, the crude reaction mixture was purified by flash column chromatography on silica (eluent: 10:90 EtOAc:Hexanes) to afford the title compound (4b) (31.8 mg, 0.165 mmol, 55%) as a colorless oil. TLC: $R_f$=0.90 (10:90 EtOAc:Hexanes; UV, CAM). $^1$H NMR (500 MHz, CDCl$_3$): δ 7.35-7.24 (m, 5H), 4.11 (br d, J=12.22 Hz, 1H), 3.56 (br s, 1H), 2.46 (s, 3H), 1.21 (s, 9H). $^{13}$C NMR (126 MHz, CDCl$_3$): δ 137.9, 129.7 (2C), 128.3 (2C), 127.4, 77.9, 66.8, 46.7, 27.4 (3C). HRMS-ESI (m/z): [M+H]$^+$ calculated for [C$_{12}$H$_{20}$ON]$^+$: 194.1539, found: 194.1542.

Synthesis of 1-(tert-butoxy)-perhydroisoquinoline (4c)

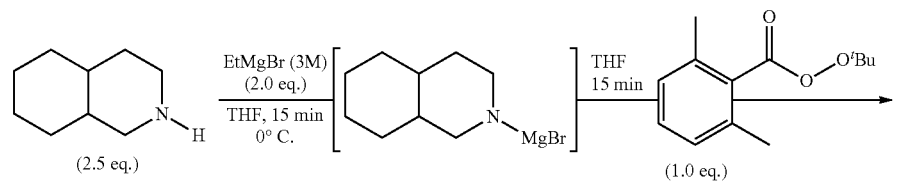

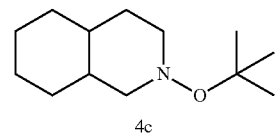

4c

Following general procedure D, to a stirred solution of perhydroisoquinoline (149 μL, 1.0 mmol, 2.5 eq.) in 1.0 mL anhydrous THF was added EtMgBr (3 M, in diethyl ether) (267 μL, 0.8 mmol, 2.0 eq.) and the solution was stirred for 15 min. After which, 2,6-dimethyl-tert-butyl peroxybenzoate (Si) (89 mg, 0.4 mmol, 1.0 eq.) was added dropwise in 1.0 mL anhydrous THF. The solution was stirred for an additional 15 min at 0° C. Following work-up, the crude reaction mixture was purified by flash column chromatography on silica (eluent: 10:90 EtOAc:Hexanes) to afford the title compound (4c) (57 mg, 0.269 mmol, 67%) as a colorless oil. TLC: $R_f$=0.90 (10:90 EtOAc:Hexanes; I$_2$). $^1$H NMR (500 MHz, CDCl$_3$): δ 3.12 (m, 1H), 2.99 (m, 1H), 2.38 (m, 1H), 2.09 (br t, J=10.6 Hz, 1H), 1.73-1.50 (m, 5H), 1.36-1.22 (m, 4H), 1.17 (s, 9H), 1.01-0.80 (m, 3H). $^{13}$C NMR (126 MHz, CDCl$_3$): δ 77.3, 65.1, 59.0, 41.8, 41.3, 32.8, 32.6, 30.9, 27.3 (3C), 26.6, 26.0. HRMS-ESI (m/z): [M+H]$^+$ calculated for [C$_{13}$H$_{26}$ON]$^+$: 212.2009, found: 212.2009.

Synthesis of 1-(tert-butoxy)-1,2,3,4-tetrahydroisoquinoline (4d)

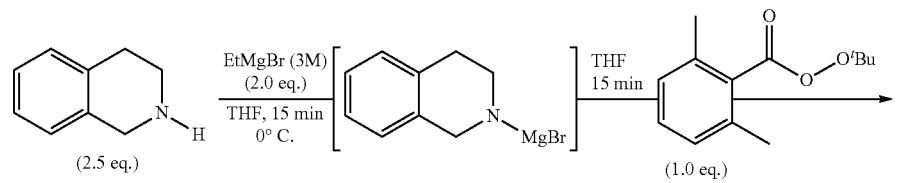

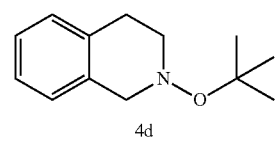

4d

Following general procedure D, to a stirred solution of 1,2,3,4-tetrahydroisoquinoline (127 μL, 1.0 mmol, 2.5 eq.) in 1.0 mL anhydrous THF was added EtMgBr (3 M in diethyl ether) (267 μL, 0.8 mmol, 2.0 eq.) and the solution was stirred for 15 min. After which, 2,6-dimethyl-tert-butyl peroxybenzoate (5l) (89 mg, 0.4 mmol, 1.0 eq.) was added dropwise in 1.0 mL anhydrous THF. The solution was stirred for an additional 15 min at 0° C. Following work-up, the crude reaction mixture was purified by flash column chromatography on silica (eluent: 10:90 EtOAc:Hexanes) to afford the title compound (4d) (65.4, 0.319 mmol, 80%) as a colorless oil. TLC: $R_f$=0.90 (10:90 EtOAc:Hexanes; UV, CAM). $^1$H NMR (500 MHz, CDCl$_3$): δ 7.14 (m, 3H), 7.03 (m, 1H), 4.16 (br d, J=14.2, 1H), 3.84 (br d, J=14.2, 1H), 3.34 (br s, 1H), 3.14 (br s, 1H), 2.87 (br s, 2H), 1.27 (s, 9H). $^{13}$C NMR (126 MHz, CDCl$_3$): δ 134.7, 133.9, 128.3, 127.0, 126.4, 125.9, 77.9, 60.3, 55.6, 29.2, 27.3 (3C). HRMS-ESI (m/z): [M+H]$^+$ calculated for [C$_{13}$H$_{20}$ON]$^+$: 206.1539, found: 206.1542.

Synthesis of 1-(tert-butoxy)-4-benzylpiperidine (4e)

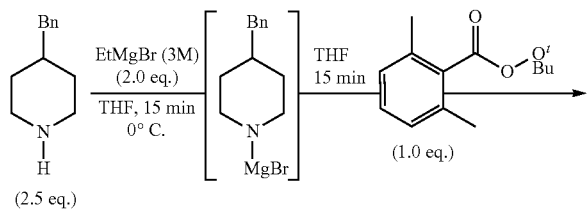

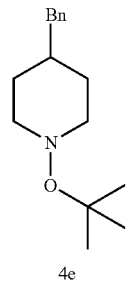

4e

Following general procedure D, to a solution of 4-benzylpiperidine (175 μL, 1.0 mmol, 2.5 eq.) in 1.0 mL anhydrous THF was added EtMgBr (3 M in diethyl ether) (267 μL, 0.8 mmol, 2.0 eq.) and the solution was stirred for 15 min. After which, 2,6-dimethyl-tert-butyl peroxybenzoate (5i) (89 mg, 0.4 mmol, 1.0 eq.) was added dropwise in 1.0 mL anhydrous THF. The solution was stirred for an additional 15 min at 0° C. Following work-up, the crude reaction mixture was purified by flash column chromatography on silica (eluent: 10:90 EtOAc:Hexanes) to afford the title compound (4e) (65.2 mg, 0.264 mmol, 66%) as a yellow oil. TLC: $R_f$=0.90 (10:90 EtOAc:Hexanes; UV, CAM). $^1$H NMR (500 MHz, CDCl$_3$): δ 7.28 (t, J=7.5 Hz, 2H), 7.19 (t, J=7.3 Hz, 1H), 7.13 (m, 2H), 3.10 (br d, J=10.1, 2H), 2.50 (d, J=6.9 Hz, 2H), 2.34 (m, 2H), 1.63 (m, 2H), 1.46 (br s, 1H), 1.35 (m, 2H), 1.18 (s, 9H). $^{13}$C NMR (126 MHz, CDCl$_3$): δ 141.0, 129.2 (2C), 128.3 (2C), 126.0, 77.4, 58.5 (2C), 43.1, 37.4, 32.2 (2C), 27.3 (3C). HRMS-ESI (m/z): [M+H]$^+$ calculated for [C$_{16}$H$_{26}$ON]$^+$: 248.2009, found: 248.2007.

Synthesis of 1-(tert-butoxy)-4-(pyridin-2'-yl)piperazine (4f)

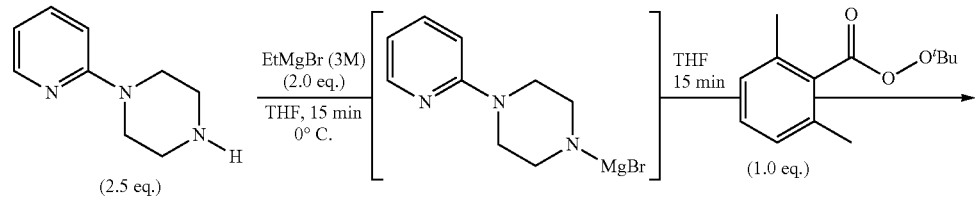

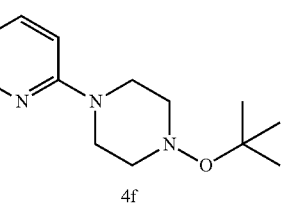

4f

Following general procedure D, to a stirred solution of 1-(2-pyridyl)piperazine (152 μL, 1.0 mmol, 2.5 eq.) in 1.0 mL anhydrous THF was added EtMgBr (3 M in diethyl ether) (267 μL, 0.8 mmol, 2.0 eq.) and the solution was stirred for 15 min. After which, 2,6-dimethyl-tert-butyl peroxybenzoate (51) (89 mg, 0.4 mmol, 1.0 eq.) was added dropwise in 1.0 mL anhydrous THF. The solution was stirred for an additional 15 min at 0° C. Following work-up, the crude reaction mixture was purified flash column chromatography on silica (eluent: 10:90 EtOAc:Hexanes) to afford the title compound (4f) (71.2 mg, 0.303 mmol, 76%) as a white solid. Melting point=91-92° C. TLC: R$_f$=0.15 (10:90 EtOAc:Hexanes; UV, CAM). $^1$H NMR (500 MHz, CDCl$_3$): δ 8.18 (dd, J=4.9, 2.0 Hz, 1H), 7.46 (ddd, J=8.9, 7.0, 2.0 Hz, 1H), 6.61 (m, 2H). 4.10 (br d, J=12.44 Hz, 2H), 3.16-3.04 (m, 4H), 2.69 (m, 2H), 1.22 (s, 9H). $^{13}$C NMR (126 MHz, CDCl$_3$): δ 159.4, 148.1, 137.6, 113.4, 107.1, 77.9, 57.2 (2C), 44.5 (2C), 27.3 (3C). HRMS-ESI (m/z): [M+H]$^+$ calculated for [C$_{13}$H$_{22}$ON$_3$]$^+$: 236.1757, found: 236.1756.

Synthesis of 1-(tert-butoxy)-4-(2'-methoxyphenyl) piperazine (4q)

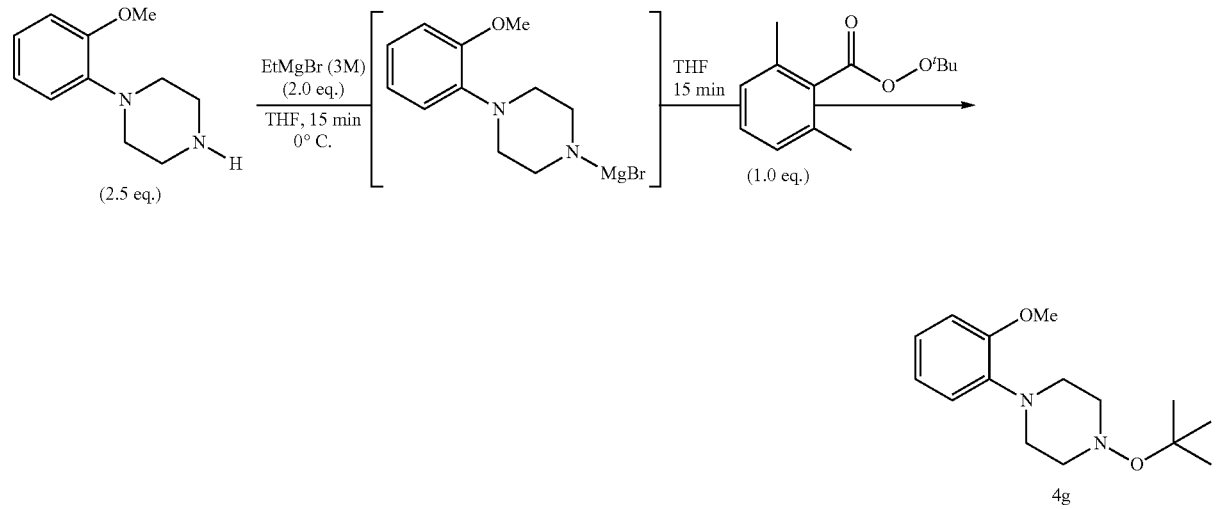

Following general procedure D, to a solution of 1-(2-methoxyphenyl)piperazine (192 mg, 1.0 mmol, 2.5 eq.) in 1.0 mL anhydrous THF was added EtMgBr (3 M in diethyl ether) (267 μL, 0.8 mmol, 2.0 eq.) and the solution was stirred for 15 min. After which, 2,6-dimethyl-tert-butyl peroxybenzoate (51) (89 mg, 0.4 mmol, 1.0 eq.) was added dropwise in 1.0 mL anhydrous THF. The solution was stirred for an additional 15 min at 0° C. Following work-up, the crude reaction mixture was purified by flash column chromatography on silica (eluent: 10:90 EtOAc:Hexanes) to afford the title compound (4 g) (70.4 mg, 0.267 mmol, 67%) as an off yellow solid. Melting point=79.0-80.0° C. TLC: R$_f$=0.40 (10:90 EtOAc:Hexanes; UV, CAM). $^1$H NMR (500 MHz, CDCl$_3$): δ 6.99 (ddd, J=8.2, 6.7, 2.2 Hz, 1H), 6.92 (m, 2H), 6.85 (dd, J=7.8, 1.3 Hz, 1H), 3.86 (s, 3H), 3.41 (br s, 2H), 3.13 (br s, 2H), 2.89 (br s, 4H), 1.23 (s, 9H). $^{13}$C NMR (126 MHz, CDCl$_3$): δ 152.4, 141.1, 122.9, 121.1, 118.3, 111.6, 77.6, 57.7 (2C), 55.5, 49.7 (2C), 27.3 (3C). HRMS-ESI (m/z): [M+H]$^+$ calculated for [C$_{15}$H$_{25}$O$_2$N$_2$]$^+$: 265.1910, found: 265.1909.

Synthesis of 1-(tert-butoxy)-4-(4'-trifluoromethylphenyl)piperazine (4h)

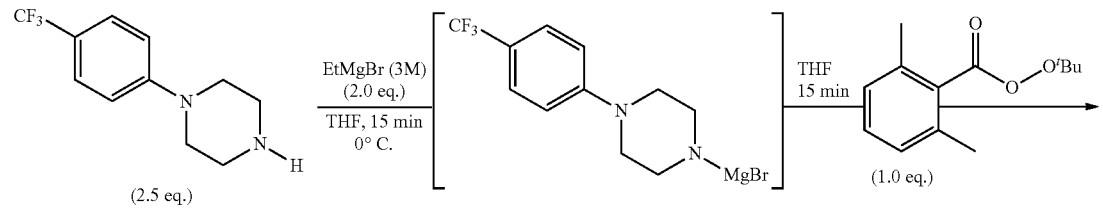

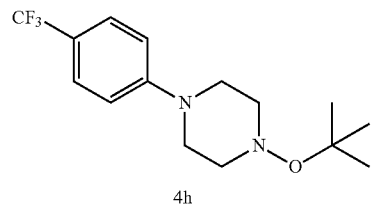

Following general procedure D, to a solution of 1-(4-trifluoromethylphenyl)piperazine (230 mg, 1.0 mmol, 2.5 eq.) in 1.0 mL anhydrous THF was added EtMgBr (3 M in diethyl ether) (267 μL, 0.8 mmol, 2.0 eq.) and the solution was stirred for 15 min. After which, 2,6-dimethyl-tert-butyl peroxybenzoate (51) (89 mg, 0.4 mmol, 1.0 eq.) was added dropwise in 1.0 mL anhydrous THF. The solution was stirred for an additional 15 min at 0° C. Following work-up, the crude reaction mixture was purified by flash column chromatography on silica (eluent: 10:90 EtOAc:Hexanes) to afford the title compound (4h) (83.5 mg, 0.275 mmol, 69%) as a white solid. Melting point=77.6-78.8° C. TLC: $R_f$=0.55 (10:90 EtOAc:Hexanes; UV, CAM). $^1$H NMR (500 MHz, CDCl$_3$): δ 7.47 (d, J=8.6 Hz, 2H), 6.90 (d, J=8.6 Hz, 2H), 3.63 (br d, J=11.9 Hz, 2H), 3.17 (br d, J=10.4 Hz, 2H), 3.05 (br d, J=11.9 Hz, 2H), 2.77 (br t, J=11.0 Hz, 2H), 1.23 (s, 9H). $^{13}$C NMR (126 MHz, CDCl$_3$): δ 153.0, 126.5 (q, J=3.8 Hz, 2C), 124.9 (q, J=271 Hz), 120.6 (q, J=33 Hz), 114.6 (2C), 78.0, 57.0 (2C), 47.2 (2C), 27.3 (3C). Decoupled $^{13}$C{$^1$H,$^{19}$F} NMR (126 MHz, CDCl$_3$): δ 153.0, 126.5 (2C), 124.9, 120.6, 114.6 (2C), 78.0, 57.0 (2C), 47.2 (2C), 27.3 (3C). $^{19}$F NMR (376 MHz, CDCl$_3$): δ −61.3 (s, 3F). HRMS-ESI (m/z): [M+H]$^+$ calculated for: [C$_{15}$H$_{22}$ON$_2$F$_3$]$^+$: 303.1679, found: 303.1677.

Synthesis of N-methyl-N-(2-(pyridine-2'-yl)ethyl)-O-(tert-butyl)hydroxylamine (4i)

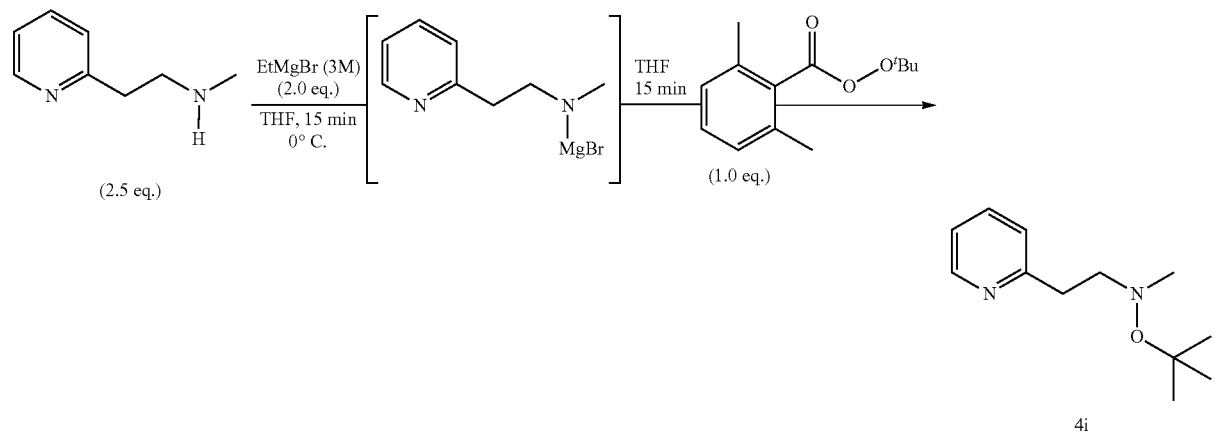

Following general procedure D, to a stirred solution of betahistine (138 μL, 1.0 mmol, 2.5 eq.) in 1.0 mL anhydrous THF was added EtMgBr (3 M in diethyl ether) (267 μL, 0.8 mmol, 2.0 eq.) and the solution was stirred for 15 min. After which, 2,6-dimethyl-tert-butyl peroxybenzoate (51) (89 mg, 0.4 mmol, 1.0 eq.) was added dropwise in 1.0 mL anhydrous THF. The solution was stirred for an additional 15 min at 0° C. Following work-up, the crude reaction mixture was purified by flash column chromatography on silica (eluent: 30:70 EtOAc:Hexanes) to afford the title compound (4i) (50 mg, 0.24 mmol, 60%) as a clear oil. TLC: $R_f$=0.10 (10:90 EtOAc:Hexanes; UV, CAM). $^1$H NMR (500 MHz, CDCl$_3$): δ 8.51 (dt, J=4.9, 1.2 Hz, 1H), 7.58 (td, J=7.6, 1.8 Hz, 1H), 7.17 (d, J=7.7 Hz, 1H), 7.09 (ddd, J=7.7, 4.9, 1.1 Hz, 1H), 3.15-2.95 (m, 4H), 2.59 (s, 3H), 1.14 (s, 9H). $^{13}$C NMR (126 MHz, CDCl$_3$): δ 160.6, 149.3, 136.3, 123.3, 121.2, 77.5, 61.9, 47.1, 35.9, 27.5 (3C). HRMS-ESI (m/z): [M+H]$^+$ calculated for [C$_{12}$H$_{21}$ON$_2$]$^+$: 209.1648, found: 209.1647.

Synthesis of 11-(1'-(tert-butoxy)piperidin-4'-ylidene)-8-chloro-6,11-dihydro-5H-benzo[5,6]cyclohepta[1,2-b]pyridine (4i)

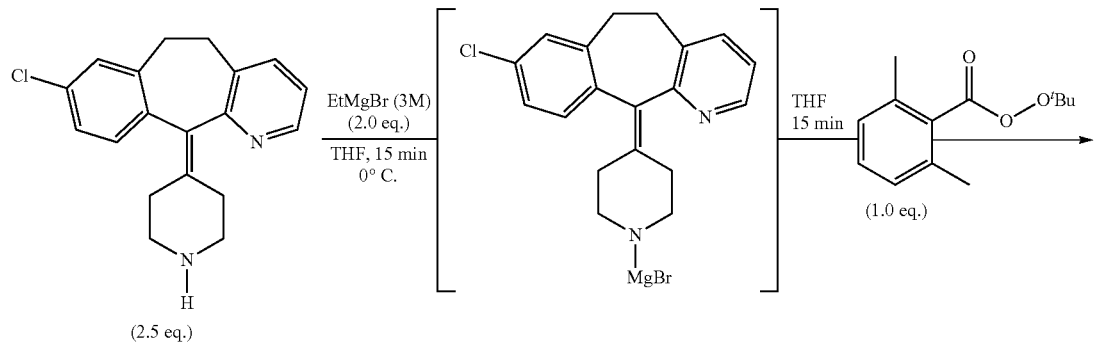

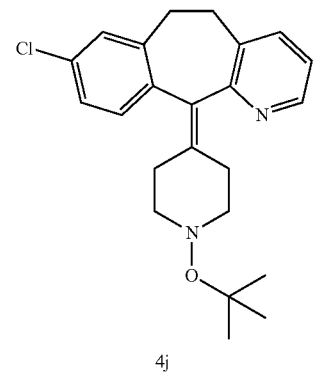

4j

Following general procedure A, to a stirred solution of desloratadine (310 mg, 1.0 mmol, 2.5 eq.) in 1.0 mL anhydrous THF was added EtMgBr (3 M in diethyl ether) (267 µL, 0.8 mmol, 2.0 eq.) and the solution was stirred for 15 min. After which, 2,6-dimethyl-tert-butyl peroxybenzoate (Si) (89 mg, 0.4 mmol, 1.0 eq.) was added dropwise in 1.0 mL anhydrous THF. The solution was stirred for an additional 15 min at 0° C. Following work-up, the crude reaction mixture was purified by flash column chromatography on silica (eluent: 10:90 EtOAc:Hexanes) to afford the title compound (4j) (99 mg, 0.259 mmol, 65%) as an orange foam. TLC: $R_f$=0.20 (10:90 EtOAc:Hexanes; UV, CAM). $^1$H NMR (500 MHz, CDCl$_3$): δ 8.38 (dd, J=4.8, 1.7 Hz, 1H), 7.43 (dd, J=7.7, 1.7 Hz, 1H), 7.12 (m, 3H), 7.07 (dd, J=7.7, 4.8 Hz, 1H), 3.37 (m, 2H), 3.09 (br s, 2H), 2.79 (m, 2H), 2.55-2.08 (m, 6H), 1.17 (s, 9H). $^{13}$C NMR (126 MHz, CDCl$_3$): δ 157.6, 146.7, 139.6, 138.0 (2C), 137.5, 133.5, 133.1, 132.8, 130.9, 129.1, 126.1, 122.3, 77.6, 58.9 (2C), 31.9, 31.5, 30.5, 30.3, 27.2 (3C). HRMS-ESI (m/z): [M+H]$^+$ calculated for [C$_{23}$H$_{28}$ON$_2$$^{35}$Cl]: 383.1885, found: 383.1881.

Synthesis of 3-(4'-(tert-butoxy)piperazin-1'-yl)benzo[d]isothiazole (4 k)

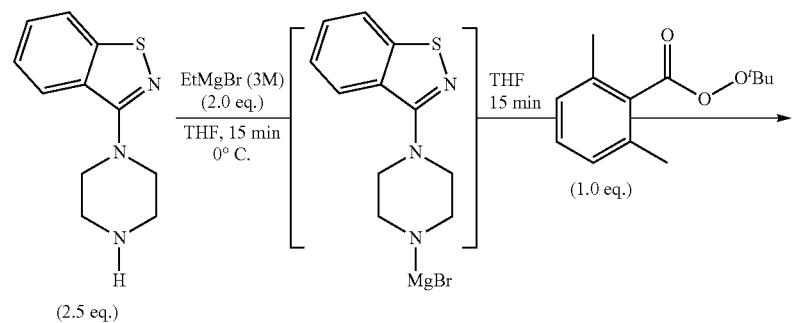

-continued

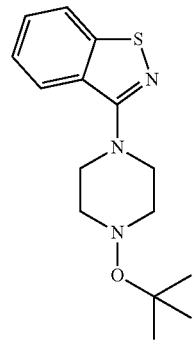

4k

Following general procedure A, to a stirred solution of 3-(1'-piperazinyl)-1,2-benzo[d]isothiazole (219 mg, 1.0 mmol, 2.5 eq.) in 1.0 mL anhydrous THF was added EtMgBr (3 M in diethyl ether) (267 μL, 0.8 mmol, 2.0 eq.) and the solution was stirred for 15 min. After which, 2,6-dimethyl-tert-butyl peroxybenzoate (51) (89 mg, 0.4 mmol, 1.0 eq.) was added dropwise in 1.0 mL anhydrous THF. The solution was stirred for an additional 15 min at 0° C. Following work-up, the crude reaction mixture was purified by flash column chromatography on silica (eluent: 10:90 EtOAc:Hexanes) to afford the title compound (4 k) (86 mg, 0.295 mmol, 74%) as an off yellow oil. TLC: $R_f$=0.40 (10:90 EtOAc:Hexanes; UV, CAM). $^1$H NMR (500 MHz, CDCl$_3$): δ 7.89 (d, J=8.1 Hz, 1H), 7.80 (d, J=7.9 Hz, 1H), 7.46 (t, J=7.8 Hz, 1H), 7.35 (t, J=7.5 Hz, 1H), 3.88 (br d, J=12.4, 2H), 3.30 (m, 2H), 3.19 (br d, J=10.2 Hz, 2H), 2.89 (br t, J=10.7 Hz, 2H), 1.23 (s, 9H). $^{13}$C NMR (126 MHz, CDCl$_3$): δ 163.7, 152.8, 128.1, 127.7, 124.1, 124.0, 120.7, 78.0, 57.3 (2C), 49.2 (2C), 27.3 (3C). HRMS-ESI (m/z): [M+H]$^+$ calculated for [C$_{15}$H$_{22}$ON$_3$$^{32}$S]$^+$: 292.1478, found: 292.1478.

Synthesis of 1-(tert-butoxy)-4-(2',3'-dichlorophenyl)piperazine (4l)

Following general procedure A, to a stirred solution of 1-(2,3-dichlorophenyl)piperazine (181 μL, 1.0 mmol, 2.5 eq.) in 1.0 mL anhydrous THF was added EtMgBr (3 M in diethyl ether) (267 μL, 0.8 mmol, 2.0 eq.) and the solution was stirred for 15 min. After which, 2,6-dimethyl-tert-butyl peroxybenzoate (51) (89 mg, 0.4 mmol, 1.0 eq.) was added dropwise in 1.0 mL anhydrous THF. The solution was stirred for an additional 15 min at 0° C. Following work-up, the crude reaction mixture was purified by flash column chromatography on silica (eluent: 10:90 EtOAc:Hexanes) to afford the title compound (4l) (87.4 mg, 0.289 mmol, 72%) as a white solid. Melting point=92-93° C. TLC: $R_f$=0.70 (10:90 EtOAc:Hexanes; UV, CAM). $^1$H NMR (500 MHz, CDCl$_3$): δ 7.13 (m, 2H), 6.95 (dd, J=7.3, 2.2 Hz, 1H), 3.28-2.88 (m, 8H), 1.22 (s, 9H). $^{13}$C NMR (126 MHz, CDCl$_3$): δ 151.0, 134.2, 127.7, 127.5, 124.7, 118.7, 77.8, 57.6 (2C), 50.3 (2C), 27.3 (3C). HRMS-ESI (m/z):[M+H]$^+$ calculated for [C$_{14}$H$_{21}$ON$_2$$^{35}$Cl$_2$]$^+$: 303.1025, found: 303.1023.

Scale Up to 850 mg (3.83 mmol)

Following general procedure A, to a stirred solution of 1-(2,3-dichlorophenyl)piperazine (1.74 mL, 9.57 mmol, 2.5 eq.) in 9.5 mL anhydrous THF was added EtMgBr (3 M in

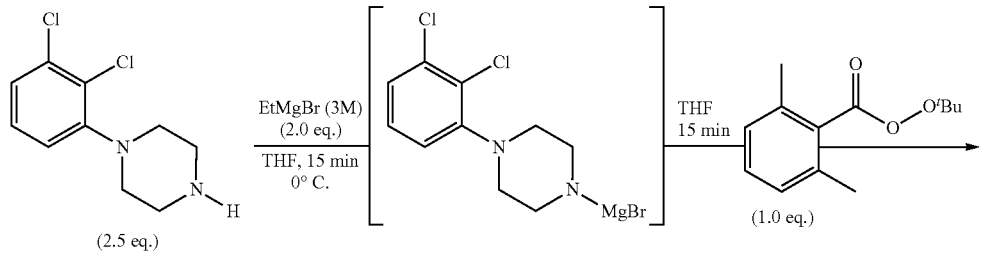

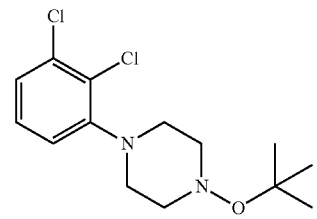

4l diethyl ether) (2.55 mL, 7.66 mmol, 2.0 eq.) and the solution was stirred for 15 min. After which, 2,6-dimethyl-tert-butyl peroxybenzoate (51) (850 mg, 3.83 mmol, 1.0 eq.) was added dropwise in 1.0 mL anhydrous THF. The solution was stirred for an additional 15 min at 0° C. Following work-up, the crude reaction mixture was purified by flash column chromatography on silica (eluent: 10:90 EtOAc:Hexanes) to afford the title compound (4l) (769 mg, 2.54 mmol, 66%) as a white solid. Title compound was recrystallized in hot ethanol with slow evaporation of the solvent.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

REFERENCES

1. Alcaide, A., et al. Galacto Configured N-Aminoaziridines: A New Type of Irreversible Inhibitor of β-Galactosidases. Org. and Biomolecular Chem. 2015, 13, 5690.
2. Axerio-Cilies, P. et al. Investigation of the Incidence of "Undesirable" Molecular Moieties for High Throughput Screening Compound Libraries in Marketed Drug Compounds. Eur. J. Med. Chem. 2009, 46, 5833.
3. Banerjee, A. et al. Direct N—O Bond Formation via Oxidation of Amines with Benzoyl Peroxide. Chem. Sci. 2019, 10, 2124.
4. Barelier, S. et al. Increasing Chemical Space Coverage by Combining Empirical and Computational Fragment Screens. ACS Chem. Biol. 2014, 9, 1528.
5. Barnes-Seeman, D.; et al. Metabolically Stable tert-Butyl Replacement. ACS Med. Chem. Lett. 2013, 4, 514-516.
6. Biloski, A. J. et al. Improved Oxidation of Amines with Dibenzoyl Peroxide. Synthesis 1983, 7, 537.
7. Bisel, P.; et al. The tert-Butyl Group in Chemistry and Biology. Org. Biomol. Chem. 2008, 6, 2655-2665.
8. Brems, D. N., et al. Photoaffinity Labeling of the Catalytic Site of Prenyltransferase. Biochem. 1979, 18, 860.
9. Brown, D. G. et al. Analysis of Past and Present Synthetic Methodologies on Medicinal Chemistry: Where Have All the New Reactions Gone? J. Med. Chem. 2015, 59, 4443.
10. Burkhard, J. A.; et al. Oxetanes as Versatile Elements in Drug Discovery and Synthesis. Angew. Chem. Int. Ed. 2010, 49, 9052-9067.
11. Casey, A. B.; et al Classics in Chemical Neuroscience: Aripiprazole. ACS Chem. Neurosci. 2017, 8, 1135-1146.
12. Castellino, A. J. et al. Synthesis of Phenoxyamines. J. Org. Chem. 1984, 49, 1348.
13. Cline, G. W.; et al. The Aminolysis of N-Hydroxysuccinimide Esters. A Structure-Reactivity Study. J. Am. Chem. Soc. 1987, 109, 3087-3091.
14. Dandapani, S. et al. Selecting, Acquiring, and Using Small Molecule Libraries for High-Throughput Screening. Curr. Protoc. Chem. Biol. 2012, 4, 177.
15. Denisenko, A.; et al. Saturated Bioisosteres of ortho-Substituted Benzenes. Angew. Chem. Int. Ed. 2020, 59, 20515-20521.
16. Dhanju, S. et al. Synthesis of N,N,O-Trisubstituted Hydroxylamines by Stepwise Reduction and Substitution of O-Acyl N,N-Disubstituted Hydroxylamines. Org. Lett. 2016, 18, 1820.
17. Dhanju, S. et al. Synthesis of Trialkylhydroxylamines by Stepwise Reduction of O-Acyl N,N-Disubstituted Hydroxylamines: Substituent Effects on the Reduction of O-(1-Acyloxyalkyl)hydroxylamines and on the Conformational Dynamics of N-Alkoxypiperidines. J. Org. Chem. 2017, 82, 5345.
18. Dhanju, S. et al. Synthesis, Cytotoxicity and Genotoxicity of 10-Aza-9-oxakalkitoxin, An N,N,O-Trisubstituted Hydroxylamine Analog, or Hydroxalog, of a Marine Natural Product, J. Am. Chem. Soc. 2020, 142, 9147.
19. Ferry, A.; et al. Synthesis and Evaluation of Di- and Trimeric Hydroxylamine-Based β-(1→3)-Glucan Mimetics. J. Am. Chem. Soc. 2014, 136, 14852-14857.
20. Foot, 0. F. et al. Synthesis of O-Alkylhydroxylamines by Electrophilic Amination of Alkoxides. Chem. Comm. 2000, 975.
21. Goddard-Borger, E. D., et al. An Efficient, Inexpensive, and Shelf-Stable Diazotransfer Reagent: Imidazole-1-sulfonyl Azide Hydrochloride. Org. Lett. 2007, 9, 3797.
22. Goff, R. D. et al. Neoglycosylation and Neoglycorandomization: Enabling Tools for Drug Discovery of Novel Glycosylated Bioactive Probes and Early Stage Leads. Med. Chem. Comm. 2014, 5, 1036.
23. Hill, J.; et al. Diversity-Oriented Synthesis of N,N,O-Trisubstituted Hydroxylamines from Alcohols and Amines by N—O Bond Formation. J. Am. Chem. Soc. 2020, 142, 14820-14825.
24. Hoang, K. M.; et al. Programmable Synthesis of 2-Deoxyglycosides. J. Am. Chem. Soc. 2019, 141, 8098-8103.
25. Hu, W.; et al. Identification of Hits as Matrix-2 Protein Inhibitors through the Focused Screening of a Small Primary Amine Library. J. Med. Chem. 2010, 53, 3831-3834.
26. Ji, P., et al. Visible-Light-Mediated, Chemo- and Stereoselective Radical Process for the Synthesis of C-Glycoamino Acids. Org. Lett. 2019, 21, 3086.
27. Karageorgis, G. et al. Principle and Design of Pseudo-Natural Products. Nat. Chem. 2020, 12, 227.
28. Kelly, D. R. et al. The Mechanism of the Tertiary Amine Catalysed Isomerization of Endoperoxides to Hydroxyketones: Synthesis and Chemistry of the Intermediate Postulated in the Peroxide Attack Mechanism. Tetrahedron Lett. 2002, 43, 9331.
29. Kyasa, S. et al. Synthesis of S,S,O-Orthoesters and 1,1,-Difluoroalkyl Ethers via Reaction of Peroxides with Lithiated 1,3-Dithianes. Org. Lett. 2014, 16, 5235.
30. Kyasa, S.; et al. Synthesis of Ethers via Reaction of Carbanions and Monoperoxyacetals. J. Org. Chem. 2015, 80, 12100-12114.
31. Lawesson, S.-O.; et al. Reactions of Grignard Reagents with Peroxy Compounds. J. Am. Chem. Soc. 1959, 81, 4230-4233.
32. Leeson, P. D.; et al; The Influence of the 'Organizational Factor' on Compound Quality in Drug Discovery. Nat. Rev. Drug Disc. 2011, 10, 749-765.
33. Liang, R.; et al. Design and Synthesis of Conformationally Constrained tri-Substituted Ureas as Potent Antagonists of the Human Glucagon Receptor. Bioorg. Med. Chem. Lett. 2007, 17, 587-592.
34. Locklear, M.; et al. The Chemistry of Peresters. Eur. J. Org. Chem. 2020, 31, 4814-4840.
35. Lovering, F. Escape from Flatland 2: Complexity and Promiscuity. MedChemCommun. 2013, 4, 515-519.
36. Lovering, F.; et al. Escape from Flatland: Increasing Saturation as an Approach to Improving Clinical Success. J. Med. Chem. 2009, 52, 6752-6756.

37. Luo, Y.-R. In Handbook of Bond Dissociation Energies in Organic Compounds. CRC Press: Boca Raton, 2003; p 203, 229.
38. Mader, P.; et al. Sulfoximines as Rising Stars in Modern Drug Discovery? Current Status and Perspective on an Emerging Functional Group in Medicinal Chemistry. J. Med. Chem. 2020, 63, 14243-14275.
39. Malik, G.; et al. Asymmetric Synthesis of Polyhydroxylated N-Alkoxypiperidines by Ring-Closing Double Reductive Amination: Facile Preparation of Isofagamine and Analogues. Org. Lett. 2012, 14, 596-599.
40. Malik, G.; et al. N—O Bond as a Glycosidic-Bond Surrogate: Synthetic Studies Towards Polyhydroxylated N-Alkoxypiperidines. Chem.-Eur. J. 2013, 19, 2168-2179.
41. Meanwell, N. A.; Synopsis of Some Recent Tactical Application of Bioisosteres in Drug Design. J. Med. Chem. 2011, 54, 2529-2591.
42. Meesters, A. C. M.; et al. The Direct Synthesis of N-t-Alkyl-O-t-butylhydroxylamines from t-Butyl Peroxybenzoate and the Lithium Salts of Primary t-Alkylamines. Synthesis 1978, 9, 679-680.
43. Melman, A. Synthesis of Hydroxylamines. In Chemistry of Hydroxylamines, Oximes and Hydroxamic Acids, Rappoport, Z.; Liebman, J. F., Eds. Wiley: Chichester, 2009; Vol. 1, pp 117-163.
44. Miura, Y.; et al. First Isolation of N-Alkoxyaminyl Radicals. Chem. Commun. 2001, 627-628.
45. Miura, Y.; et al. Isolation and Magnetic Properties of Heterocycle-Carrying N-Alkoxyarylaminyl Radicals. J. Org. Chem. 2003, 68, 10158-10161.
46. Miura, Y.; et al. Syntheses of Stable N-tert-Alkoxyarylaminyl Mono- and Diradicals by the Reaction of the Lithium Salts of 2,4,6-Trisubstituted Anilines with tert-Alkyl Mono- and Diperoxybenzoates. J. Org. Chem. 2005, 70, 4177-4179.
47. Mollin, J. et al. Basicity of Hydroxylamine and Its Derivatives. Chem. Zvesti 1975, 29, 39.
48. Morrison, K. C. et al. Natural Products as Starting Points for the Synthesis of Complex and Diverse Compounds. Nat. Prod. Rep. 2014, 31, 6.
49. Mukherjee, P.; et al. Trifluoromethyl Oxetanes: Synthesis and Evaluation as a tert-Butyl Isostere. ChemMedChem 2017, 12, 1574-1577.
50. Murray, C. W. et al. Opportunity Knocks: Organic Chemistry for Fragment-Based Drug Discovery (FBDD). Angew. Chemie. Int. Ed. 2016, 55, 488.
51. Mykhailiuk, P. K. Saturated Bioisosteres of Benzene: Where to Go Next? Org. Biomol. Chem. 2019, 17, 2839-2849.
52. Nicotra, F. et al. Chemoselective Neoglycosylation. Adv. Carbohydr. Chem. Biochem. 2007, 61, 353.
53. Novak, M. et al. N-Arylhydroxylamines and Chemical Carcinogenicity. In Chemistry of Hydroxylamines, Oximes and Hydroxamic Acids, Rappoport, Z.; Liebman, J. F., Eds. Wiley: Chichester, 2011; Vol. 2, pp 115-143.
54. Palandoken, H.; et al. A Facile Synthesis of (tert-Alkoxy) amines. Tetrahedron Lett. 2005, 46, 6667-6669.
55. Pan, J.; et al. Facile Amide Formation via S-Nitrosothioacids. Org. Lett. 2011, 13, 1092-1094.
56. Patani, G. A.; et al. Bioisosterism: A Rational Approach in Drug Design. Chem. Rev. 1996, 96, 3147-3176.
57. Peltzer, R. M. et al. The Grignard Reaction Unraveling a Chemical Puzzle. J. Am. Chem. Soc. 2020, 142, 2984.
58. Raban, M. et al. Stereolabile Configurational Units and Inversional Stereochemistry in Sulfenamides and Hydroxylamines. Tetrahedron 1984, 40, 3345.
59. Riddell, F. G. et al. The Barrier to Rotation About the N—O Bond. J. Chem. Soc., Perkin Trans. 2, 1978, 707.
60. Rishton, G. M. Nonleadlikeness and Leadlikeness in Biochemical Screening. Drug Discovery Today 2003, 8, 89.
61. Schreiber, S. L. Target-Oriented and Diversity-Oriented Organic Synthesis in Drug Discovery. Science 2000, 287, 1964.
62. Seo, S.; et al. Mild Amination of Aldehydes with Amines Mediated by Lanthanide Catalysts. Org. Lett. 2008, 10, 317-319.
63. Sink, R. et al. False Positives in the Early Stages of Drug Discovery Curr. Med. Chem. 2010, 17, 4231.
64. Sodano, T. M.; et al. Recent Advances and Outlook for the Isosteric Replacement of Anilines. ACS Med. Chem. Lett. 2020, 11, 1785-1788.
65. Stepan, A. F.; et al. Application of the Bicyclo[1.1.1] pentane Motif as a Nonclassical Phenyl Ring Bioisostere in the Design of a Potent and Orally Active γ-Secretase Inhibitor. J. Med. Chem. 2012, 55, 3414-3424.
66. Stowell, C. P. et al. Neoglycoproteins: The Preparation and Application of Synthetic Glycoproteins. Adv. Carbohydr. Chem. Biochem. 1980, 37, 225.
67. Thomas, J.; et al. The Effect of Ortho Substitution on the Hydrolysis of Benzoylcholine. J. Pharm. Pharmacol. 1961, 13, 129-138.
68. Tse, E. G.; et al. Nonclassical Phenyl Bioisosteres as Effective Replacements in a Series of Novel Open-Source Antimalarials. J. Med. Chem. 2020, 63, 11585-11601.
69. Umezawa, T.; et al. Synthesis and Biological Activity of Kalkitoxin and its Analogues. J. Org. Chem. 2012, 77, 357-370.
70. Vitaku, E.; et al. Analysis of the Structural Diversity, Substitution Patterns, and Frequency of Nitrogen Heterocycles among U.S. FDA Approved Pharmaceuticals. J. Med. Chem. 2014, 57, 10257-10274.
71. Waring, M. J. Defining Optimum Lipophilicty and Molecular Weight Ranges for Drug Candidates-Molecular Weight Dependent Lower log D Limits Based on Permeability. Bioorg. Med. Chem. Lett. 2009, 19, 2844-2851.
72. Wen, P. et al. Synthesis and Evaluation of Oligomeric Thioether-Linked Carbacyclic β-(1→3)-Glucan Mimetics. J. Org. Chem. 2019, 84, 5554.
73. Westphal, M. V., et al Evaluation of tert-Butyl Isosteres: Case Studies of Physicochemical and Pharmacokinetic Properties, Efficacies, and Activities. ChemMedChem 2015, 10, 461-469.
74. Williams, H. R. et al. Peroxides. I. n-Alkyl Hydroperoxides. J. Am. Chem. Soc. 1954, 76, 2984.
75. Wipf, P.; et al. Synthesis and Biological Evaluation of the First Pentafluorosulfanyl Analogs of Mefloquine. Org. Biomol. Chem. 2009, 7, 4163-4165.
76. Wuitschik, G.; et al. Oxetanes as Promising Modules in Drug Discovery. Angew. Chem. Int. Ed. 2006, 45, 7736-7739.
77. Wuitschik, G.; et al. Oxetanes in Drug Discovery: Structural and Synthetic Insights. J. Med. Chem. 2010, 53, 3227-3246.
78. Xia, Q.; et al. Biomimetic Synthesis of Iridoid Alkaloids as Novel Leads for Fungicidal and Insecticidal Agents. J. Agric. Food Chem. 2020, 68, 12577-12584.
79. Yadav, D. K. T.; et al. tert-Butyl Peroxybenzoate Mediated Selective and Mild N-Benzoylation of Ammonia/ Amines under Catalyst- and Solvent-Free Conditions. Synlett 2015, 26, 1862-1866.

80. Yokokawa, F.; et al. An Expeditious Total Synthesis of Kalkitoxins: Determination of the Absolute Stereostructure of Natural Kalkitoxin. Tetrahedron 2004, 60, 6859-6880.
81. Zhang, F.; et al. Metal- and Solvent-Free Synthesis of Amides using Substitute Formamides as an Amino Source under Mild Conditions. Sci. Rep. 2019, 9, 2787.

What is claimed is:

1. A method for producing a trisubstituted hydroxylamine, the method comprising reacting a monoperoxyacetal compound with a secondary amide, wherein the monoperoxyacetal compound has the structure I or II

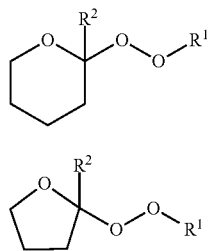

wherein
$R^1$ is a substituted or unsubstituted linear or branched alkyl group, a substituted or unsubstituted cycloalkyl group or heterocycloalkyl group, a polyether group, an alkylpolyether group, or a protected or unprotected monosaccharide, disaccharide, or polysaccharide, and
$R^2$ is hydrogen, an aryl group, a heteroaryl group, or a substituted or unsubstituted alkyl group; and
the secondary amide has the structure IV

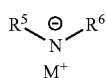

wherein
$R^5$ and $R^6$ are, independently, a substituted or unsubstituted alkyl group, a substituted or unsubstituted cycloalkyl group or heterocycloalkyl group, a substituted or unsubstituted aryl group, or a substituted or unsubstituted heteroaryl group, or wherein $R^5$ and $R^6$ together form a substituted or unsubstituted cycloalkyl group or heterocycloalkyl group, and
$M^+$ is Li, MgBr, MgCl, or MgI, wherein the secondary amide is produced by reacting a secondary amine with a Grignard reagent or an alkyl lithium, and
wherein the trisubstituted hydroxylamine has the structure V

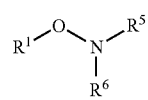

wherein a molar ratio of monoperoxyacetal compound to the secondary amide is from 1:1 to 1:5.

2. The method of claim 1, wherein $R^1$ is a substituted or unsubstituted linear or branched alkyl group.

3. The method of claim 1, wherein the substituted alkyl group comprises:

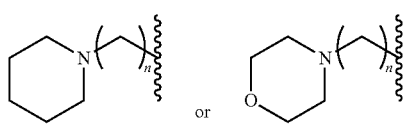

and wherein n is from 1 to 5.

4. The method of claim 1, wherein $R^1$ is 1-piperidinylethyl, 1-morpholinoethyl

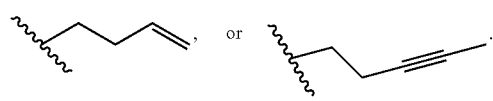

5. The method of claim 1, wherein $R^2$ is methyl or phenyl.

6. The method of claim 1, wherein $R^5$ and $R^6$ are both benzyl, phenyl, or ethyl, or wherein $R^5$ is phenyl and $R^6$ is 4-chlorophenyl, or wherein $R^5$ methyl and $R^6$ is phenyl, or wherein $R^5$ and $R^6$ together form a substituted or unsubstituted piperidine, piperazine, pyrrolidine, morpholine, indoline, or 1,2,3,4-tetrahydroquinoline ring system.

7. The method of claim 1, wherein the Grignard agent is an alkyl Grignard agent.

8. The method of claim 1, wherein the secondary amine is an alkaloid or is derived from an alkaloid.

9. The method of claim 1, wherein the monoperoxyacetal compound and secondary amide are reacted in an organic solvent selected from the group consisting of tetrahydrofuran (THF), 2-methyltetrahydrofuran (2-methyl THF), diethyl ether, methyl tent-butyl ether (MTBE), 1,4-dioxane, 1,2-dimethoxyethane, pentane, hexanes, heptanes, cyclohexanes, N,N'-dimethylpropyleneurea (DMPU), and a combination thereof.

10. The method of claim 1, wherein the monoperoxyacetal compound and secondary amide are reacted in an organic solvent, wherein the solvent is tetrahydrofuran (THF).

11. The method of claim 1, wherein the monoperoxyacetal compound and the secondary amide are reacted at a temperature of from about −10° C. to about 25° C.

12. The method of claim 1, wherein the alkyl lithium is n-butyl lithium.

* * * * *